US010324085B2

(12) United States Patent
Cotnoir-White et al.

(10) Patent No.: US 10,324,085 B2
(45) Date of Patent: Jun. 18, 2019

(54) SYSTEMS AND METHODS FOR THE MONITORING OF PROTEIN COMPLEX FORMATION IN CELLS

(71) Applicant: UNIVERSITÉ DE MONTRÉAL, Montreal (CA)

(72) Inventors: David Cotnoir-White, Montreal (CA); Sylvie Mader, Ville Mont-Royal (CA); Étienne Gagnon, Montreal (CA); Michel Bouvier, Montreal (CA)

(73) Assignee: UNIVERSITÉ DE MONTRÉAL, Montreal (CA)

(*) Notice: Subject to any disclaimer, the term of this patent is extended or adjusted under 35 U.S.C. 154(b) by 0 days.

(21) Appl. No.: 15/107,266

(22) PCT Filed: Dec. 23, 2014

(86) PCT No.: PCT/CA2014/051266
§ 371 (c)(1),
(2) Date: Jun. 22, 2016

(87) PCT Pub. No.: WO2015/095973
PCT Pub. Date: Jul. 2, 2015

(65) Prior Publication Data
US 2017/0038367 A1 Feb. 9, 2017

Related U.S. Application Data

(60) Provisional application No. 61/920,070, filed on Dec. 23, 2013.

(51) Int. Cl.
G01N 33/68 (2006.01)
G01N 33/542 (2006.01)
G01N 33/74 (2006.01)

(52) U.S. Cl.
CPC ....... *G01N 33/542* (2013.01); *G01N 33/6845* (2013.01); *G01N 33/743* (2013.01); *G01N 2333/705* (2013.01); *G01N 2333/70567* (2013.01); *G01N 2333/726* (2013.01); *G01N 2333/90241* (2013.01); *G01N 2500/04* (2013.01)

(58) Field of Classification Search
CPC .................. G01N 33/6845; G01N 33/542
USPC .......................................................... 435/7.1
See application file for complete search history.

(56) References Cited

FOREIGN PATENT DOCUMENTS

CA 2869914 4/2013

OTHER PUBLICATIONS

Navarro et al., Interactions between Intracellular Domains as Key Determinants of the Quaternary Structure and Function of Receptor Heteromers, The Journal of Biological Chemistry vol. 285, No. 35, pp. 27346-27359, Aug. 27, 2010.*
Ishikawa et al., Advanced Fluorescence Microscopy Techniques—FRAP, FLIP, FLAP, FRET and FLIM, Molecules 2012, 17, 4047-4132.*
Breton et al. Multiplexing of multicolor bioluminescence resonance energy transfer. Biophysical Journal. vol. 99, pp. 4037-4046, Dec. 2010. (Year: 2010).*
Carriba, P., Navarro, G., Ciruela, F., Ferre, S., Casado, V., Agnati, L., Cortes, A., Mallol, J., Fuxe, K., Canela, E.I. et al. (2008) Detection of heteromerization of more than two proteins by sequential BRET-FRET. Nat Methods, 5, 727-733.
Harrington, W.R., Sheng, S., Barnett, D.H., Petz, L.N., Katzenellenbogen, J.A. and Katzenellenbogen, B.S. (2003) Activities of estrogen receptor alpha- and beta-selective ligands at diverse estrogen responsive gene sites mediating transactivation or transrepression. Mol Cell Endocrinol, 206, 13-22.
Haustein, E., Jahnz, M. and Schwille, P. (2003) Triple FRET: a tool for studying long-range molecular interactions. Chemphyschem, 4, 745-748.
Kim, S.H., Tamrazi, A., Carlson, K.E. and Katzenellenbogen, J.A. (2005) A proteomic microarray approach for exploring ligand-initiated nuclear hormone receptor pharmacology, receptor selectivity, and heterodimer functionality. Mol Cell Proteomics, 4, 267-277.
Kocan, M., See, H.B., Seeber, R.M., Eidne, K.A. and Pfleger, K.D. (2008) Demonstration of improvements to the bioluminescence resonance energy transfer (BRET) technology for the monitoring of G protein-coupled receptors in live cells. J Biomol Screen, 13, 888-898.
Leibowitz, M.D., Ardecky, R.J., Boehm, M.F., Broderick, C.L., Carfagna, M.A., Crombie, D.L., D'Arrigo, J., Etgen, G.J., Faul, M.M., Grese, T.A. et al. (2006) Biological characterization of a heterodimer-selective retinoid X receptor modulator: potential benefits for the treatment of type 2 diabetes. Endocrinology, 147, 1044-1053.
Luker, G.D. and Luker, K.E. (2011) Luciferase protein complementation assays for bioluminescence imaging of cells and mice. Methods Mol Biol., 680, 29-43. Molecular Imaging, Chapter 22.
Martel, C., Dugre-Brisson, S., Boulay, K., Breton, B., Lapointe, G., Armando, S., Trepanier, V., Duchaine, T., Bouvier, M. and Desgroseillers, L. (2010) Multimerization of Staufen1 in live cells. RNA, 16, 585-597.

(Continued)

Primary Examiner — Jennifer Dunston
(74) Attorney, Agent, or Firm — Alain Dumont

(57) ABSTRACT

Described herein is a bioluminescence resonance energy transfer (BRET) based system and method to monitor ternary complex formation in real-time in live cells with high sensitivity and accuracy. This system transfers energy simultaneously between a luciferase donor and intermediate and terminal acceptors, appropriately chosen to also enable transfer from the intermediate to terminal acceptor while minimizing contaminating signals. The system may also be adapted for quaternary complex detection by including a protein complementation assay (PCA) component. The system is broadly applicable to the detection of any protein ternary/quaternary complex such as those involving nuclear receptors, GPCRs, Receptor Tyrosine Kinase (RTKs), multimeric enzymes or structural proteins.

9 Claims, 27 Drawing Sheets
Specification includes a Sequence Listing.

(56) References Cited

OTHER PUBLICATIONS

Paulmurugan, R., Tamrazi, A., Massoud, T.F., Katzenellenbogen, J.A. and Gambhir, S.S. (2011) In vitro and in vivo molecular imaging of estrogen receptor alpha and beta homo- and heterodimerization: exploration of new modes of receptor regulation. Mol Endocrinol, 25, 2029-2040.

PCT International Search Report and Written Opinion in respect of PCT/CA2014/051266, dated Apr. 13, 2015.

Pfleger, K.D. and Eidne, K.A. (2006) Illuminating insights into protein-protein interactions using bioluminescence resonance energy transfer (BRET). Nat Methods, 3, 165-174.

Powell, E. and Xu, W. (2008) Intermolecular interactions identify ligand-selective activity of estrogen receptor alpha/beta dimers. Proc Natl Acad Sci USA, 105, 19012-19017.

Powell, E., Shanle, E., Brinkman, A., Li, J., Keles, S., Wisinski, K.B., Huang, W. and Xu, W. (2012) Identification of estrogen receptor dimer selective ligands reveals growth-inhibitory effects on cells that co-express ERalpha and ERbeta. PLoS One, 7, e30993.

Rebois, R.V., Robitaille, M., Petrin, D., Zylbergold, P., Trieu, P. and Hebert, T.E. (2008) Combining protein complementation assays with resonance energy transfer to detect multipartner protein complexes in living cells. Methods, 45, 214-218.

Saenz del Burgo, L. and Milligan, G. (2010) Heterodimerisation of G protein-coupled receptors: implications for drug design and ligand screening. Expert Opin Drug Discov, 5, 461-474.

Sun, Y., Wallrabe, H., Booker, C.F., Day, R.N. and Periasamy, A. (2010) Three-color spectral FRET microscopy localizes three interacting proteins in living cells. Biophys J, 99, 1274-1283.

Truong, K. and Ikura, M. (2001) The use of FRET imaging microscopy to detect protein-protein interactions and protein conformational changes in vivo. Curr Opin Struct Biol, 11, 573-578.

\* cited by examiner

Sequential Resonance Energy Transfer (SRET)

```
                         SEQUENCE LISTING

<160> NUMBER OF SEQ ID NOS: 11

<210> SEQ ID NO 1
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 1
gatctaacca tgaagcataa aattttgcac agactcttgc aggacagcag tctcgagatg      60
aagcataaaa ttttgcacag actcttgcag gacagcagtc tcgag                    105

<210> SEQ ID NO 2
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 2
gatctaacca tgaagcataa aattgcgcac agagccgcgc aggacagcag tctcgagatg      60
aagcataaaa ttgcgcacag agccgcgcag gacagcagtc tcgag                    105

<210> SEQ ID NO 3
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 3
gatcgagccc actccacacc tccaaaaaac aaacgaaacg ttcgagatcc caaggatcga      60
gcccactcca cacctccaaa aaacaaacga aacgttcgag atcccaag                 108

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
atgtactctc aaaccagtca caaa                                            24

<210> SEQ ID NO 5
<211> LENGTH: 18
<212> TYPE: DNA
```

<210> SEQ ID NO 6
<211> LENGTH: 311
<212> TYPE: PRT
<213> ORGANISM: Renilla reniformis
<213> ORGANISM: Artificial Sequence
<220> FEATURE:
<223> OTHER INFORMATION: Synthetic oligonucleotide

<400> SEQUENCE: 5 tgagggcta ccctcctg         18

<400> SEQUENCE: 6

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 7
<211> LENGTH: 236

<212> TYPE: PRT
<213> ORGANISM: Clavularia

<400> SEQUENCE: 7

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
    130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys
225                 230                 235
```

<210> SEQ ID NO 8
<211> LENGTH: 239
<212> TYPE: PRT
<213> ORGANISM: Artificial Sequence
<220> FEATURE:
<223> OTHER INFORMATION: Synthetic mutant YFP protein

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
```

```
                100              105              110
Val Lys Phe Glu Gly Asp Thr Leu Val Asn Arg Ile Glu Leu Lys Gly
            115                  120                  125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 237
<212> TYPE: PRT
<213> ORGANISM: Artificial Sequence
<220> FEATURE:
<223> OTHER INFORMATION: Synthetic BFP variant protein

<400> SEQUENCE: 9

Met Val Ser Lys Gly Glu Glu Leu Ile Lys Glu Asn Met His Met Lys
1               5                   10                  15

Leu Tyr Met Glu Gly Thr Val Asp Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
130                 135                 140

Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
                165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
        195                 200                 205

Ala Asn Asn Glu Thr Tyr Val Glu Gln His Glu Val Ala Val Ala Arg
    210                 215                 220

Tyr Cys Asp Leu Pro Ser Lys Leu Gly His Lys Leu Asn
```

225          230          235

<210> SEQ ID NO 10
<211> LENGTH: 108
<212> TYPE: PRT
<213> ORGANISM: Homo sapiens

<400> SEQUENCE: 10

Met Lys His Lys Ile Leu His Arg Leu Leu Glu Asp Ser Ser Leu Glu
1               5                   10                  15

Gly Ser Thr Met Lys His Lys Ile Leu His Arg Leu Leu Glu Asp Ser
            20                  25                  30

Ser Leu Glu Met Asp Arg Arg Lys Thr Lys Lys Ile Lys Gly Ile
        35                  40                  45

Gln Gln Ala Thr Ala Gly Met Asp Arg Arg Lys Thr Lys Lys Ile
    50                  55                  60

Lys Gly Ile Gln Gln Ala Thr Ala Gly Met Asp Pro Pro Val Ala Thr
65                  70                  75                  80

Met Val Ser Lys Gly Glu Glu Leu Phe Thr Gly Val Val Pro Ile Leu
                85                  90                  95

Val Glu Leu Asp Gly Asp Val Asn Gly His Lys Phe
            100                 105

<210> SEQ ID NO 11
<211> LENGTH: 255
<212> TYPE: PRT
<213> ORGANISM: Homo sapiens

<400> SEQUENCE: 11

Asp His Arg Ile Glu Ile Leu Asn His Asp Lys Asp Tyr Asn Lys Val
1               5                   10                  15

Thr Val Tyr Glu Ser Ala Val Ala Arg Asn Ser Thr Asp Gly Met Asp
            20                  25                  30

Glu Leu Tyr Lys Glu Phe Ala Thr Met Asn Gln Leu Arg Leu Gln Leu
        35                  40                  45

Gln Gln Arg Leu Gln Gly Gln Gln Leu Ile His Gln Asn Arg Gln
    50                  55                  60

Ala Ile Leu Asn Gln Phe Ala Ala Thr Ala Pro Val Gly Ile Asn Met
65                  70                  75                  80

Arg Ser Gly Met Gln Gln Gln Ile Thr Pro Gln Pro Leu Asn Ala
                85                  90                  95

Gln Met Leu Ala Gln Arg Gln Arg Glu Leu Tyr Ser Gln Gln His Arg
            100                 105                 110

Gln Arg Gln Leu Ile Gln Gln Arg Ala Met Leu Met Arg Gln Gln
        115                 120                 125

Ser Phe Gly Asn Asn Leu Pro Pro Ser Ser Gly Leu Pro Val Gln Met
    130                 135                 140

Gly Asn Pro Arg Leu Pro Gln Gly Ala Pro Gln Phe Pro Tyr Pro
145                 150                 155                 160

Pro Asn Tyr Gly Thr Asn Pro Gly Thr Pro Pro Ala Ser Thr Ser Pro
                165                 170                 175

Phe Ser Gln Leu Ala Ala Asn Pro Glu Ala Ser Leu Ala Asn Arg Asn
            180                 185                 190

Ser Met Val Ser Arg Gly Met Thr Gly Asn Ile Gly Gly Gln Phe Gly
        195                 200                 205

Thr Gly Ile Asn Pro Gln Met Gln Gln Asn Val Phe Gln Tyr Pro Gly

-continued

```
            210                 215                 220
Ala Gly Met Val Pro Gln Gly Glu Ala Asn Phe Ala Pro Ser Leu Ser
225                 230                 235                 240

Pro Gly Ser Ser Met Val Pro Met Pro Ile Gly Ser Pro Pro Val
                245                 250                 255
```

SYSTEMS AND METHODS FOR THE MONITORING OF PROTEIN COMPLEX FORMATION IN CELLS

CROSS REFERENCE TO RELATED APPLICATIONS

The present application is a National Entry Application of PCT application no. PCT/CA2014/051266 filed on Dec. 23, 2014, which itself claims the benefit of U.S. Provisional Application Ser. No. 61/920,070 filed on Dec. 23, 2013. All documents above are incorporated herein by reference in their entirety.

FIELD OF THE INVENTION

The present invention relates to the real-time detection of protein-protein interactions, and more particularly multiprotein complexes, e.g., ternary or quaternary complexes, in living cells.

SEQUENCE LISTING

Pursuant to 37 C.F.R. 1.821(c), the sequence listing submitted on Jun. 22, 2016 as an ASCII compliant text file named 15691_67-seq_listing_ST25.txt, created on Dec. 23, 2014 and having a size of ~14 kilobytes, is hereby incorporated by reference in its entirety.

BACKGROUND OF THE INVENTION

Fluorescence/Förster Resonance Energy Transfer (FRET) and Bioluminescence Resonance Energy Transfer (BRET) both allow real-time detection of protein-protein interactions in intact cells. FRET involves energy transfer between two fluorophores (fluorescent proteins). A donor fluorophore, initially in its electronic excited state, may transfer energy to an acceptor fluorophore through nonradiative dipole-dipole coupling. The efficiency of this energy transfer is inversely proportional to the sixth power of the distance between donor and acceptor making FRET extremely sensitive to small distances. Measurements of FRET efficiency can be used to determine if two fluorophores are within a certain distance of each other. A limitation of FRET is the requirement for external illumination to initiate the fluorescence transfer, which can lead to background noise (autofluorescence, light scattering and/or photoisomerization) due to direct excitation of the acceptor or to photobleaching. Photobleaching is an important drawback when assessing endogenous interactions because it can damage the cells and therefore alter normal interactions between biomolecules.

To avoid this drawback, Bioluminescence Resonance Energy Transfer (or BRET) has been developed. BRET assay technology is based on the efficient resonance energy transfer (RET) between a bioluminescent donor moiety and a fluorescent acceptor moiety. This technique uses a bioluminescent luciferase (typically the luciferase from *Renilla reniformis*) rather than a fluorophore (typically Cyan fluorescent protein (CFP)) to produce an initial photon emission compatible with the fluorescent acceptor (typically yellow fluorescent protein (YFP)).

FRET allows reliable monitoring of sequential transfer between three fluorophores in a three-color or triple-FRET assay, but still suffers from photobleaching of the donor and contaminating cross-excitation problems. Sequential Resonance Energy Transfer (SRET), which combines serially BRET between an initial donor and intermediate acceptor and resonance energy transfer between the intermediate acceptor and a terminal acceptor (FIG. 1B), is based on the same principle using bioluminescence as a source of energy, but is handicapped by a low signal output and high signal cross-contamination. Coupling a protein complementation assay (PCA) to BRET or FRET can also detect ternary complexes. However, PCA imposes greater steric constraints for permissive interactions, slow dissociation of interacting partners due to stable folding of the reconstituted donor and also suffers from low output signal intensity.

As many biomolecules interact in ternary (or higher order complexes), there remains a need for assays that allow for reliable ternary/quaternary complex monitoring.

The present description refers to a number of documents, the content of which is herein incorporated by reference in their entirety.

SUMMARY OF THE INVENTION

Described herein is a bioluminescence resonance energy transfer (BRET) based system, called BRET with Fluorescence enhancement by combined energy transfer (BRETFect), to monitor ternary complex formation in real-time in live cells with high sensitivity and accuracy. As opposed to SRET (in which the energy is transferred from an initial donor (Luc) to an intermediate acceptor (GFP), which in turn transfers the energy to the terminal acceptor (YFP), see FIG. 1B), BRETFect combines energy transfer energy between a luciferase Donor and an Intermediate on one hand and an Acceptor on the other, appropriately chosen to also enable transfer from the Intermediate to the Acceptor while minimizing contaminating signals (see FIG. 5A). This specific energy transfer mechanism was shown to greatly improve sensitivity of detection. The method is broadly applicable to the detection of any protein ternary complex such as those involving nuclear receptors, GPCRs, Receptor Tyrosine Kinase (RTKs), multimeric enzymes or structural proteins. The method of the present invention is also amenable to microscopy or micro-plate reader experiments. It was shown to be sufficiently robust to be amenable to high-throughput screening.

The present invention provides the following items 1 to 54.

1. A biosensor for detecting a ternary protein complex comprising: i. a first protein tagged with a Donor (D) protein, wherein D is a bioluminescent protein (BioI) having an emission spectrum (BioI-Em); ii. a second protein tagged with an Intermediate (I) protein, wherein I is a first Fluorescent protein (FP1) having an excitation spectrum (FP1-Ex) and emission spectrum (FP1-Em); and iii. a third protein tagged with an Acceptor (A) protein, wherein A is a second fluorescent protein (FP2) having an excitation spectrum (FP2-Ex) and an emission spectrum (FP2-Em); wherein a) the FP1-Ex overlaps with the BioI-Em and overlaps minimally with the FP2-Ex; b) the FP1-Em overlaps with the FP2-Ex; c) the FP2-Ex overlaps with the BioI-Em; and d) the FP2-Em has a longer wavelength than the FP1-Em.

2. A biosensor for the detection of a quaternary protein complex comprising: i. a first protein tagged with a first portion of a Donor protein (D1), wherein D1 is a first bioluminescent protein portion (BioIP1), ii. a second protein tagged with a second portion of a Donor protein (D2), wherein D2 is a second bioluminescent protein portion (BioIP2), wherein interaction between said first and second proteins brings said BioIP1 and BioIP2 in close enough proximity to form a functional bioluminescent protein (BioI) having an emission spectrum Em; iii. a third protein tagged with an Intermediate (I) protein, wherein I is a first Fluorescent protein (FP1) having an excitation spectrum (FP1-Ex) and emission spectrum (FP1-Em); and iv. a fourth protein tagged with an Acceptor (A) protein, wherein A is a second fluorescent protein (FP2) having an excitation spectrum (FP2-Ex) and an emission spectrum (FP2-Em); wherein a) the FP1-Ex overlaps with the Biol-Em and overlaps minimally with the FP2-Ex; b) the FP1-Em overlaps with the FP2-Ex; c) The FP2-Ex overlaps with the Biol-Em; and d) the FP2-Em has a longer wavelength than the FP1-Em.

3. The biosensor of item 1 or 2, wherein the bioluminescent protein is a luciferase, preferably a *Renilla* Luciferase (RLuc).

4. The biosensor of any one of items 1-3, wherein FP1 is mTFP1 or mTagBFP2 fluorescent protein.

5. The biosensor of any one of items 1-4, wherein FP2 is Venus, Topaz or mTFP1 fluorescent protein.

6. The biosensor of any one of items 1-5, further comprising a luciferase substrate.

7. The biosensor of item 6, wherein the bioluminescent protein substrate is a coelenterazine.

8. The biosensor of item 7, wherein the coelenterazine is coelenterazine H or coelenterazine-400a.

9. The biosensor of any one of items 1-8, wherein said first, second, third or fourth protein is a nuclear receptor protein or a fragment thereof.

10. The biosensor of item 9, wherein at least two of said first, second, third and/or fourth proteins are nuclear receptor proteins or fragments thereof.

11. The biosensor of item 10, wherein two of said first, second, third and/or fourth proteins are nuclear receptor proteins or fragments thereof.

12. The biosensor of item 11, wherein said two nuclear receptor proteins or fragments thereof are identical.

13. The biosensor of item 11, wherein said two nuclear receptor proteins or fragments thereof are different.

14. The biosensor of any one of items 9 to 13, wherein the nuclear receptor is an Estrogen receptor (ER), a Retinoic acid receptor, Androgen receptor (AR), Glucocorticoid receptor (GR) or Progesterone receptor (PR).

15. The biosensor of item 14, wherein the nuclear receptor is a nuclear estrogen receptor or a retinoic acid receptor.

16. The biosensor of any one of items 9 to 15, wherein at least one of said first, second, third or fourth protein is a nuclear receptor coactivator protein or a nuclear receptor-binding fragment thereof.

17. The biosensor of item 16, wherein said nuclear receptor coactivator protein is SRC1 or SRC2.

18. The biosensor of any one of items 1-8, wherein at least one of said first, second, third or fourth protein is a G protein coupled receptor (GPCR) protein or a fragment thereof.

19. The biosensor of item 18, wherein at least two of said first, second, third and/or fourth proteins are GPCR proteins or fragments thereof.

20. The biosensor of item 19, wherein two of said first, second, third and/or fourth proteins are GPCR proteins or fragments thereof.

21. The biosensor of item 20, wherein said two GPCR proteins or fragments thereof are identical.

22. The biosensor of item 20, wherein said two GPCR proteins or fragments thereof are different.

23. The biosensor of any one of items 18-22, wherein at least one of said first, second, third or fourth protein is a G protein subunit or a fragment thereof.

24. The biosensor of any one of items 18-22, wherein two of said first, second, third and/or fourth proteins are two different G protein subunits or fragments thereof.

25. The biosensor of item 23 or 24, wherein said G protein subunit(s) is/are a Gα subunit, a Gγ subunit and/or a Gβ subunit.

26. The biosensor of any one of items 18-23, wherein at least one of said first, second, third or fourth protein is a βarrestin protein or a fragment thereof.

27. The biosensor of any one of items 18-26, wherein at least one of said first, second, third or fourth protein is a pleckstrin homology (PH) domain-containing protein.

28. The biosensor of item 27, wherein said PH domain-containing protein is a G protein-coupled receptor kinase (GRK) protein or a PH domain of a GRK.

29. The biosensor of any one of items 18-23, wherein at least one of said first, second, third or fourth protein is a regulator of G-protein signalling (RGS), an activator of G-protein signalling (AGS), or a resistance to inhibitors of cholinesterase 8 protein (Ric-8), or any fragment thereof.

30. The biosensor of any one of items 1-29, further comprising a cell expressing components (i), (ii) and (iii).

31. A method for the detection of a ternary protein complex, the method comprising:

A) providing: i. a first protein tagged with a Donor (D) protein, wherein D is a bioluminescent protein (Biol) having an emission spectrum (Biol-Em); ii. a second protein tagged with an Intermediate (I) protein, wherein I is a first Fluorescent protein (FP1) having an excitation spectrum (FP1-Ex) and emission spectrum (FP1-Em); and iii. a third protein tagged with an Acceptor (A) protein, wherein A is a second fluorescent protein (FP2) having an excitation spectrum (FP2-Ex) and an emission spectrum (FP2-Em);

wherein a) the FP1-Ex overlaps with the Biol-Em and overlaps minimally with the FP2-Ex; b) the FP1-Em overlaps with the FP2-Ex; c) the FP2-Ex overlaps with the Biol-Em; and d) the FP2-Em has a longer wavelength than the FP1-Em; and B) contacting the D protein with a bioluminescent protein substrate; and C) detecting Bioluminescence Resonance Energy Transfer (BRET) with Fluorescence enhancement by combined energy transfer (BRETFect) signal; wherein the detection of a BRETFect signal is indicative that a complex is formed.

32. A method for the detection of a quaternary protein complex, the method comprising:

A) providing: i. a first protein tagged with a first portion of a Donor protein (D1), wherein D1 is a first bioluminescent protein portion (BiolP1) ii. a second protein tagged with a second portion of a Donor protein (D2), wherein D2 is a second bioluminescent protein portion (BiolP2), wherein interaction between said first and second proteins brings said BiolP1 and BiolP2 in close enough proximity to form a functional bioluminescent protein (Biol) having an emission spectrum Em; iii. a third protein tagged with an Intermediate (I) protein, wherein I is a first Fluorescent protein (FP1) having an excitation spectrum (FP1-Ex) and emission spectrum (FP1-Em); and iv. a fourth protein tagged with an Acceptor (A) protein, wherein A is a second fluorescent protein (FP2) having an excitation spectrum (FP2-Ex) and an emission spectrum (FP2-Em);

wherein a) the FP1-Ex overlaps with the Biol-Em and overlaps minimally with the FP2-Ex; b) the FP1-Em overlaps with the FP2-Ex; c) The FP2-Ex overlaps with the Biol-Em; and d) the FP2-Em has a longer wavelength than the FP1-Em; and B) contacting the D1 and/or D2 protein with a bioluminescent protein substrate; and C) detecting Bioluminescence Resonance Energy Transfer Forster enhanced by simultaneous transfer (BRETFect) signal; wherein the detection of a BRETFect signal is indicative that a quaternary complex is formed.

33. The method of item 31 or 32, wherein the bioluminescent protein is a luciferase, preferably a *Renilla* Luciferase (RLuc).

34. The method of any one of item 31-33, wherein FP1 is mTFP1 or mTagBFP2 fluorescent protein.

35. The method of any one of items 31-34, wherein FP2 is Venus, Topaz or mTFP1 fluorescent protein.

36. The method of any one of items 31-35, wherein the bioluminescent protein substrate is a coelenterazine.

37. The method of item 36, wherein the coelenterazine is coelenterazine H or coelenterazine-400a.

38. The method of any one of items 31-37, wherein the detecting step in C) comprises detecting the D emission at about 485 nm and the A emission at between about 530 and 550 nm.

39. The method of item 38, wherein the A emission is detected at about 550 nm.

40. The method of any one of items 31-39, wherein said first, second, third and fourth proteins are as defined in any one of items 9 to 29.

41. A method for determining whether an agent modulates the formation of a ternary or quaternary protein complex comprising performing the method of any one of items 31-40 in the presence and in the absence of said agent, wherein an increase in BRETFect signal in the presence of the agent relative to the absence thereof is indicative that the agent promotes the formation of the ternary or quaternary complex, and wherein a reduction in BRETFect signal in the presence of the agent relative to in the absence thereof is indicative that the agent inhibits the formation of the ternary or quaternary complex.

42. A kit comprising:
one or more vectors for expressing: i. a first protein tagged with a Donor (D) protein, wherein D is a bioluminescent protein (Biol) having an emission spectrum (Biol-Em); ii. a second protein tagged with an Intermediate (I) protein, wherein I is a first Fluorescent protein (FP1) having an excitation spectrum (FP1-Ex) and emission spectrum (FP1-Em); iii. a third protein tagged with an Acceptor (A) protein, wherein A is a second fluorescent protein (FP2) having an excitation spectrum (FP2-Ex) and an emission spectrum (FP2-Em); wherein
a) the FP1-Ex overlaps with the Biol-Em and does not significantly overlaps with the FP2-Ex; b) the FP1-Em overlaps with FP2-Ex; c) the FP2-Ex overlaps with the Biol-Em; and d) the FP2-Em has a longer wavelength than the FP1-Em.

43. A kit comprising:
one or more vectors for expressing: i. a first protein tagged with a first portion of a Donor protein (D1), wherein D1 is a first bioluminescent protein portion (BiolP1); ii. a second protein tagged with a second portion of a Donor protein (D2), wherein D2 is a second bioluminescent protein portion (BiolP2); iii. a third protein tagged with an Intermediate (I) protein, wherein I is a first Fluorescent protein (FP1) having an excitation spectrum (FP1-Ex) and emission spectrum (FP1-Em); iv. a fourth protein tagged with an Acceptor (A) protein, wherein A is a second fluorescent protein (FP2) having an excitation spectrum (FP2-Ex) and an emission spectrum (FP2-Em); wherein said BiolP1 and BiolP2 can form a functional bioluminescent protein (Biol) having an emission spectrum Em if brought in close enough proximity, and wherein
a) the FP1-Ex overlaps with the Biol-Em and does not significantly overlaps with the FP2-Ex; b) the FP1-Em overlaps with FP2-Ex; c) the FP2-Ex overlaps with the Biol-Em; and d) the FP2-Em has a longer wavelength than the FP1-Em.

44. The kit of item 42, wherein said kit comprises one or more vectors comprising a nucleic acid encoding said bioluminescent protein; a nucleic acid encoding said FP1; and a nucleic acid encoding said FP2.

45. The kit of item 43, wherein said kit comprises one or more vectors comprising a nucleic acid encoding said BiolP1; a nucleic acid encoding said BiolP2; a nucleic acid encoding said FP1; and a nucleic acid encoding said FP2.

46. The kit of any one of items 42 to 45, wherein said kit comprises one vector.

47. The kit of item 42 or 44, wherein said kit comprises a first vector for expressing said first protein tagged with Biol, a second vector for expressing said second protein tagged with FP1 and a third vector for expressing said third protein tagged with FP2.

48. The kit of item 43 or 45, wherein said kit comprises a first vector for expressing said first protein tagged with BiolP1, a second vector for expressing said second protein tagged with BiolP2; a third vector for expressing said third protein tagged with FP1 and a third vector for expressing said fourth protein tagged with FP2.

49. The kit of any one of items 42-48, wherein the bioluminescent protein is luciferase, preferably *Renilla* Luciferase.

50. The kit of any one of items 42-49, wherein the FP1 is mTFP1 or mTagBFP2 fluorescent protein.

51. The kit of any one of items 42-50, wherein the FP2 is Venus, Topaz or mTFP1 fluorescent protein.

52. The kit of any one of item 42-51, further comprising a bioluminescent protein substrate.

53. The kit of item 52, wherein the bioluminescent protein substrate is coelenterazine H or coelenterazine 400a.

54. A cell expressing components (i), (ii) and (iii) defined in any one of items 1-29.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 3—Absorption and emission spectra of different donors and acceptors used in the different components of BRETFect. (FIG. 3A) Spectra from typical BRET1 chromophores, RLucII and eYFP (Venus). (FIG. 3B) Chart showing the overlap of mTFP1 absorption and emission spectra overlaid with RLucII emission. (FIG. 3C) Overlay of spectra for the three chromophores used in the BRETFect assay (FIG. 3D) Graph showing the detection channels in the BRETFect assay and the emission captured from potential Intermediate mTFP1 and GFP2 and the donor RLucII. Relative light units (RLU) are calculated as a fraction of the maximal value recorded in each condition which is set at 1.00.

FIG. 4—BRETFect monitors ternary complex formation in live cells.

FIG. 5—BRETFect monitors CoApep recruitment to ERα dimers.

FIG. 8—ERβ requires ERα for efficient AF1ID interaction and dimer complex SUMOylation in response to ligand treatment.

FIG. 10—Demonstrating activation of ERα-ERβ heterodimers by selective ligands using BRETFect. (FIG. 10A, C, E) Effect of ERα specific ligand PPT on ERα and ERβ homo and heterodimers. (FIG. 10B, D, F) Effect of ERβ selective ligand DPN on ERα and ERβ homo and heterodimers. (FIG. 10A-B) Effect of PPT (FIG. 10A) and DPN (FIG. 10B) compared to E2 on ERα (FIG. 10A) and ERβ (FIG. 10B) homodimers. Displayed graphs were prepared from 3 biological replicates and error bars represent the SEM from 3 technical replicates.

DETAILED DESCRIPTION OF ILLUSTRATIVE EMBODIMENTS

Figure 1A:
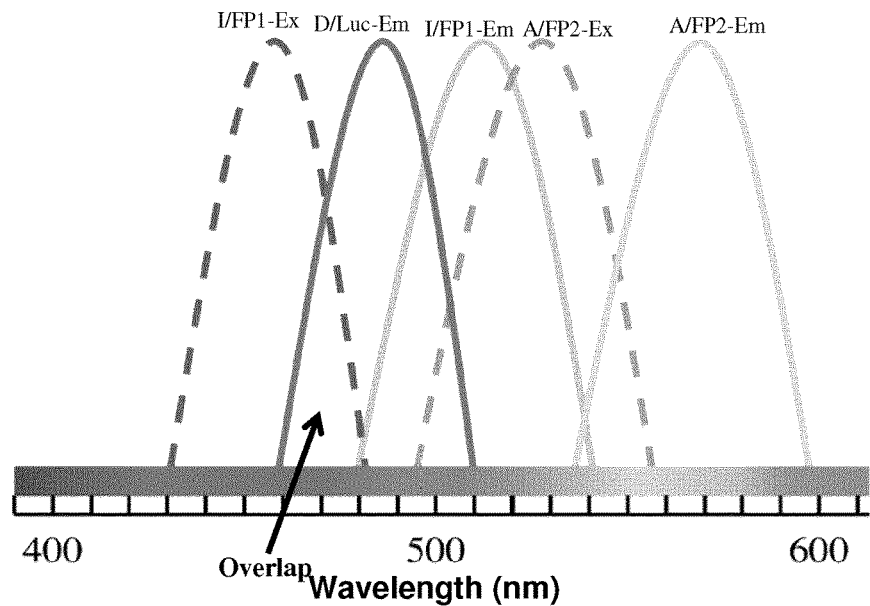
FIG. 1A exemplifies how the spectra of the three partners in BRETFect: Donor (D/RLuc), Intermediate (I/FP1) and Acceptor (A/FP2) could be distributed along the visible light spectrum. Dotted lines represent excitation spectrum. Solid lines represent emission spectrum.

Unless specifically defined, the terms used in the present application have the meanings that one of ordinary skill in the art would ascribe to them.

In order to provide a clear and consistent understanding of the terms used in the present specification, a number of definitions are provided below.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

BRETFect Biosensors/Assays

Because of the lack of reliable methods for detecting multiprotein complexes (ternary or quaternary) complexes in living cells with sufficient output signal and specificity, the present inventors have developed a new bioluminescence resonance energy transfer (BRET) based system, called BRET-fluorescence enhanced by combined energy transfer (BRETFect), to monitor high order (e.g., ternary, quaternary) complex formation in live cells with high sensitivity and accuracy.

The BRETFect biosensor/method relies on parallel/combined Förster Resonance Energy Transfer mechanisms between at least three molecules: i) a Donor protein (ID or D) i.e., a bioluminescent protein (Biol), such as a luciferase (Luc); ii) an Intermediate protein (IA or I), i.e. a first Fluorescent Protein (FP1) and an Acceptor protein (TA or A), i.e. a second fluorescent protein (FP2).

Thus, the present invention relates to a biosensor for detecting a ternary protein complex comprising:
  i. a first protein tagged with a Donor (D) protein, wherein D is a bioluminescent protein such as a luciferase (Luc), having an emission spectrum (Biol-Em);
  ii. a second protein tagged with an Intermediate (I) protein, wherein I is a first Fluorescent protein (FP1) having an excitation spectrum (FP1-Ex) and emission spectrum (FP1-Em); and
  iii. a third protein tagged with an Acceptor (A) protein, wherein A is a second fluorescent protein (FP2) having an excitation spectrum (FP2-Ex) and an emission spectrum (FP2-Em);
  wherein
  a) the FP1-Ex overlaps with the Biol-Em and overlaps minimally (e.g., does not significantly overlap) with the FP2-Ex (e.g., their peaks of excitation do not coincide and/or the overlap in the areas under the curve for their Ex spectra should ideally be lower than 35%, preferably lower than 30, 20 or 10%);
  b) the FP1-Em overlaps with the FP2-Ex;
  c) the FP2-Ex overlaps with the Biol-Em; and
  d) the FP2-Em has a longer wavelength than the FP1-Em.

The present invention also relates to a method for the detection of a ternary protein complex, the method comprising:
  A) providing:
    i. a first protein tagged with a Donor (D) protein, wherein D is a bioluminescent protein (Biol) having an emission spectrum (Biol-Em);
    ii. a second protein tagged with an Intermediate (I) protein, wherein I is a first Fluorescent protein (FP1)

having an excitation spectrum (FP1-Ex) and emission spectrum (FP1-Em); and iii. a third protein tagged with an Acceptor (A) protein, wherein A is a second fluorescent protein (FP2) having an excitation spectrum (FP2-Ex) and an emission spectrum (FP2-Em);

wherein a) the FP1-Ex overlaps with the BioI-Em and overlaps minimally (e.g., does not significantly overlap) with the FP2-Ex (e.g., their peaks of excitation do not coincide and/or the overlap in the areas under the curve for their Ex spectra should ideally be lower than 35%, preferably lower than 30, 20 or 10%);

b) the FP1-Em overlaps with the FP2-Ex;

c) the FP2-Ex overlaps with the BioI-Em; and d) the FP2-Em has a longer wavelength than the FP1-Em;

and

B) contacting the D protein with a bioluminescent protein (e.g., luciferase) substrate; and C) detecting the BRET-fluorescence enhanced by combined energy transfer (BRETFect) signal; wherein the detection of a BRETFect signal is indicative that a complex is formed.

The term "ternary complex" is used herein to refer to a complex comprising 3 or more proteins, which may be the same or different. The biosensor/method described herein may thus be used to detect the formation of a trimer (a complex formed by 3 proteins), or an interaction (direct or indirect) between 3 proteins within a larger protein complex, i.e. comprising 4, 5, 6 or more proteins.

Although the BRETFect assay described herein allows for the highly sensitive detection of ternary complexes, it can further be modified/adapted for quaternary complex detection by combining it with a protein complementation assay (PCA) (see, e.g., Rebois, R. V., et al., *Methods,* 2008. 45(3): p. 214-8). PCA is a method for the identification of protein—protein interactions in biological systems. In the PCA, the proteins of interest ("Bait" and "Prey") are each covalently linked to incomplete fragments of a third protein (e.g. DHFR), which acts as a "reporter". Interaction between the "bait" and the "prey" proteins brings the fragments of the "reporter" protein in close enough proximity to allow them to form a functional reporter protein whose activity can be measured. This principle can be applied to many different "reporter" proteins. Any protein that can be split into two parts and reconstituted non-covalently may be used in a PCA. The two parts are brought together by two interacting proteins fused to them ("bait" and "prey"). Usually enzymes which confer resistance to antibiotics, such as Dihydrofolate reductase or Beta-lactamase, or proteins that give colorimetric or fluorescent signals are used as reporters. When fluorescent proteins are reconstituted, the PCA is called Bimolecular fluorescence complementation assay. The most popular PCAs utilize split versions of the following proteins: Dihydrofolate reductase (DHFR), Beta-lactamase, Yeast Gal4 (as in the classical yeast two-hybrid system), Luciferase, Split TEV (Tobacco etch virus protease), Ubiquitin, GFP (split-GFP), LacZ (beta-galactosidase). In an embodiment, the reporter protein is a luciferase and the biosensor comprises a split version of the luciferase, i.e. two fragments/portions of the luciferase that can generate a functional luciferase when the two fragments/portions are brought in close enough proximity. Fragments of luciferase suitable for PCA are disclosed, for example, in Luker and Luker, *Luciferase Protein Complementation Assays for Bioluminescence Imaging of Cells and Mice*, Molecular Imaging, Methods in Molecular Biology 680, Chapter 2, and include those depicted in the Table II below.

TABLE II

Examples of luciferase fragments suitable for PCA

| Luciferase | Fragment 1 (residues) | Fragment 2 (residues) |
| --- | --- | --- |
| Firefly luciferase | 2-416 | 398-550 |
| Firefly luciferase | 2-398 | 394-550 |
| *Renilla* luciferase | 1-229 | 230-311 |
| *Renilla* luciferase | 1-110 | 111-311 |
| *Gaussia* luciferase | 1-93 | 94-169 |

The BRETFect biosensor/method of the present invention may thus be conveniently adapted to detect quaternary complexes by including a PCA element. For example, one part of the luciferase enzyme could be coupled to a first interacting partner (ID) and the second part to a $2^{nd}$ interacting partner. FP1 and FP2 would be coupled to $3^{rd}$ and $4^{th}$ interacting partners. Upon interaction between the first and $2^{nd}$ interacting partners, a functional luciferase would be recreated, thereby enabling the transfer to the intermediate and terminal acceptors. Certain nuclear receptors are known to form multimers of higher order than dimers. To monitor activity of higher order complexes, nuclear receptor 1 (NR1) and NR2 can be tagged with half luciferases, NR3 with FP1 (e.g., mTFP1) and a cofactor with FP2 (e.g., eYFP).

Thus, the present invention further relates to a biosensor for the detection of a quaternary protein complex comprising the elements defined above, wherein one of BioI, FP1 or FP2 is divided in two parts/portions that can generate a functional protein when brought in close enough proximity, and the biosensor comprises an additional tagged protein.

Accordingly, in another aspect, the present invention relates to a biosensor for the detection of a quaternary protein complex comprising:

i. a first protein tagged with a first portion of a Donor protein (D1), wherein D1 is a first bioluminescent protein portion (BioIP1);

ii. a second protein tagged with a second portion of a Donor protein (D2), wherein D2 is a second bioluminescent protein portion (BioIP2), wherein interaction between said first and second proteins brings said BioIP1 and BioIP2 in close enough proximity to form a functional bioluminescent protein (BioI) having an emission spectrum Em;

iii. a third protein tagged with an Intermediate (I) protein, wherein I is a first Fluorescent protein (FP1) having an excitation spectrum (FP1-Ex) and emission spectrum (FP1-Em); and iv. a fourth protein tagged with an Acceptor (A) protein, wherein A is a second fluorescent protein (FP2) having an excitation spectrum (FP2-Ex) and an emission spectrum (FP2-Em); wherein BioI-Em, FP1-Ex, FP1-Em, FP2-Ex and FP2-Em are as defined above.

In another aspect, the present invention relates to a method for the detection of a quaternary protein complex, the method comprising:

A) providing:

i. a first protein tagged with a first portion of a Donor protein (D1), wherein D1 is a first bioluminescent protein portion (BioIP1)

ii. a second protein tagged with a second portion of a Donor protein (D2), wherein D2 is a second bioluminescent protein portion (BioIP2), wherein interaction between said first and second proteins brings said BioIP1 and BioIP2 in close enough proximity to form a functional bioluminescent protein (BioI) having an emission spectrum Em;

iii. a third protein tagged with an Intermediate (I) protein, wherein I is a first Fluorescent protein (FP1) having an excitation spectrum (FP1-Ex) and emission spectrum (FP1-Em); and iv. a fourth protein tagged with an Acceptor (A) protein, wherein A is a second fluorescent protein (FP2) having an excitation spectrum (FP2-Ex) and an emission spectrum (FP2-Em);

wherein a) the FP1-Ex overlaps with the BioI-Em and overlaps minimally with the FP2-Ex;

b) the FP1-Em overlaps with the FP2-Ex;

c) The FP2-Ex overlaps with the BioI-Em; and d) The FP2-Em has a longer wavelength than the FP1-Em;

and

B) contacting the D1 and/or D2 protein with a bioluminescent protein (e.g., luciferase) substrate; and C) detecting Bioluminescence Resonance Energy Transfer Forster enhanced by simultaneous transfer (BRET-Fect) signal; wherein the detection of a BRETFect signal is indicative that a quaternary complex is formed.

In an embodiment, FP1-Ex and FP2-Ex are such that FP1 and FP2 are excited by a different portion of the BioI-Em spectrum, i.e. the transfers from D to I and A are complementary rather than competitive. In an embodiment, FP1-Ex overlaps with the lower end (i.e. lower wavelengths) of the BioI-Em spectrum and FP2-Ex overlaps with the higher end (i.e. higher wavelengths) of the BioI-Em spectrum.

The term "quaternary complex" is used herein to refer to a complex comprising 4 or more proteins, which may be the same or different. The biosensor/method described herein may thus be used to detect the formation of a complex formed by 4 proteins, or an interaction (direct or indirect) between 4 proteins within a larger protein complex, i.e. comprising 5, 6, 7 or more proteins.

As used herein, the terms first, second and third proteins are meant to refer to the three interacting components in a ternary complex that is to be detected in accordance with the biosensor/method described. As used herein, the terms first, second, third and fourth proteins are meant to refer to the four interacting components in a quaternary complex that is to be detected in accordance with the biosensor/method described.

As used herein, the terms "first Donor" (D1) and "second Donor" (D2) are meant to refer to 2 complementary parts of the donor protein that is suitable to generate/reconstitute a functional or active donor protein when brought in close proximity by direct or indirect interaction between the proteins to which they are bound. D more specifically refers to a bioluminescent enzyme, for example a luciferase. The term "Intermediate" (I) refers to a first fluorescent protein (FP1), which following excitation by the D, transfers part of its energy to the Acceptor (A). The "Acceptor" (A) is a fluorescent protein (FP2) that is different from FP1 (and which may be excited by the energy emitted by both D and I).

Thus, the first, second and third proteins (or first, second, third and fourth proteins) may be the same protein/peptide (to detect a homotrimer or "homoquatermer" of a protein, which may or may not be in a larger protein complex), 3 or 4 different proteins (to detect a heterotrimer or "heteroquatermer", which may or may not be in a larger protein complex), or combinations thereof (e.g., to detect a complex comprising 2 or 3 identical proteins and a $3^{rd}$ (or $3^{rd}$ and $4^{th}$) distinct protein(s)). In an embodiment, the first, second and third proteins (or first, second, third and fourth proteins) are identical. In another embodiment, the first, second and third proteins (or first, second, third and fourth proteins) are all different. In another embodiment, the first and second proteins are identical and the third protein is different. In another embodiment, the first and third proteins are identical and the second protein is different. In another embodiment, the second and third proteins are identical and the first protein is different. It should be understood that for a given ternary complex, the proteins fused to the bioluminescent enzyme, first fluorescent protein and second fluorescent protein (D, I and A, respectively) may be interchanged. For example, for detecting the formation of a ternary complex comprising protein1, protein2 and protein3, several configurations are possible: (1) protein1 is tagged with D, protein2 is tagged with I and protein3 is tagged with A; (2) protein1 is tagged with D, protein2 is tagged with A and protein3 is tagged with I; (3) protein1 is tagged with I, protein2 is tagged with D and protein3 is tagged with A; (4) protein1 is tagged with I, protein2 is tagged with A and protein3 is tagged with D; (5) protein1 is tagged with A, protein2 is tagged with I and protein3 is tagged with D; or (6) protein1 is tagged with A, protein2 is tagged with D and protein3 is tagged with I.

The biosensor/method is based on the simultaneous energy transfer between a bioluminescent protein (e.g., luciferase) donor and intermediate and terminal acceptors, appropriately chosen to also enable transfer from the intermediate to terminal acceptor while minimizing contaminating signals. This specific energy transfer mechanism was shown to greatly improve sensitivity of detection.

As used herein, the term "bioluminescent protein" refers to a class of enzymes that are able to catalyze (e.g., oxidize) a substrate, which in turn emits fluorescent light upon catalysis (oxidation). Examples of bioluminescent proteins include lumazin, obelin, aequorin and luciferase (native and functional variants thereof). In an embodiment, the bioluminescent protein is luciferase.

As used herein, the term "luciferase" refers to the class of oxidative enzymes used in bioluminescence and which is distinct from a photoprotein. One example is the firefly luciferase (EC 1.13.12.7) from the firefly *Photinus pyralis* (*P. pyralis* luciferase). Several recombinant luciferases from several other species including luciferase from *Renilla reniformis* (GENBANK: AAA29804) and variants thereof (e.g., a stable variant of *Renilla* Luciferase e.g., RlucII (GENBANK: AAV52877.1), Rluc8 (GENBANK: EF446136.1) and *Gaussia* Luciferase (Gluc, GENBANK: AAG54095.1) are also commercially available. Any luciferase can be used in accordance with the present invention as long as it can metabolize a luciferase substrate such as luciferins. Luciferins are a class of light-emitting heterocyclic compounds that are oxidized in the presence of luciferase to produce oxyluciferin and energy in the form of light. Non-limiting examples of luciferins include D-luciferin, imidazopyrazinone-based compounds such as coelenterazine (coelenterazine 400a (DeepBlueC™) and coelenterazine H), ViviRen™ (from Promega®), Latia luciferin ((E)-2-methyl-4-(2,6,6-trimethyl-1-cyclohex-1-yl)-1-buten-1-ol formate), bacterial luciferin, Dinoflagellate luciferin, etc. Luciferase substrates may have slightly different emission spectra and will thus be selected to favor the optimal energy transfer to the initial and terminal acceptors. In an embodiment, the luciferase is wild-type (or native) *Renilla* Lucificerase. In an embodiment, the luciferase is a variant of *Renilla* luciferase, e.g., Rluc8 or RLucII. In a specific embodiment the luciferase is RLucII and the luciferin is coelenterazine H.

As used herein, the term "fluorescent protein" refers to any protein which becomes fluorescent upon excitation at an appropriate wavelength. A broad range of fluorescent proteins have been developed that feature fluorescence emission spectral profiles spanning almost the entire visible light spectrum. Non-limiting examples of green Fluorescent Protein include EGFP, Emerald, Superfolder GFP, Azami Green, mWasabi, TagGFP, TurboGFP, AcGFP, ZsGreen and T-Sapphire. Non-limiting Examples of blue fluorescent protein include EBFP, EBFP2, Azurite and mTagBFP. Non-limiting examples of Cyan Fluorescent proteins include ECFP, mECFP, Cerulean, mTurquoise, CyPet, AmCyan1, Midori-Ishi Cyan, TagCFP, mTFP1 (Teal). Non-limiting examples of Yellow fluorescent proteins include EYFP, Topaz, Venus, mVenus, mCitrine, YPet, TagYFP, PhiYFP, ZsYellow1 and mBanana. Non-limiting Examples of orange fluorescent proteins include Kusabira Orange, Kusabira Orange2, mOrange, mOrange2, dTomato, dTomato-Tandem, TagRFP, DsRed, DsRed2, DsRed-Express (T1), DsRed-Monomer and mTangerine. Non-limiting Examples of red fluorescent porteins include mRuby, mApple, mStrawberry, AsRed2, mRFP1, JRed, mCherry, HcRed1, mRaspberry, dKeima-Tandem, HcRed-Tandem, mPlum and AQ143.

The bioluminescent protein and fluorescent proteins are covalently attached to the first, second and third proteins. In an embodiment, the bioluminescent protein and fluorescent proteins forms a fusion protein with the first, second and third proteins. The bioluminescent protein and/or fluorescent proteins may be fused N-terminal, within, or C-terminal relative to first, second and/or third proteins. In embodiments, the bioluminescent protein and/or fluorescent proteins may be covalently linked to the first, second and/or third proteins either directly (e.g., through a peptide bond) or "indirectly" via a suitable linker moiety, e.g., a linker of one or more amino acids (e.g., a polyglycine linker) or another type of chemical linker (e.g., a carbohydrate linker, a lipid linker, a fatty acid linker, a polyether linker, PEG, etc. In an embodiment, one or more additional domain(s) may be inserted before (N-terminal), between or after (C-terminal) the bioluminescent-fluorescent proteins and the first, second and/or third proteins.

FIG. 1A exemplifies how the spectra of the three-partner combination (luciferase (Luc), FP1 and FP2) could be distributed along the visible light spectrum. It should be noted that Luc-Emission could peak at shorter wavelength than FP1-Ex as long as the other conditions defined herein are met and this could also be applied to other spectral peaks such as FP1-EM and FP2-Ex. Closely placed Luc emission and FP1 emission peaks enables monitoring of both emissions within a single detection window but spectral unmixing can be applied if that is not the case.

Any combination of bioluminescent protein (e.g., luciferase) and fluorescent proteins may be used in accordance with the present invention as long as the requirements/criteria defined herein are met. In embodiments, the excitation spectrum of I (FP1-Ex) overlaps part of the Luc (D) emission spectrum (Luc-Em) and overlaps minimally with FP2 excitation spectrum (FP2-Ex). Also, the emission spectrum of I (FP1-Em) overlaps part of the A excitation spectrum (FP2-ex), and optimally its peak should be closer to that of the Luc-Em spectrum than to that of the FP2-em. As for the A, its excitation spectrum overlaps part of the D (Luc) emission spectrum and its emission spectrum is red-shifted (longer wavelength) from the I (FP1) emission spectrum, allowing for selective monitoring of FP2 emission.

Several bioluminescent and fluorescent proteins and their excitation and emission spectra are known in the art and can thus be used to identify a suitable combination of bioluminescent protein (e.g., luciferase), FP1 and FP2 (see Table I below). The Fluorescent proteins selected (FP1 and FP2) should not substantially interact to form homodimers or heterodimers or multimers under the experimental conditions used for the BRETFect assay. One representative suitable combination is *Renilla* Luciferase as the Donor (D), mTPF1 fluorescent protein as the Intermediate (I) and Venus fluorescent protein as the Acceptor (A). Another suitable combination is *Renilla* Luciferase (RLucII-coel400) as the Luciferase (D), mtagBFP2 (PDB) as the I and mTFP1 as the A (with measures at 400 and 530 nm). As luciferase substrates may have slightly different emission spectrum, the luciferase substrate is preferably selected to optimize energy transfer between the luciferase and intermediate and terminal acceptors.

TABLE I

Examples of Fluorescent proteins and their properties:

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| Emerald | 487 | 509 | 57,500 | 0.68 | Monomer* | 116 |
| Superfolder GFP | 485 | 510 | 83,300 | 0.65 | Monomer* | 160 |
| Azami Green | 492 | 505 | 55,000 | 0.74 | Monomer | 121 |
| mWasabi | 493 | 509 | 70,000 | 0.80 | Monomer | 167 |
| TagGFP | 482 | 505 | 58,200 | 0.59 | Monomer* | 110 |
| TurboGFP | 482 | 502 | 70,000 | 0.53 | Dimer | 102 |
| AcGFP | 480 | 505 | 50,000 | 0.55 | Monomer* | 82 |
| ZsGreen | 493 | 505 | 43,000 | 0.91 | Tetramer | 117 |
| T-Sapphire | 399 | 511 | 44,000 | 0.60 | Monomer* | 79 |
| Blue Fluorescent Proteins | | | | | | |
| EBFP | 383 | 445 | 29,000 | 0.31 | Monomer* | 27 |
| EBFP2 | 383 | 448 | 32,000 | 0.56 | Monomer* | 53 |

TABLE I-continued

Examples of Fluorescent proteins and their properties:

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| Azurite | 384 | 450 | 26,200 | 0.55 | Monomer* | 43 |
| mTagBFP/BFP2 | 399 | 456 | 52,000 | 0.63 | Monomer | 98 |
| Cyan Fluorescent Proteins | | | | | | |
| ECFP | 439 | 476 | 32,500 | 0.40 | Monomer* | 39 |
| mECFP | 433 | 475 | 32,500 | 0.40 | Monomer | 39 |
| Cerulean | 433 | 475 | 43,000 | 0.62 | Monomer* | 79 |
| mTurquoise | 434 | 474 | 30,000 | 0.84 | Monomer* | 75 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| TagCFP | 458 | 480 | 37,000 | 0.57 | Monomer | 63 |
| mTFP1 (Teal) | 462 | 492 | 64,000 | 0.85 | Monomer | 162 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| TagYFP | 508 | 524 | 64,000 | 0.60 | Monomer | 118 |
| PhiYFP | 525 | 537 | 124,000 | 0.39 | Monomer* | 144 |
| ZsYellow1 | 529 | 539 | 20,200 | 0.42 | Tetramer | 25 |
| mBanana | 540 | 553 | 6,000 | 0.7 | Monomer | 13 |
| Orange Fluorescent Proteins | | | | | | |
| Kusabira Orange | 548 | 559 | 51,600 | 0.60 | Monomer | 92 |
| Kusabira Orange2 | 551 | 565 | 63,800 | 0.62 | Monomer | 118 |
| mOrange | 548 | 562 | 71,000 | 0.69 | Monomer | 146 |
| mOrange2 | 549 | 565 | 58,000 | 0.60 | Monomer | 104 |
| dTomato | 554 | 581 | 69,000 | 0.69 | Dimer | 142 |
| dTomato-Tandem | 554 | 581 | 138,000 | 0.69 | Monomer | 283 |
| TagRFP | 555 | 584 | 100,000 | 0.48 | Monomer | 142 |
| TagRFP-T | 555 | 584 | 81,000 | 0.41 | Monomer | 99 |
| DsRed | 558 | 583 | 75,000 | 0.79 | Tetramer | 176 |
| DsRed2 | 563 | 582 | 43,800 | 0.55 | Tetramer | 72 |
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| Red Fluorescent Proteins | | | | | | |
| mRuby | 558 | 605 | 112,000 | 0.35 | Monomer | 117 |
| mApple | 568 | 592 | 75,000 | 0.49 | Monomer | 109 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| dKeima-Tandem | 440 | 620 | 28,800 | 0.24 | Monomer | 21 |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |

*Weak Dimer

As used herein, the term "BRETFect signal" (or "BRET-Fest signal") is meant to refer to the specific BRET signal which is observed between two proteins in the presence of a third interacting partner in accordance with the present invention. The BRETFect signal is measured as the difference between the ratios of the Acceptor (A) emission over Initial Donor (D) emission in a condition containing D, I and A and the sum of the ratios measured with D-I and D-A alone. A positive BRETFect signal is indicative of the formation of a ternary or quaternary complex.

"Overlap" as used in the context of the present invention refers to the ability of the emitted light from a donor luminescent enzyme (e.g., luciferase) to be of a wavelength capable of excitation of a fluorophore placed in close proximity and/or to the ability of the emitted light from a fluorophore to be of a wavelength capable of excitation of another fluorophore placed in close proximity (usually within 100 Å). In an embodiment, the overlap means that the overlap between the emission spectrum of the donor and the excitation spectrum of the acceptor (i.e. the % of the area of the excitation spectrum of the acceptor that is "shared with" the emission spectrum of the donor, as illustrated by the black arrow shared by Luc-Em and FP1-Ex in FIG. 1A) is ideally 40% or more, preferably 45%, 50%, 60%, 70% or 80% or more. In an embodiment, the overlap 50% or more. In an embodiment, the overlap is 60% or more. In an embodiment, the overlap is 70% or more. In another embodiment, "overlap" means that the excitation spectrum of the donor overlaps with the maximal or peak excitation wavelength of the acceptor.

The term "overlap minimally" or "does not significantly overlap" means that the overlap between the excitation spectrum of the donor (FP1) and the excitation spectrum of the acceptor (FP2) is 35% or less, preferably 30, 20, 15%, 10%, or 5% or less. In an embodiment, "overlap minimally" or "does not significantly overlap" means that the overlap is 30% or less. In an embodiment, "overlap minimally" or "does not significantly overlap" means that the overlap is 25% or less. In an embodiment, "overlap minimally" or "does not significantly overlap" means that the overlap is 20% or less. In an embodiment, "overlap minimally" or "does not significantly overlap" means that the overlap is 15% or less. In an embodiment, "overlap minimally" or "does not significantly overlap" means that the overlap is 10% or less.

In another embodiment, "overlap minimally" or "does not significantly overlap" means that the excitation spectrum of the donor (FP1-Ex) does not overlap with the maximal or peak excitation wavelength of the acceptor (FP2-Ex). The mTFP1-Venus is a representative combination of fluorophores that fulfill this condition of "minimal overlap". The excitation spectrum of mTFP1 (FP1) ranges from about 400 nm to about 500 nm (maximum=about 462 nm), and the maximal excitation wavelength of Venus (FP2) is about 515 nm, thus the upper limit of the excitation spectrum of mTFP1 (500 nm) does not overlap with the maximal excitation wavelength of Venus (515 nm).

The BRETFect biosensor/method can measure the combined interaction between the D, I and A together or each pair separately provided three different conditions are present:

i. Presence of D and A. In this condition D and A interaction can be monitored by BRET using appropriate filter combinations;
ii. Presence of D and I. In this condition D and I interaction can be monitored by BRET using appropriate filter combinations (different from above);
iii. Presence of D, I and A. In this condition I-A interactions can be monitored by Fluorescence Resonance Energy Transfer using standard methods. Moreover D, I and A interaction can be monitored by BRETFect as the BRET signal between D and A is amplified by the presence of I in the complex.

Figure 4A:
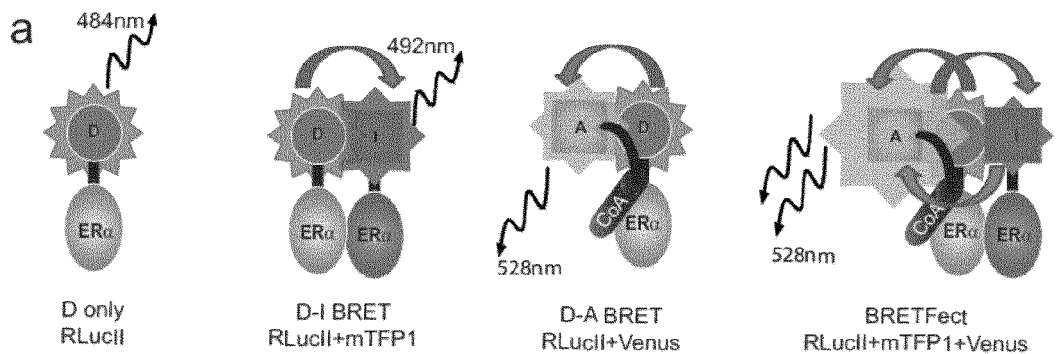
(FIG. 4A) Description of D (ERα-RLucII), I (ERα-mTFP1) and A (CoApep-Venus) fusion proteins and schematized energy transfer in the presence of two or three partners.

As shown in FIG. 4A, in the BRETFect biosensor/method according to embodiments of the present invention:
  a. Following enzymatic conversion of its substrate by luciferase, energy is transferred from D to I and from D to A (i.e., BioI/Luc to FP1 and FP2) in a combined manner. However, I and A absorb a different portion of the BioI/Luc-Em spectrum, such that the transfers from BioI/Luc to I and A are complementary rather than competitive. This step is specific and involved in BRETFect.
  b. Energy absorbed by I can be radiated as fluorescence or be transferred to A via FRET if I and A are in the same complex.
  c. Energy absorbed by A is radiated as fluorescence. In the case where A is in complex with D and I, more energy is absorbed and radiated than with only D as a donor leading to the Fluorescence Amplification of BRET-Fect.

To measure the BRETFect signal, the ratio of A emission over D emission is measured with filter sets chosen according to the specificity of the BioI (e.g., Luc) and FP1/2 used in the assay. The A/FP2 emission filter can be centered on its emission peak to increase signal but a filter that is more red-shifted to decrease contamination from FP1 emission allows for better measurements. The D-BioI/Luc emission filter can be chosen to avoid the part of the BioI- (e.g., Luc) Em spectrum that is absorbed by the Intermediate (I) without compensating emission in the same detection channel, in order to avoid artifactual signals due to quenching of the BioI (e.g., Luc) emission by FP1 upon interaction of D and I. In an embodiment, the BioI- (e.g., Luc-) Em has a longer wavelength than the FP1-Ex. In an embodiment, FP1-Ex does not overlap with FP2-Ex. In an embodiment, this is no or significantly no overlap between FP2-Em and FP1-Em.

The BRETFect signal is defined as the difference between the ratio of A over D emission in the ternary/quaternary condition and the sum of similar measurements for contaminating signal from D-I and D-A performed using the same A/FP2 and D/BioI- (e.g., Luc) Em filters. A positive BRETFect signal indicates formation of a ternary or quaternary complex.

In an embodiment, D is RLucII, I is mTFP1 and A is Venus, and the luciferase substrate is Coelenterazine H. In another embodiment, D is RLucII, I is mtagBFP2 (PDB) and A is mTFP1, and the luciferase substrate is Coelenterazine 400a.

BRETFect combines energy transfer between a luciferase Donor and an Intermediate and an Acceptor, appropriately chosen to also enable transfer from the Intermediate to the Acceptor while minimizing contaminating signals. This specific energy transfer mechanism was shown to greatly improve signal detection. Further, titration experiments can provide information on the stoechiometry of the complex. The biosensor/method described herein is broadly applicable to the detection of any complex involving at least three proteins (same or different) such as those formed by nuclear receptors (and/or nuclear receptor-interacting proteins), GPCRs (and/or GPCR-interacting proteins) and Tyrosine Kinase receptors (RTKs) (and/or RTK-interacting proteins). There are several examples of protein complexes involving three or more protein/peptides molecules in various signalling pathways, such as those illustrated in FIGS. 16A to 16J.

In an embodiment, the biosensor/method described herein may be used to detect ternary or quaternary complexes involving one or more nuclear receptors. Accordingly, in an embodiment, at least one of the first, second, third or fourth protein is a nuclear receptor protein or a suitable fragment thereof, i.e. a fragment that maintains the ability to oligomerize (e.g., dimerize, trimerize) and/or to interact with one or more of its binding partners to form a ternary or quaternary complex.

As used herein, the term "nuclear receptor" refers to a class of proteins found within cells that are responsible for sensing steroid and thyroid hormones and certain other molecules. In response, these receptors work with other proteins to regulate the expression of specific genes, thereby controlling the development, homeostasis, and metabolism of the organism. Non-limiting examples of nuclear receptors include: Estrogen receptor (ERα and ERβ), Retinoic acid receptors (RXRγ, RARα), orphan receptor Nurr77, Androgen receptor (AR), Glucocorticoid receptor (GR), Progesterone receptor (PR), etc. Nuclear receptors are involved in the formation of ternary complexes involving receptor dimers and and coactivator/corepressor proteins (6-10), which can be detected using the biosensor/assay described herein. An embodiment uses estrogen receptors alpha (ERα) or beta (ERβ) as homo- or heterodimers. Another embodiment uses RAR and RXR.

Nuclear receptors have the ability to directly bind to DNA and regulate the expression of adjacent genes, hence these receptors are classified as transcription factors. The regulation of gene expression by nuclear receptors generally only happens when a ligand—a molecule that affects the receptor's behavior—is present. More specifically, ligand binding to a nuclear receptor results in a conformational change in the receptor, which, in turn activates the receptor, resulting in up-regulation or down-regulation of gene expression.

In an embodiment, at least two, or two, of the first, second third and/or fourth proteins are nuclear receptor proteins or suitable fragments thereof. The at least two, or two nuclear receptor proteins or fragments may be the same nuclear receptor proteins or fragments (e.g., ERα-ERα; ERβ-ERβ) or different nuclear receptor proteins or fragments or different (e.g., ERα-ERβ).

Nuclear receptors bound to hormone response elements recruit a significant number of other proteins (referred to as transcription coregulators) that facilitate or inhibit the transcription of the associated target gene into mRNA. The function of these coregulators (coactivators, corepressors), are varied and include chromatin remodeling (making the target gene either more or less accessible to transcription) or a bridging function to stabilize the binding of other coregulatory proteins. Nuclear receptors may bind specifically to a number of coregulator proteins, and thereby influence cellular mechanisms of signal transduction both directly, as well as indirectly. Non-limiting examples of coregulatory proteins or derived peptides/domains include the p160 steroid receptor coactivators, the p300/CBP coactivators, the NCoR or SMRT corepressors. In addition, protein modifiers such as ubiquitin and SUMO can also be used in this system to monitor covalent modifications of nuclear receptors. In an embodiment, at least one of the first, second third or fourth protein is a nuclear receptor interacting domain or nuclear receptor interacting domain (NID)-containing protein, such as a nuclear receptor coactivator protein or a nuclear receptor interacting fragment thereof. Nuclear receptor interacting domains typically contain one or several LXXLL motifs. Examples of NID-containing protein include steroid receptor coactivator (SRC) proteins such as nuclear receptor coactivator 1 (NCOA1 or SRC1), nuclear receptor coactivator 2 (NCOA2 or SRC2) and nuclear receptor coactivator 3 (NCOA3 or SRC3), activating signal cointegrator-2 (ASC-2), TRAP220, TIP60, TIF1α and PGC1. In an embodiment, the NID-containing protein comprises the NID of NCOA1 or NCOA2. In further embodiment, the NID or NID-containing protein comprises the amino acid sequence of SEQ ID NO:10 or 11.

In an embodiment, the biosensor/method described herein may be used to detect ternary or quaternary complexes involving one or more GPCRs and/or G protein subunits (i.e. one or more of the first, second third and/or fourth proteins is/are GPCRS and/or G protein subunits). The term "GPCR" refers to a class of integral membrane proteins that possess seven membrane-spanning domains or transmembrane helices and which signal through G proteins. As used herein, the term "GPCR" encompasses full length native GPCR molecules as well as mutant GPCR molecules (e.g., fragments or variants of native GPCRs) that maintain the ability to dimerize/oligomerize and/or interacts with binding partners in a manner that can be modulated by ligands (11). In an embodiment, the GPCR is a native GPCR. Examples of GPCRs include 5-Hydroxytryptamine receptors, Acetylcholine receptors (muscarinic), Adenosine receptors, Adhesion Class GPCRs, Adrenoceptors, Angiotensin receptors, Apelin receptor, Bile acid receptor, Bombesin receptors, Bradykinin receptors, Calcitonin, receptors, Calcium-sensing receptors, Cannabinoid receptors, Chemerin receptor, Chemokine receptors, Cholecystokinin receptors, Class Frizzled GPCRs, Complement peptide receptors, Corticotropin-releasing factor receptors, Dopamine receptors, Endothelin receptors, Estrogen (G protein-coupled) receptor, Formyl-peptide receptors, Free fatty acid receptors, GABAB receptors, Galanin receptors, Ghrelin receptor, Glucagon receptor family, Glycoprotein hormone receptors, Gonadotrophin-releasing hormone receptors, Histamine receptors, Hydroxy-carboxylic acid receptors, Kisspeptin receptor, Leukotriene receptors, Lysophospholipid (LPA) receptors, Lysophospho-lipid (S1P) receptors, Melanin-concentrating hormone receptors, Melanocortin receptors, Melatonin receptors, Metabotropic glutamate receptors, Motilin receptor, Neuro-medin U receptors, Neuropeptide FF/neuropeptide AF receptors, Neuropeptide S receptor, Neuropeptide W/neuro-peptide B receptors, Neuropeptide Y receptors, Neurotensin receptors, Opioid receptors, Orexin receptors, Oxoglutarate receptor, P2Y receptors, Parathyroid hormone receptors, Peptide P518 receptor, Platelet-activating factor receptor, Prokineticin receptors, Prolactin-releasing peptide receptor, Prostanoid receptors, Proteinase-activated receptors, Relaxin family peptide receptors, Somatostatin receptors, Succinate receptor, Tachykinin receptors, Thyrotropin-releasing hormone receptors, Trace amine receptor, Urotensin receptor, Vasopressin and oxytocin receptors, VIP and PACAP receptors. A list of GPCRs is given in Foord et al. (12) and an updated list of GPCRs is available in the IUPHAR-DB database (13,14).

GPCRs and G protein subunits (e.g., Gβ, Gα and Gγ) are known to interact directly or indirectly and form multiprotein complexes with several accessory and signaling proteins such as G-protein-coupled receptor kinases, other cell surface receptors or membrane proteins, βarrestin, regulators of G-protein signalling (RGS) proteins (RGS1 to 22), activators of G-protein signalling (AGS) proteins (also referred to as G-protein-signaling modulator (GPSM) proteins, resistance to inhibitors of cholinesterase 8 proteins (Ric-8), etc. Examples of ternary complexes involving one or more GPCRs and/or G protein subunits that may be detected using the biosensor/method described herein include GPCR-Gα-Gγ, GPCR-GRK-Gα, GPCR-GRK-Gβ, GPCR homodimer-Gα, GPCR heterodimer-Gα, GPCR homodimer-Gβ, GPCR heterodimer-Gβ, GPCR homodimer-βarrestin, GPCR heterodimer-βarrestin, GPCR-Gβ-βarrestin, GPCR-Gα-Gβ, GPCR-GRK-Gβ, GPCR-membrane protein-Gα, GPCR-membrane protein-Gβ, GPCR-membrane protein-Gγ, GPCR-membrane protein-GRK, GPCR-membrane protein-βarrestin, GPCR-membrane protein-RGS, GPCR-RGS-Gα and GPCR-AGS-Gα. Examples of membrane proteins that interact directly or indirectly (e.g., through scaffold proteins such as RGS proteins) with GPCRs include RAMP1, RAMP2, RAMP3, LRP5, LRP6, certain RTKs (FGFR1, EGFR) and adenylate cyclase.

Screening Assays

The biosensor/method described herein can advantageously be used to identify compounds which modulate the formation of ternary or quaternary complexes. Formation of ternary or quaternary complexes can be tested by BRETFect in the presence and absence of one or more test compounds. An increase or a decrease in the BRETFect signal in the presence of a test compound indicates that the compound is able to modulate (i.e., increase or decrease, stabilize or inhibit) the formation of the ternary or quaternary complex. Potencies of different ligands for ternary or quaternary complex assembly can be measured, and when different isoforms of the components of ternary or quaternary complexes are possible, allosteric effects of each monomer isoform on ligand-dependent trimer formation can be detected by comparing ligand potencies with ternary or quaternary complexes containing different isoforms.

Thus, in another aspect, the present invention relates to a method for determining whether an agent (e.g., a molecule, compound or ligand) modulates the formation of a ternary or quaternary protein complex comprising performing the method defined above in the presence and in the absence of said agent, wherein an increase in BRETFect signal in the presence of the agent relative to the absence thereof is indicative that the agent promotes the formation of the ternary or quaternary protein complex, and wherein a reduction in BRETFect signal in the presence of the agent relative to in the absence thereof is indicative that the agent inhibits the formation of the ternary or quaternary protein complex.

As used herein, the terms "molecule", "compound", "agent" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non-limiting examples of molecules include nucleic acid molecules, peptides, antibodies, carbohydrates and pharmaceutical agents. The agents can be selected and screened by a variety of means including random screening, rational selection and by rational design using for example protein or ligand modeling methods such as computer modeling. A test compound is a compound which is tested to determine whether it can modulate (increase or decrease, stabilize or inhibit) the formation of ternary or quaternary complexes in accordance with the present invention.

In accordance with the present invention, any test compound suspected of modulating the activity/formation of a ternary or quaternary complex can be used. The compounds can be tested individually or several test compounds may be tested at the same time.

The method of the present invention can also be used to identify small interfering RNAs (shRNAs, siRNAs) or cDNAs which modulate the formation of ternary or quaternary complexes.

Figure 13:
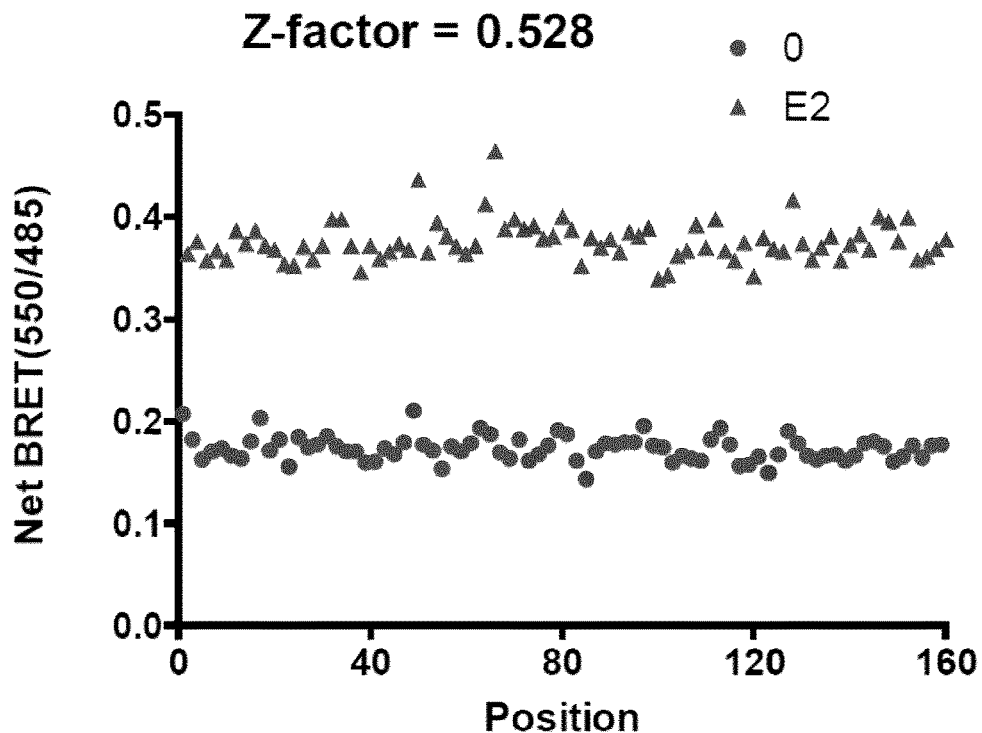
FIG. 13—BRETFect assays are compatible with high-throughput screening of heterodimer activity. Cells transfected with ERβ-RLucII, ERα-mTFP1 and CoApep-Venus were seeded in two 96-well plates and alternate rows were treated with vehicle (0) or estradiol (E2). BRET ratios from individual wells are plotted on the graph against the position of the wells. The Z-factor was calculated as described in Zhang et al. 1999 (2). With a Z-factor higher than 0.5, the BRETFect assay qualifies as a suitable assay.

BRETFect assays were shown to be sufficiently robust to be amenable to high-throughput screening assays of small molecule libraries, small interfering RNA libraries or cDNA libraries (see, e.g., FIG. 13)

Kits

The present invention also encompasses kits which can be used to monitor the formation of high order (e.g., ternary complexes) in cells using BRETFect. Kits of the present invention may comprise:

A) one or more vectors for expressing:
  i. a first protein tagged with a Donor (D) protein, wherein D is a bioluminescent protein (Biol) having an emission spectrum (Biol-Em);
  ii. a second protein tagged with an Intermediate (I) protein, wherein I is a first Fluorescent protein (FP1) having an excitation spectrum (FP1-Ex) and emission spectrum (FP1-Em);
  iii. a third protein tagged with an Acceptor (A) protein, wherein A is a second fluorescent protein (FP2) having an excitation spectrum (FP2-Ex) and an emission spectrum (FP2-Em);
or
  i. a first protein tagged with a first portion of a Donor protein (D1), wherein D1 is a first bioluminescent protein portion (BiolP1);
  ii. a second protein tagged with a second portion of a Donor protein (D2), wherein D2 is a second bioluminescent protein portion (BiolP2);
  iii. a third protein tagged with an Intermediate (I) protein, wherein I is a first Fluorescent protein (FP1) having an excitation spectrum (FP1-Ex) and emission spectrum (FP1-Em);
  iv. a fourth protein tagged with an Acceptor (A) protein, wherein A is a second fluorescent protein (FP2) having an excitation spectrum (FP2-Ex) and an emission spectrum (FP2-Em);
wherein said BiolP1 and BiolP2 can form a functional bioluminescent protein (Biol) having an emission spectrum Em if brought in close enough proximity,
wherein
  a) the FP1-Ex overlaps with the Biol-Em and does not significantly overlaps with the FP2-Ex;
  b) the FP1-Em overlaps with FP2-Ex;
  c) the FP2-Ex overlaps with the Biol-Em; and
  d) the FP2-Em has a longer wavelength than the FP1-Em.

In an embodiment, the kit comprises:
A)
  i. a vector comprising a nucleic acid encoding said bioluminescent protein (e.g., luciferase) having an emission spectrum (Biol-Em);
  ii. a vector comprising a nucleic acid encoding a first fluorescent protein (FP1) having an excitation spectrum (FP1-Ex) and emission spectrum (FP1-Em); and
  iii. a vector comprising a nucleic acid encoding a second fluorescent protein (FP2) having an excitation spectrum (FP2-Ex) and an emission spectrum (FP2-Em).

The kit may also be adapted for detecting higher order complexes (e.g., quaternary complexes) by adapting the kit to include a PCA component, as described herein. In such an embodiment, one of the reporter proteins (e.g., FP1) would be divided in two parts, which when placed into close proximity can reconstitute a functional protein non-covalently. Such a kit could thus comprise for example one or more vectors for expressing two proteins each tagged with luciferase portion (Luc). Other reporter proteins may also be used in accordance with the present invention.

The vector(s) above permit the cloning of nucleic acids encoding proteins of interest (which form or are suspected to form a complex) so as to allow expression of these proteins of interest tagged with a bioluminescent protein (e.g., luciferase), FP1 and FP2. The formation of a complex between the proteins of interest may be monitored using the biosensor/method described herein.

Optionally, the kit will further comprise suitable luciferase substrate and instructions for detecting a ternary or quaternary complex by BRETFect. The kit may also comprise any other reagent suitable for the purpose of the kit. For example, transfection reagents may also be included. Also, the kit may further comprise ligands which are normally necessary to promote the activity and formation of a ternary or quaternary complex. For example nuclear receptors ligands (estrogen, retinoic acid, lipids, testosterone, progesterone, etc.) or GPCR ligands may further be included in the kit.

Cells Expressing Fusion Proteins Comprising D (D1, D2), I and A

The present invention also provides cells expressing a suitable combination of proteins tagged with Donor (D) (or D1 and D2), Intermediate (I) and Acceptor (A) proteins to monitor formation of a ternary or quaternary complex using the biosensor/method described herein. As indicated above, when a PCA component is incorporated in the biosensors, methods and kits disclosed herein (e.g., to detect a quaternary complex), the cells will express at least one of D, I and A in portions (e.g., two portions) which when expressed may reconstitute a functional protein non-covalently when placed into close proximity (upon interaction/oligomerization of the two portions). The cells will express D, I and A and control cells expressing either (i) D and I, (ii) I and A and (iii) D and A may also be provided in order to monitor BRETFect signal and formation of ternary complexes. The specific type of cells used will be chosen in accordance with the specific ternary complex and associated activity that is detected.

In the following non-limiting Examples, effectiveness of the BRETFect assay in accordance with embodiments of the present invention is illustrated by demonstrating that ligands specific for estrogen receptor alpha (ERα) can activate α/β heterodimers and that each monomer allosterically regulates the other. BRETFect was validated for the robust, HTS-compatible detection of coactivator recruitment and SUMO modification on estrogen receptor homo- and heterodimers in live cells. BRETFect notably revealed recruitment of AF1-interacting to activation of ERα/β heterodimers by the ERα-specific ligand PPT and an allosteric control of coactivator recruitment between liganded dimeric partners in live cells.

Example 1: Materials and Methods

Cell Lines, Plasmids and Reagents

HEK293 cells (Sigma-Aldrich®, Oakville, Ontario, Canada) were grown in DMEM with 10% fetal bovine serum (Wisent® Inc., St-Bruno, Quebec, Canada). Polyethyleneimine (25 kDa molecular mass, linear or branched forms) was obtained from Sigma-Aldrich®. Coelenterazine H and Coelenterazine 400a were obtained from NanoLight Technology® (Pinetop, Ariz.). 17-beta-Estradiol (E2) and 4-hydroxytamoxifen (OHT) were purchased from Sigma-Aldrich®, RU58668 (RU58), ICI182,780 (ICI182) and raloxifene (Ral) were purchased from Tocris® Cookson Ltd (Minneapolis, Minn.). pcDNA-RLucII vectors are described in (4). pCMV-Venus and pCMV-mTFP1 were generated by amplification of the relevant fluorophore genes and replacement of the eGFP in the peGFP-N1 vector (PerkinElmer Corp., Wellesley, Mass.). ERα/β and Nur77 cDNAs were cloned into the above-described vectors by PCR amplification of coding sequence and digestion of 5' and 3' ends with appropriate restriction enzymes. The coactivator construct was generated by inserting oligonucleotides coding for a repeat of the first NCOA2 LXXLL motif (WT sequence: GAT CTA ACC ATG AAG CAT AAA ATT TTG CAC AGA CTC TTG CAG GAC AGC AGT CTC GAG ATG AAG CAT AAA ATT TTG CAC AGA CTC TTG CAG GAC AGC AGT CTC GAG, SEQ D NO: 1; non-interacting mutant sequence: GAT CTA ACC ATG AAG CAT AAA ATT GCG CAC AGA GCC GCG CAG GAC AGC AGT CTC GAG ATG AAG CAT AAA ATT GCG CAC AGA GCC GCG CAG GAC AGC AGT CTC GAG, SEQ D NO: 2) and a NLS sequence derived from GR (sequence: GAT CGA GCC CAC TCC ACA CCT CCA AAA AAC AAA CGA MC GTT CGA GAT CCC AAG GAT CGA GCC CAC TCC ACA CCT CCA AAA AAC AAA CGA AAC GTT CGA GAT CCC MG, SEQ D NO: 3) into pCMV-Venus. The ERα(L507R) mutant was created by overlapping primer site-directed mutagenesis. The SRC1-RID was cloned from NCOA1 cDNA with primers flanking the third and fifth LXXLL motif in 5' and 3' respectively (positions 2155 to 2517 in NCBI Reference Sequence NM_003743—oligo sequence: ATG TAC TCT CAA ACC AGT CAC AAA, SEQ D NO: 4) and TGA GGG GCT ACC CTC CTG, SEQ D NO:5). The AF1-interacting domain (AF1ID) encompasses the glutamine rich region of SRC1, cloned from NCOA1 cDNA positions 3129 to 3782 into Venus expression vector as for CoApep. SUMO3-Venus was obtained from Dr M. K. Chelbi-Alix, French National Centre for Scientific Research, France.

HEK293 Cell Transfection

HEK293 cells were maintained in DMEM supplemented with 10% fetal bovine serum (FBS) in 175 $cm^2$ culture flasks. Two days before experiments, HEK293 cells were harvested and switched to phenol red-free DMEM containing 10% charcoal-stripped serum. HEK293 cells were transfected via PEI with 1.66 µg of DNA, 1.66 µg PEI-branched and 5 µg PEI-linear per $10^6$ cells. DNA mixes and PEI dilutions were made in a total volume of 75 ml PBS separately before mixing. After 10 minutes incubation, HEK293 cell suspensions ($1.25 \times 10^6$/ml) were added directly to the DNA-PEI transfection mixes (850 µl of cells per 150 µl of transfection mix) and 100 µl for DNA-PEI-cell suspensions was aliquoted per well in 96-well white-bottom culture plate (Corning) and grown for 48 hours.

Bioluminescence Resonance Energy Transfer Assays

Unless otherwise indicated, BRET assay transfection mixes contained 150 ng of RLuc-tagged donor and 0 to 1.5 µg of YFP-tagged acceptor for titrations or 1.5 µg for single point experiments. 48 hours after transfection cells were washed with PBS and treated with specified ligands or vehicle (0.1% DMSO) in 100 µl PBS for 40 minutes at 37° C. Coelenterazine H was added to a final concentration of 5 µM, and readings were immediately collected on a Mithras™ LB 940 (Berthold Technologies™, Bad Wildbad, Germany), with sequential integration of signals detected at 485 nm (*Renilla* luciferase emission) and LP550 nm (YFP emission). BRET ratios displayed for titration curves are the stimulated YFP emission (exc 485 nm, em LP550 nm) acquired with a FlexStation™ 3 Microplate Reader (Molecular Devices®) divided by Luciferase emission as recorded by the Mithras™ LB 940 in the 485 nm channel. Net BRET values (BRET ratios for fused proteins minus BRET ratios with fused Luciferase but unfused GFP) are represented as a function of $Log_{10}$([Fluorescent protein]/Luc). Emission spectrum experiments (FIG. 3) were performed on a Synergy Neo™ microplate reader (Biotek®, Winooski Vt., USA) using 2 nm intervals from 400 to 600 nm and Relative Light Units (RLU) are calculated as a fraction of the maximal value recorded in each condition (arbitrarily set at 1.00). All graphs were built using GraphPad® Prism 5.00 which analyzed titration data using non-linear regression curve fit with variable slope (log(agonist) vs. response) and one point comparison using ANOVA and the Bonferroni post-hoc test to determine confidence intervals.

SRET, BRETFect and FRET Assays

Unless otherwise indicated, BRETFect and SRET assay transfection mixes contained 100 ng of LucII tagged donor, with or without 400 ng of mTFP1 tagged I and/or 1 μg of Venus tagged acceptor (total DNA concentration kept constant with pcDNA3.1-Hygro). For spectral analysis of emission (FIG. 3), cells were transfected with 250 ng ERα-LucII, 500 ng untagged-ERα for D+A condition or 500 ng ERα-mTFP1 for D+I+A condition and 750 ng CoApep-Venus for D+A and D+I+A. Moreover, cells were suspended and plated at 500,000 cells per well. These special steps were taken to optimize signal output to allow for spectral analysis. For BRETFect titration (FIG. 5), levels of ERα-mTFP1 transfected remained constant at 1 μg while CoApep-Venus varied from 0 to 1 μg (FIG. 5C) and levels of CoApep-Venus remained constant at 400 ng while ERα-mTFP1 or ERα varied from 0 to 400 ng transfected (FIG. 5D). Cell treatment and acquisition was performed as for BRET assays. Readings were collected using 485 nm (Donor) and LP550 nm (Acceptor) filters for BRETFect and 400 nm (Donor) and 530 nm (Acceptor) filters for SRET on the Mithras™ LB 940. LP550 filters were used instead of 530 nm to limit bleed-in from mTFP1 emission in BRETFect assays but use of a 530 nm filter yielded similar delta BRET signal. The mTFP1 emission captured in the 485 nm-RLuc filter more than compensated for the quenching of Luc emission. BRETFect signals correspond to the delta BRET measures calculated by subtraction from the three-partner BRET ratios of the sum of those obtained with either of the mTFP1 or the Venus partners. Net SRET was calculated as described in 1. FRET assays were performed on the same cells before addition of coelenterazine using the FlexStation 3™ Microplate Reader with excitation of mTFP1 at 420 nm and emission of mTFP1 at 495 nm and emission of Venus at 550 nm. FRET ratio was calculated as (em550 nm)/(em495 nm).

```
Amino acid sequence of RLucII
                                                      (SEQ ID NO: 6)
MTSKVYDPEQRKRMITGPQWWARCKQMNVLDSFINYYDSEKHAENAVIFLHGNATSSYLWRH

VVPHIEPVARCIIPDLIGMGKSGKSGNGSYRLLDHYKYLTAWFELLNLPKKIIFVGHDWGAA

LAFHYSYEHQDKIKAIVHAESVVDVIESWDEWPDIEEDIALIKSEEGEKMVLENNFFVETVL

PSKIMRKLEPEEFAAYLEPFKEKGEVRRPTLSWPREIPVLKGGKPDVVQIVRNYNAYLRASD

DLPKMFIESDPGFFSNAIVEGAKKFPNTEFVKVKGLHFSQEDAPDEMGKYIKSFVERVLKNE

Q*

Amino acid sequence of mTFP1
                                                      (SEQ ID NO: 7)
MVSKGEETTMGVIKPDMKIKLKMEGNVNGHAFVIEGEGEGKPYDGTNTIN    50

LEVKEGAPLPFSYDILTTAFAYGNRAFTKYPDDIPNYFKQSFPEGYSWER   100

TMTFEDKGIVKVKSDISMEEDSFIYEIHLKGENFPPNGPVMQKKTTGWDA   150

STERMYVRDGVLKGDVKHKLLLEGGGHHRVDFKTIYRAKKAVKLPDYHFV   200

DHRIEILNHDKDYNKVIVYESAVARNSTDGMDELYK*

Amino acid sequence of Venus
                                                      (SEQ ID NO: 8)
MVSKGEELFTGVVPILVELDGDVNGHKFSVSGEGEGDATYGKLTLKLICT    50

TGKLPVPWPTLVTTLGYGLQCFARYPDHMKQHDFFKSAMPEGYVQERTIF   100

FKDDGNYKTRAEVKFEGDTLVNRIELKGIDFKEDGNILGHKLEYNYNSHN   150

VYITADKQKNGIKANFKIRHNIEDGGVQLADHYQQNTPIGDGPVLLPDNH   200

YLSYQSALSKDPNEKRDHMVLLEFVTAAGITLGMDELYK*

Amino acid sequence of BFP2 (PDB)
                                                      (SEQ ID NO: 9)
MVSKGEELIKENMHMKLYMEGTVDNHHFKCTSEGEGKPYEGTQTMRIKVV    50

EGGPLPFAFDILATSFLYGSKTFINHTQGIPDFFKQSFPEGFTWERVTTY   100

EDGGVLTATQDTSLQDGCLIYNVKIRGVNFTSNGPVMQKKTLGWEAFTET   150

LYPADGGLEGRNDMALKLVGGSHLIANAKTTYRSKKPAKNLKMPGVYYVD   200

YRLERIKEANNETYVEQHEVAVARYCDLPSKLGHKLN*
```

-continued

```
Amino acid sequence of Coactivator peptide (CoApep)
                                            (SEQ ID NO: 10)
MKHKILHRLLEDSSLEGSTMKHKILHRLLEDSSLEMDRRKTKKKIKGIQQATAGMDRRKTKK

KIKGIQQATAGMDPPVATMVSKGEELFTGVVPILVELDGDVNGHKF*

Amino acid sequence of AF1-interacting domain (AF1ID)
                                            (SEQ ID NO: 11)
DHRIEILNHDKDYNKVTVYESAVARNSTDGMDELYKEFATMNQLRLQLQQRLQGQQQLIHQN

RQAILNQFAATAPVGINMRSGMQQQITPQPPLNAQMLAQRQRELYSQQHRQRQLIQQQRAML

MRQQSFGNNLPPSSGLPVQMGNPRLPQGAPQQFPYPPNYGTNPGTPPASTSPFSQLAANPEA

GQFGTGINPQMQQNVFQYPGAGMVPQGEANFAPSLSPGSSMVPMPIGSPPV*
```

Example 2: Classification of ER Ligands Using BRET Assays

Figure 1B:
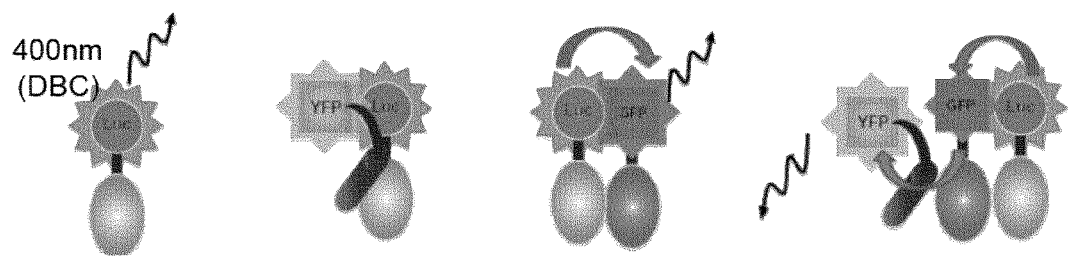
FIG. 1B shows the principles underlying Sequential Resonance Energy Transfer (SRET).

An aim of the present studies was to develop BRET assays that reliably monitor ternary complexes without the need for spectral unmixing and with robust signal output to enable the dissection of ternary protein complexes and application to high-throughput screens. One of the limitations of SRET is the need to transfer energy sequentially from the D (RLucII activated with Coelenterazine 400a for SRET) to the I (uvGFP) and subsequently from the I to the A (eYFP) (see FIG. 1B); this limits the choice of D and A to prevent direct transfer from D to A, which would bypass the I. However, it was discovered that the contribution of an I could be detected provided that the I uses a part of the emission spectrum of the D that only marginally contributes to excitation of the A, and can re-emit it to efficiently excite the A. This conceptual change results in greater flexibility in the choice of the emission/excitation wavelengths for the different reporter proteins.

Figure 1C:
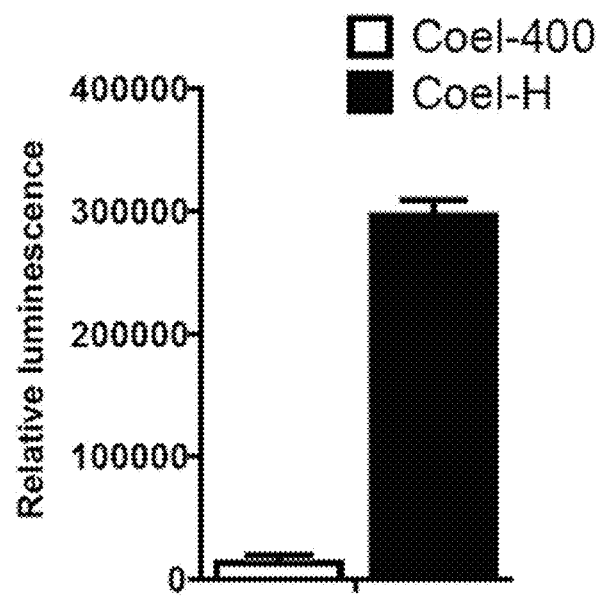
FIG. 1C shows that use of coelenterazine H instead of coelenterazine 400a greatly increases signal output. HEK293 cells were transfected with plasmid DNA encoding ERα-RLucII and mTFP1 as a transfection control. Cells were treated with coelenterazine H or 400a and luminescence was measured at 485 nm for Coel H and 400 nm for Coel 400. Data was normalized over control free mTFP1 fluorescence.

FIG. 1C shows that if the donor molecule is RLucII but coelenterazine 400 is switched for coelenterazine H, shifting the emission peak from 400 nm to 485 nm and significantly improving emission (by about 30-fold) (Kocan, M., et al., *J Biomol Screen,* 2008. 13(9): p. 888-98).

The use of coelenterazine H changes the pattern of energy transfer: while SRET relies on sequential transfer of energy from the RLucII to the I (uvGFP) and subsequently to the A (eYFP) (Carriba, P., et al., supra), here energy from the RLucII is transferred in a combined manner to I (mTFP1) and A (Venus). Importantly, the energy emitted from RLucII in the shorter wavelengths of the spectrum (400 to 460 nm), which is not favorable for A excitation, can be efficiently transferred to the I mTFP1, which will emit at 492 nm, a more favorable emission for Venus. Hence, Bioluminescence Resonance Energy Transfer with Fluorescence Enhancement by Combined Energy Transfer (BRETfect) monitors an amplification of the BRET increase in a donor+I+A condition versus the donor+A control condition.

Figure 2A:
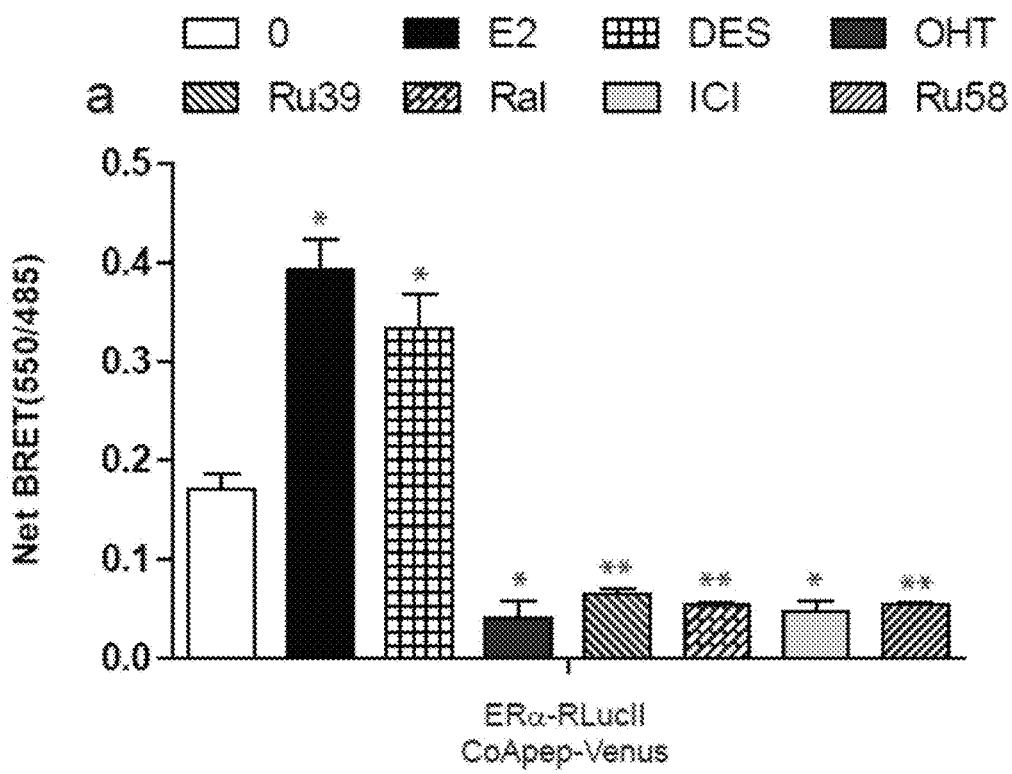
FIG. 2—Detection of agonist-induced coactivator interactions and of SERD-induced SUMOylation of ERα using BRET (FIG. 2A) HEK293 cells were transfected with ERα-RLucII and CoApep-Venus and treated with ligands or DMSO (Ve) for 45 minutes. Measurements of BRET ratios (550 nm/485 nm) are reported after subtraction of background ratio (luciferase alone). Values reported are the average of three biological replicate composed of three technical replicate each. Error bars represent SEM.
(FIG. 2B). HEK293 cells were transfected with ERα-RLucII and AF1ID-Venus and treated with ligands or DMSO (Ve) for 45 minutes. BRET measurements were performed as described in 2A (FIG. 2C). HEK293 cells were transfected with ERα-RLucII and SUMO3-Venus. BRET measurements were performed as described in 2A.
Figure 2B:
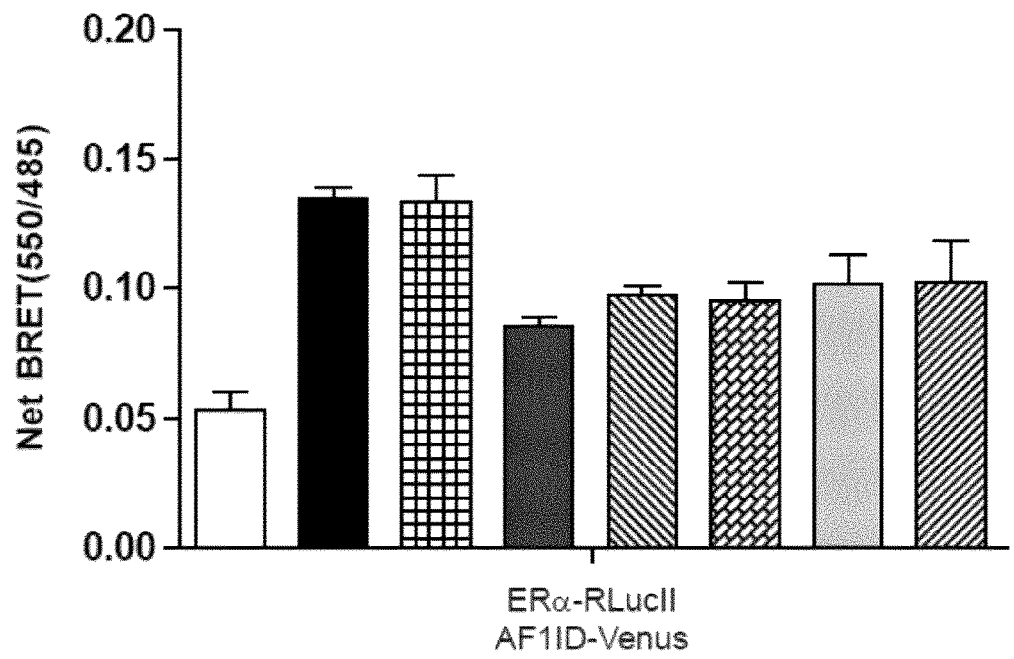
Figure 2C:
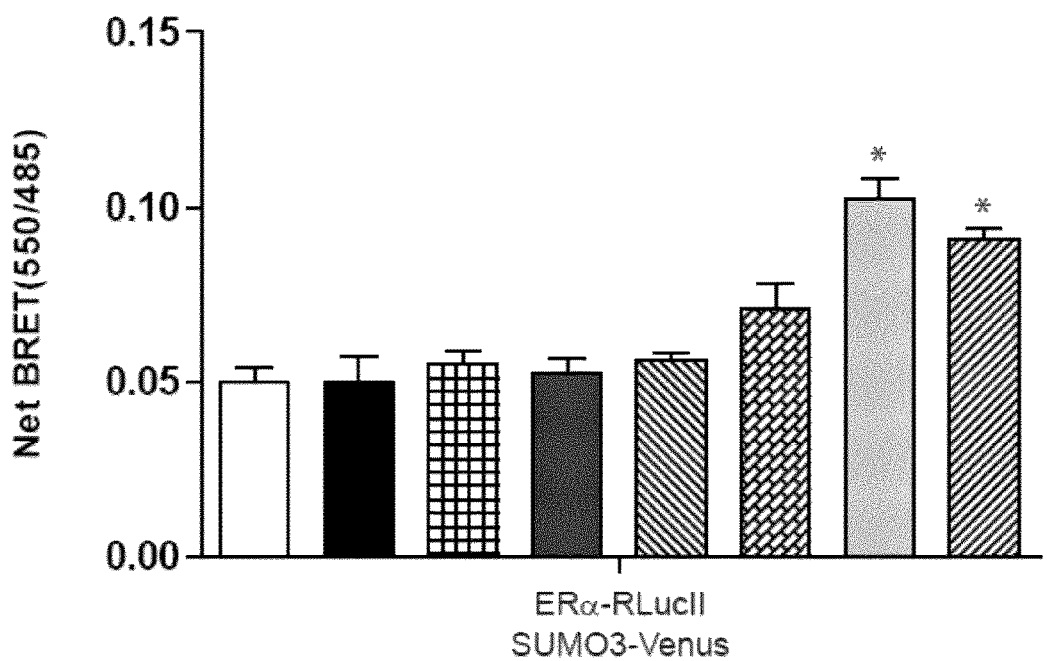
Figure 3A:
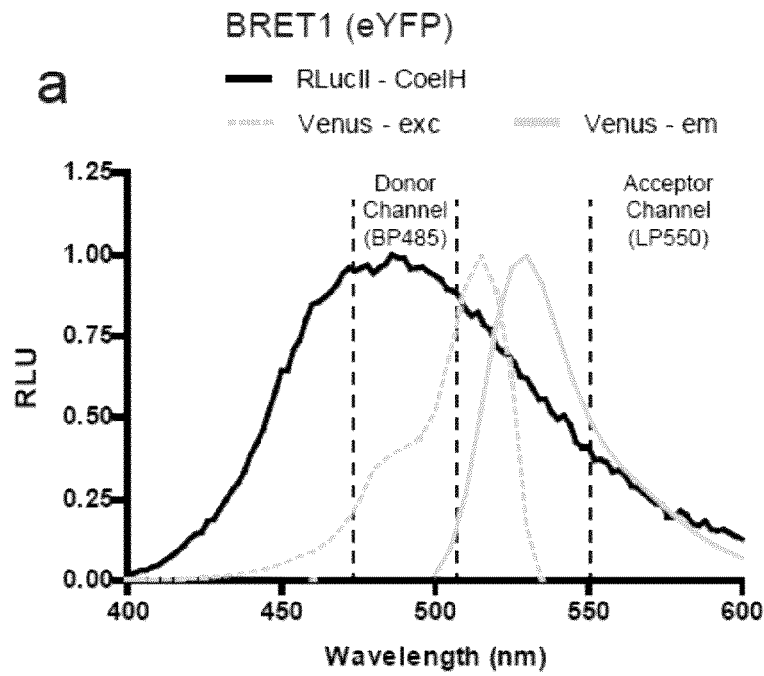
(FIG. 3A-D) Cells were transfected with free RLucII, mTFP1, GFP2 or Venus and fluorescence was measured from 460 to 600 nm with excitation at 400 to 535 nm with 5 nm increments. Luciferase emission was acquired with a monochromatic luminescence reader (400 nm to 600 nm with 2 nm increments) after incubation of cells with coelenterazine H (CoelH).
Figure 3B:
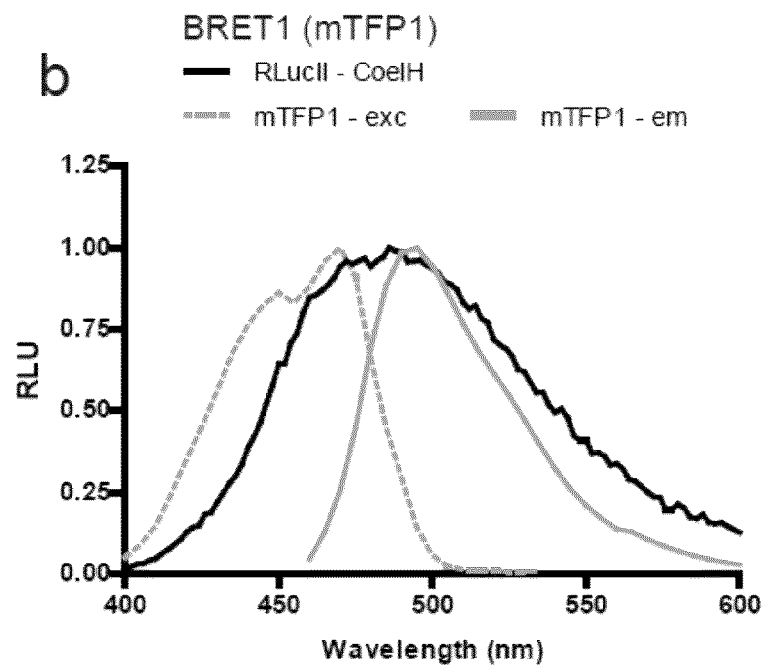
Figure 3C:
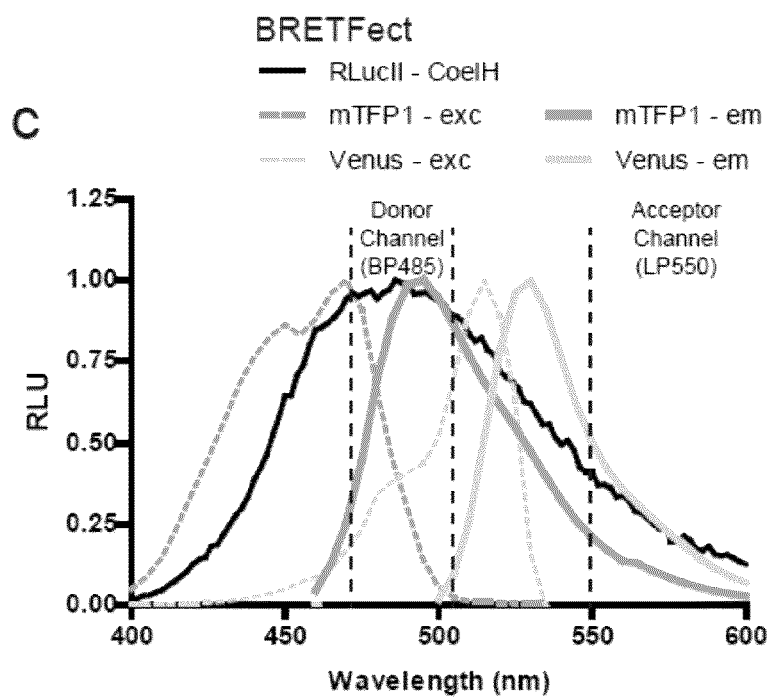
Figure 3D:
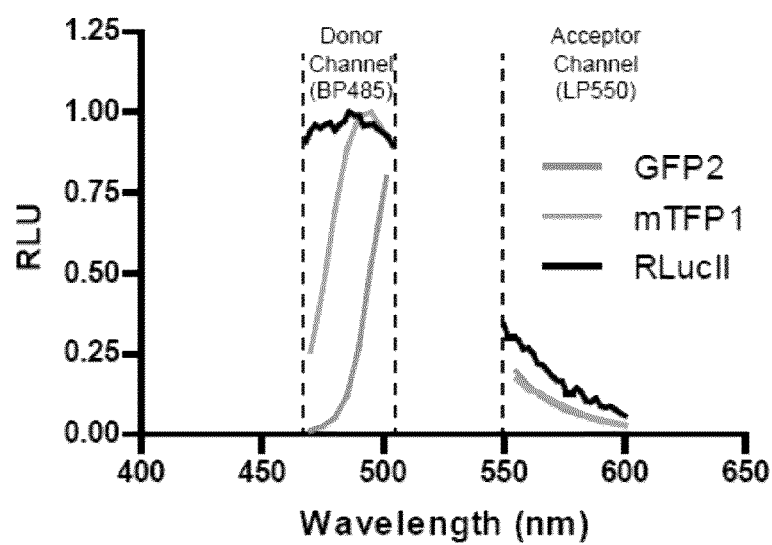

To fully characterize the pharmacological properties of ER ligands, assays that could reliably detect AF1 and AF2 coactivator binding were perfected (FIG. 2). Estrogens 17-β-estradiol (E2) and diethylstilbestrol (DES) induce recruitment of an AF2-binding coactivator peptide motif while all classes of antiestrogens, SERMs 4-hydroxytamoxifen (OHT), RU39411 and Raloxifene (Ral) as well as SERDs ICI182,780 and RU58668, suppress basal recruitment (FIG. 2A). Recruitment of the p160 coactivators by the AF1 region of ERα such as SRC1 was previously described both in the presence of estrogens and of the SERM tamoxifen (16-19). A BRET assay for recruitment of the AF1-interaction domain of SRC1 (aa 1043-1260, (19)) indicates that all antiestrogens induce partial recruitment of this domain to variable degrees, with no significant difference between SERDs and SERMs (FIG. 2B). Further, it was recently observed that SERDs, but not agonists or SERMs, induce SUMOylation of ERα, contributing to transcriptional suppression of this receptor (20) (FIG. 2C). Thus, together, these BRET assays discriminate between the three main classes of estrogen receptor ligands by their effects on cofactor recruitment and post-translational modifications of ERα. However, they do not allow to probe the effects of these ligands on ER heterodimers vs. homodimers, necessitating the use of assays capable of monitoring ternary complex formation.

Example 3: Ternary Complex Monitoring by BRETfect

Fluorescence Resonance Energy Transfer (FRET) and BRET both detect protein-protein interactions in real-time in intact cells (21,22). FRET allows reliable monitoring of sequential transfer between three fluorophores in a three-color or triple-FRET assay (23,24), but suffers from problems due to photobleaching and contaminating cross-excitation requiring spectral unmixing, which complicates high-throughput screening applications. Our aim was to develop a BRET assay that reliably monitors ternary complexes with robust signal output and without need for spectral unmixing. BRETfect achieves this by using a Donor (D)-Intermediate (I)-Acceptor (A) setup where the Acceptor receives energy directly from the Donor and indirectly via the Intermediate in a combined transfer. The Intermediate is chosen such that it can act as a relay to increase total energy transfer from the Donor to the Acceptor, by shifting parts of the emission spectrum that are poorly used by the Acceptor to wavelengths that are more readily absorbed. For instance, using mTFP1 as an Intermediate should enable efficient transfer of the energy emitted by the donor RLucII in the shorter wavelengths of its spectrum (400 to 460 nm), to wavelengths peaking around 492 nm, more favorable for Venus excitation (FIG. 3 and Table III). Thus, ternary complex formation is expected to result in an increase in the net BRET ratios measured using detection channels for the Acceptor and the Donor when all partners (Donor, Intermediate and Acceptor) are present in the cell compared to the sum of net BRET ratios of the binary complexes (i.e. D+I and D+A) (see below). Choosing the Intermediate to minimize contamination in the Acceptor channel facilitates the accurate detection of the ternary complex.

Negative controls for the contribution of the Intermediate in energy transfer should include the intermediate interaction partner in the absence of fusion with the fluorophore and mutant proteins that cannot interact with the donor or with the acceptor. In addition, choosing the fusion partner protein of the Intermediate as a more efficient interactor with the Acceptor compared to the Donor will also result in a more important contribution to the overall signal.

TABLE III

Excitation and emission wavelengths of the Donor, Intermediate and Acceptor used in this study

| Role | Protein-tag | Exc (nm) | Em (nm) |
|------|-------------|----------|---------|
| D | RLucII coelH |  | 484 |
| I | mTFP1 | 462 | 492 |
| A | Venus | 515 | 528 |

Example 4: Detection of Ternary Complexes Between ER Dimers and Cofactors by BRETFect Characterization or development of dimer-selective ligands is an important pharmacological priority in the development of novel therapeutics, but necessitates assays that can monitor activity of specific homodimers and heterodimers. Applicants thus determined whether BRETFect assays can distinguish between ERα/β homo- and heterodimers.

Figure 4B:
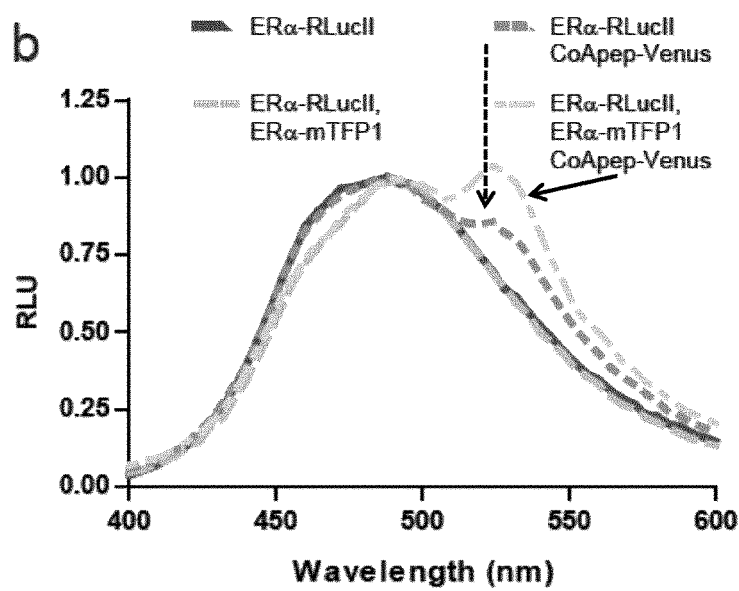
(FIG. 4B) Spectral analysis of BRETFect reveals energy transfer from ERα-RLucII to CoApep-Venus through ERα-mTFP1.
Figure 4C:
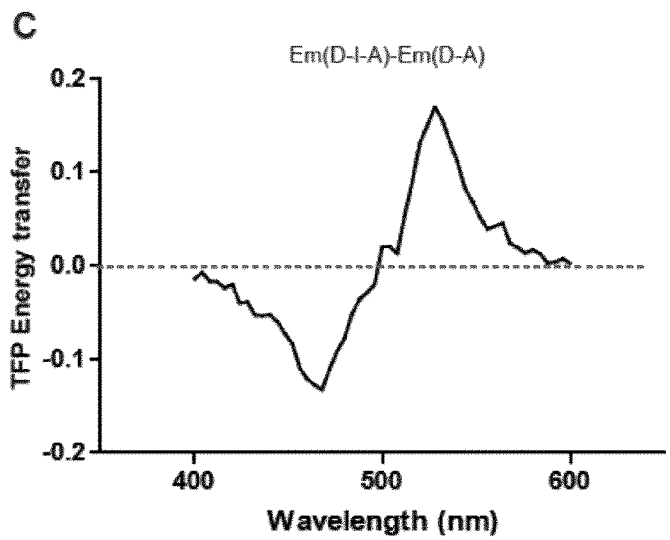
(FIG. 4C) Subtraction of emission in the presence of D and A [Em(D−A)] from ternary complex emission [Em(D−I−A)] across the wavelength spectrum.
Figure 5A:
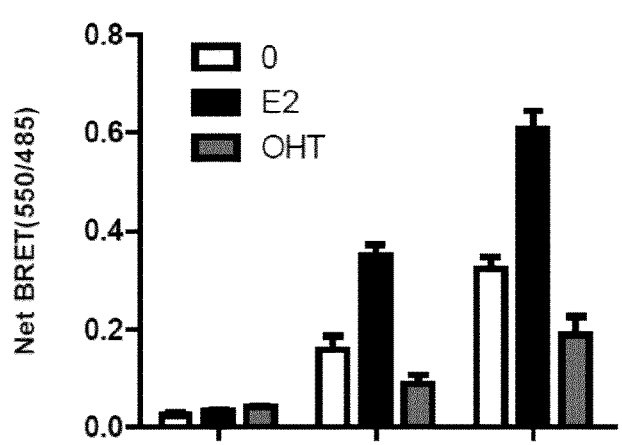
(FIG. 5A) Net BRET signals (550/485 nm) for the binary and ternary complexes after treatment with ligands (1 μM) for 40 min.
Figure 5B:
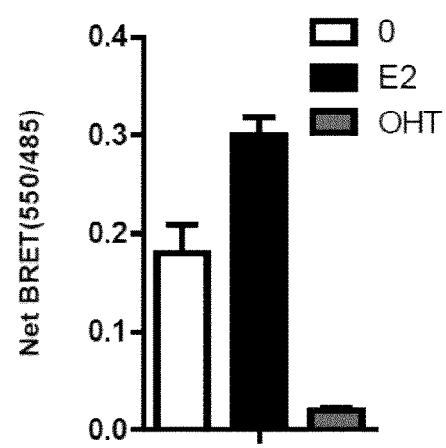
(FIG. 5B) BRETFect signals (Delta BRET D+I+A−[(D+I)+(D+A)] indicate that OHT suppresses coactivator motif recruitment to ERα dimers.

As a proof of concept, the agonist-dependent recruitment of AF2-binding CoApep tagged with Venus by homo- and hetero-dimers of nuclear receptors ERα and ERβ, tagged with RLucII and mTFP1 (10,25,26) was monitored (FIG. 5A). The corresponding expression vectors were cotransfected into HEK293 cells. Spectral analyses of the various complexes validated the combined energy transfer between D, I and A in presence of the agonist 17β-estradiol (E2) (FIG. 4B). RLucII produced a broad emission peak with a maximum at 484 nm (FIG. 4B, full black line). A red shift in the maximal emission peak to 492 nm combined with a dip in emission around 464 nm in "ERα-RLucII+ERα-mTFP1" versus "ERα-RLucII alone" indicated that energy was efficiently transferred between D and I. A potentiation of the A emission around 528 nm could be observed when ERα-mTFP1 was added to ERα-RLucII+CoApep-Venus complex (FIG. 4B). The differential emission plot representing the emission of the ternary complex (D–I–A) minus that of the binary complex between ERα-RLucII and CoApep-Venus (D-A) (FIG. 4C) illustrates the significant signal drop centered at 464 nm, due to energy absorption by mTFP1, and the corresponding increase in signal with a maximum at 528 nm, compatible with energy transfer from mTFP1 to Venus (Table III). These results confirm the predicted pattern of energy transfer and amplification in BRETfect.

Figure 5C:
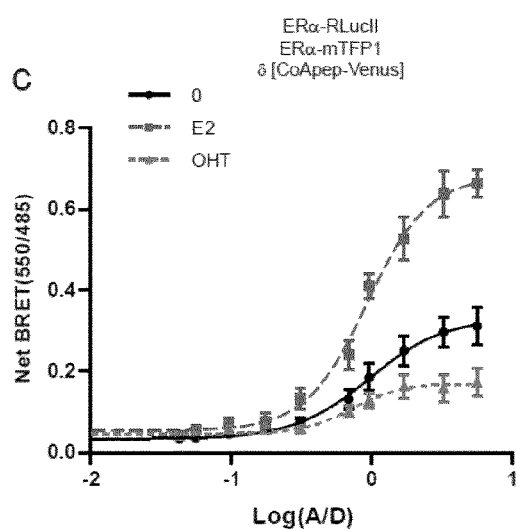
(FIG. 5C) ERα dimer interaction with CoApep-Venus is concentration-dependent and saturable.
Figure 5D:
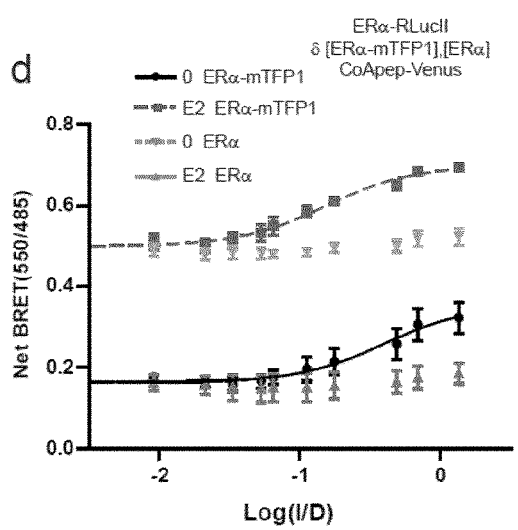
(FIG. 5D) BRETFect amplification is dependent on ERα-mTFP1 concentration. Graphs are representative of 3 biological replicates and error bars represent the SEM. * $p<0.01$, Bonferroni-test post-hoc ANOVA.
Figure 6:
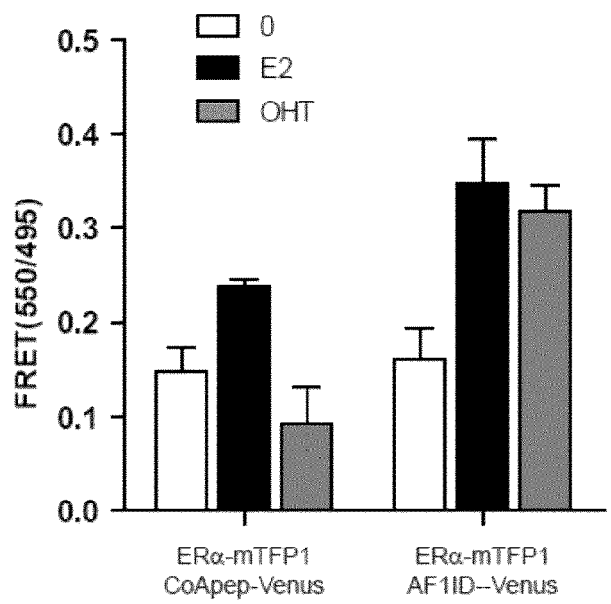
FIG. 6—FRET between the intermediate and acceptor monitors the interaction of the corresponding proteins. HEK293 cells were transfected with ERα-mTFP1 and CoApep-Venus or AF1ID-Venus and treated with ligands or DMSO (Ve) for 45 minutes. Measurements of raw FRET ratios (550 nm/495 nm). Values reported are the average of three biological replicate composed of three technical replicate each. Error bars represent SEM.

BRET ratios for the binary and ternary complexes in the presence of E2 or of the antiestrogen 4-hydroxytamoxifen (OHT) were monitored, the latter being permissive for ER dimer formation but repressing coactivator recruitment (27, 28). In the control ERα-RLucII+CoApep-Venus condition, treatment with E2 produced a robust BRET signal, reflecting complex formation, while OHT decreased basal CoApep recruitment (FIG. 5A). Cotransfecting ERα-mTFP1 significantly increased BRET levels in the presence of E2 or the absence of treatment (FIG. 5A). Transfer between ERα-RLucII and ERα-mTFP1 in the absence of CoApep-Venus produced only small BRET signals under all treatment conditions (FIG. 5A), as the larger part of the emission spectrum of mTFP1 is not detected in the 550 nm channel. Thus, the BRET amplification observed in the ternary condition is due to energy transfer from ERα-mTFP1 to CoApep-Venus and not to emission of ERα-mTFP1 at 550 nm. Interaction between ERα-mTFP1 and CoApep-Venus could be verified by FRET after direct excitation of mTFP1 (FIG. 5). The differential BRET activity observed between the three partner condition and the sum of those observed with the acceptors separately in control transfections (delta BRET, FIG. 5B) provides evidence for efficient coactivator recruitment to ERα dimers assembled in the presence or absence of E2, but not in the presence of OHT. Non ERα-dimerizing proteins fused to mTFP1 failed to amplify BRET, and a non ERα-interacting mutated peptide yielded only residual BRET signal FIG. 7). The BRET levels in the ternary condition were dependent on the concentration of CoApep-Venus and were saturable under all treatments, as expected for a specific interaction (FIG. 5C). Signal amplification increased with the concentration of ERα-mTFP1, but not of untagged ERα (FIG. 5D). Together, these results indicate that addition of the Intermediate yields an increase in BRET signal that is dependent on its presence in a ternary complex.

Figure 8A:
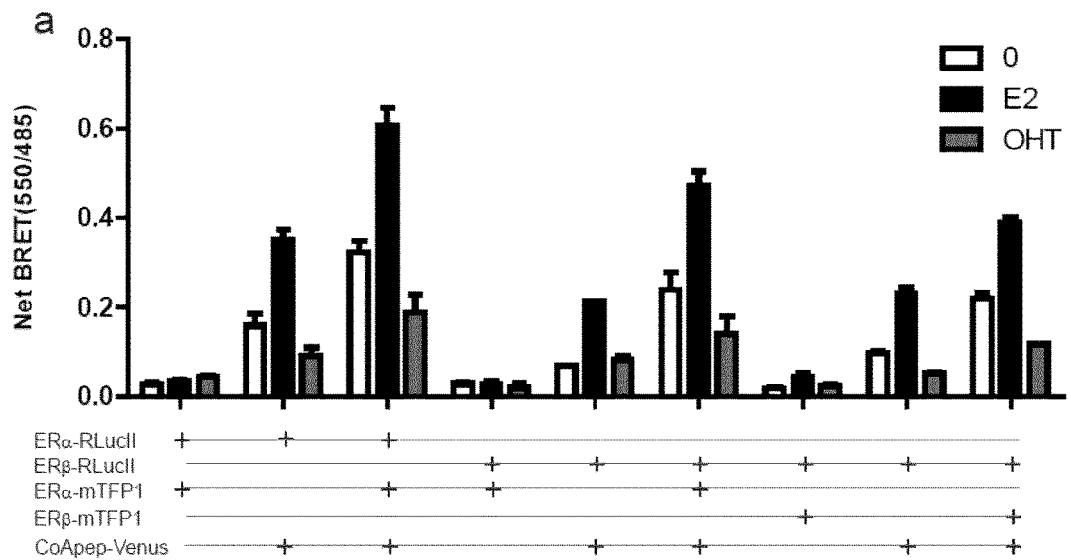
(FIG. 8A) Ligand-dependent recruitment of CoApep to ERα and ERβ homodimers and to ERα/ERβ heterodimers. Cells were transfected with indicated constructs and treated as in FIG. 5A. Ternary signal detected from different complexes are compared to the binary components, Donor+Intermediate and Donor+Acceptor.
Figure 8B:
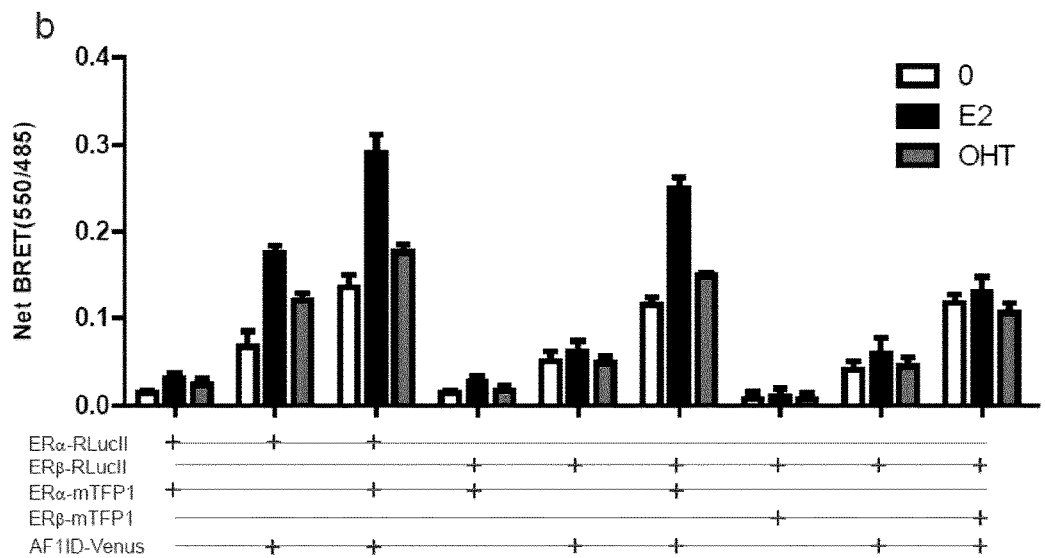
(FIG. 8B) Ligand-dependent recruitment of AF1ID to ERβ dimers require the presence of ERα. Cells were transfected with indicated constructs and treated as in FIG. 5A.
Figure 9A:
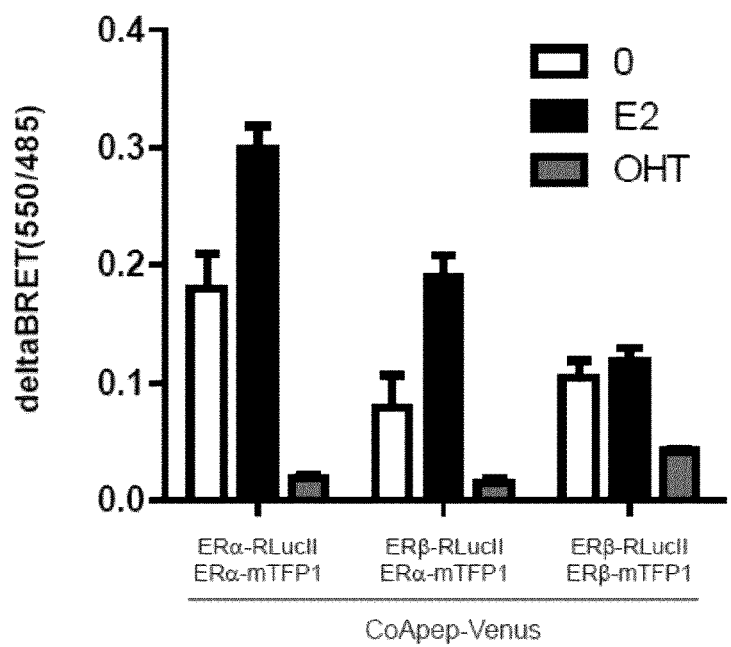
FIG. 9—BRETFect assays detects formation of dimer-dependent ternary complexes (FIG. 9A) Calculated ternary signal from BRETFect assays of ER dimers and CoApep. Signals from FIG. 9A were treated as in FIG. 5B to obtain net ternary signal (deltaBRET).
(FIG. 9B) Calculated ternary signal from BRETFect assays of ER dimers and AF1ID.
(FIG. 9C) Calculated ternary signal from BRETFect assays of ER dimers and SUMO3.
Figure 9B:
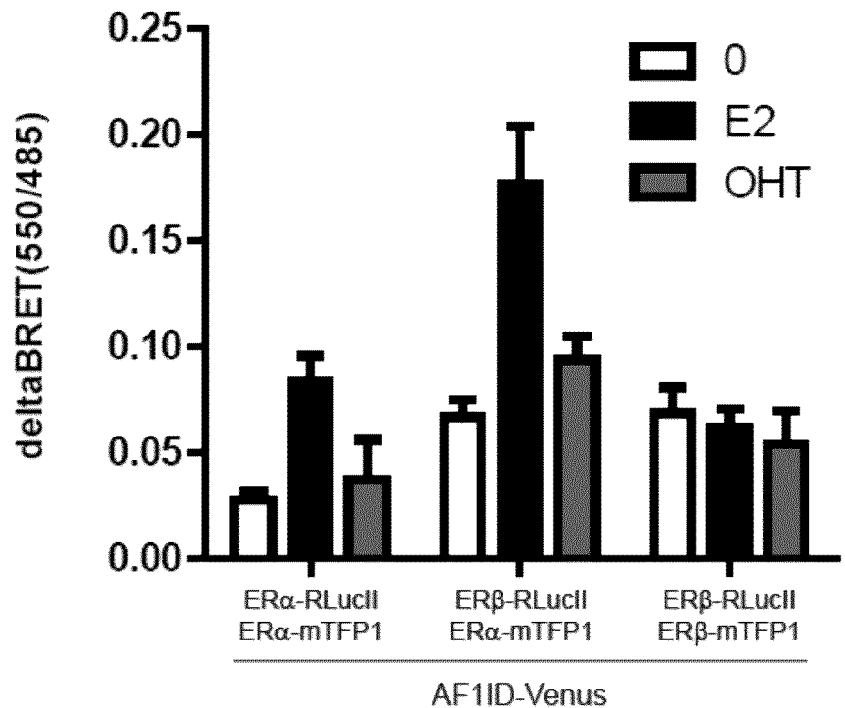

Example 5: Ligand-Induced Recruitment of the AF1-Interaction Domain and SERD-Dependent SUMOylation are Specific to ERα-Containing Dimers Both ERα and ERβ recruited CoApep-Venus in an E2-induced, OHT-repressed manner in BRET assays (FIG. 8A). Signal potentiation for recruitment of CoApep-Venus was observed by addition of ERα-TFP or ERβ-TFP (FIG. 9A). On the other hand, contrary to ERα, recruitment of the AF1ID by ERβ was not stimulated by ligand, (FIG. 8B) and was potentiated by co-transfection of ERβ-RLucII in a ligand-independent manner (FIG. 9B), consistent with previous reports (17). On the other, cotransfection of ERα-RLucII potentiated complex formation with the AF1-interacting domain in the presence of E2 more than in the absence of ligand or the presence of OHT, restoring agonist-stimulated recruitment. This result is compatible with the previous observation that the AF1 region of ERα contributes to transactivation in ER heterodimers as well as in ER homodimers (17).

Figure 8C:
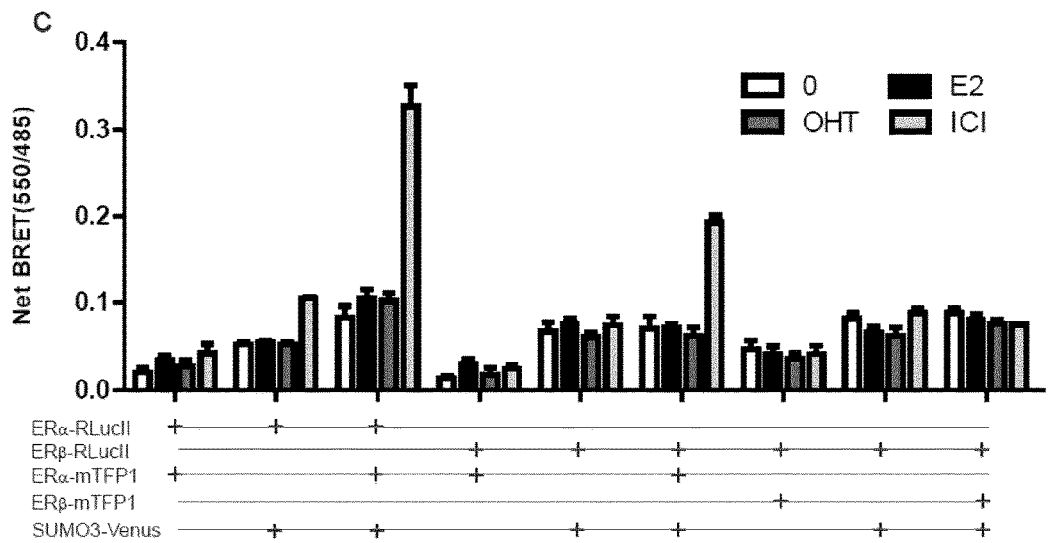
(FIG. 8C) The presence of ERα in a dimer complex is necessary for SERD induced SUMOylation. Cells were transfected with the indicated constructs and treated for 2 hours with 100 nM E2, OHT or ICI182,780.
Figure 9C:
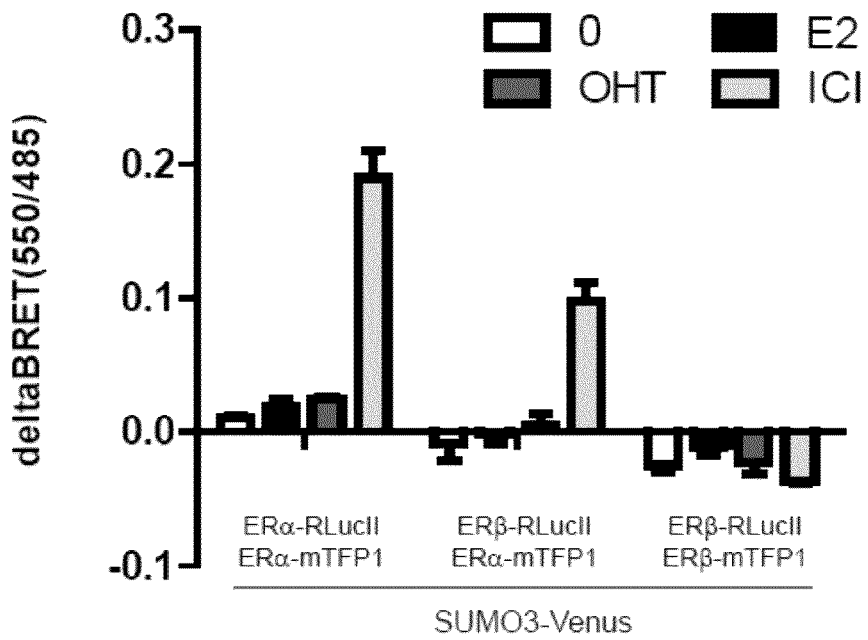

The impact of SERDs on ERβ SUMOylation was not previously addressed. In BRET assays, SERDs did not induce BRET signals between SUMO3-Venus and ERβ, contrary to ERα (FIG. 8C). Cotransfection of ERα-TFP potentiated the signal obtained in the presence of SERDs for both ERα-RLucII and ERβ-RLucII, while cotransfection of ERβ-TFP did not potentiate the basal signal obtained with ERβ-RLucII (FIG. 9C), indicating that the presence of at least one molecule of ERα is required for SUMOylation to take place in a SERD-induced manner.

Figure 10A:
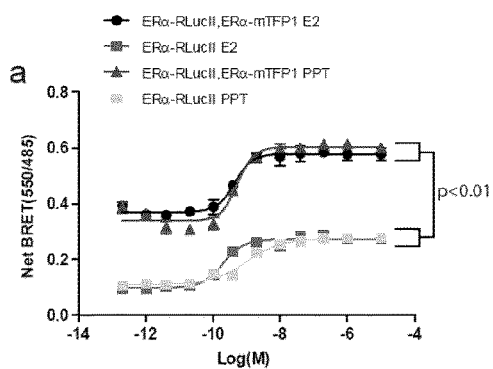
(FIG. 10A-F) HEK293 cells were transfected with indicated receptors fused to RLucII or mTFP1 and with CoApep-Venus (FIG. 10A-B, C-D) or SRC1-RID-Venus (FIG. 10E-F).
Figure 10B:
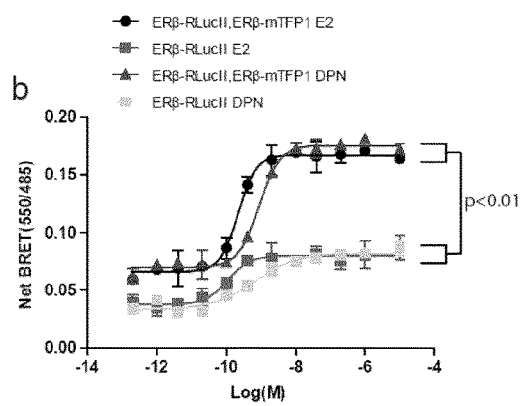
Figure 10C:
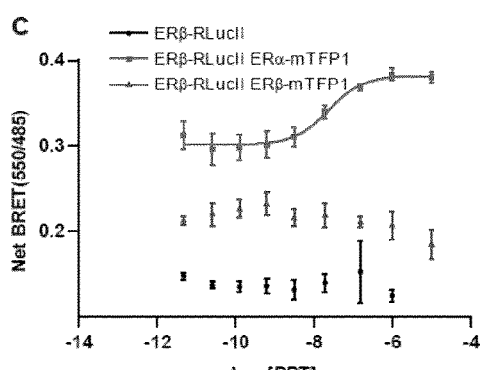
Figure 10D:
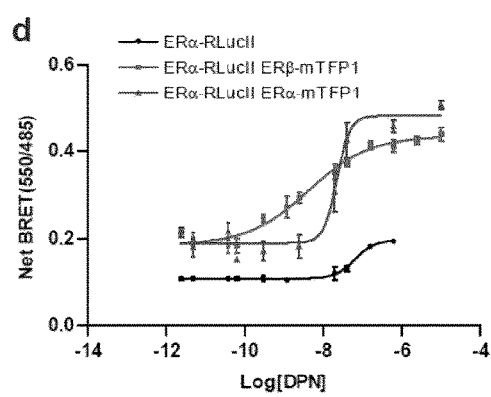
Figure 10E:
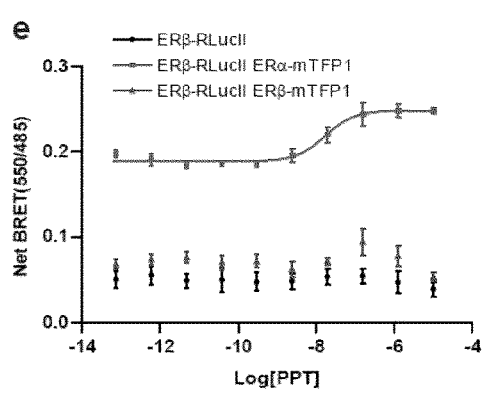
Figure 10F:
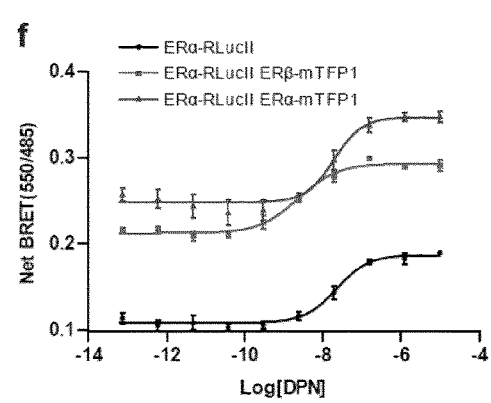
Figure 11A:
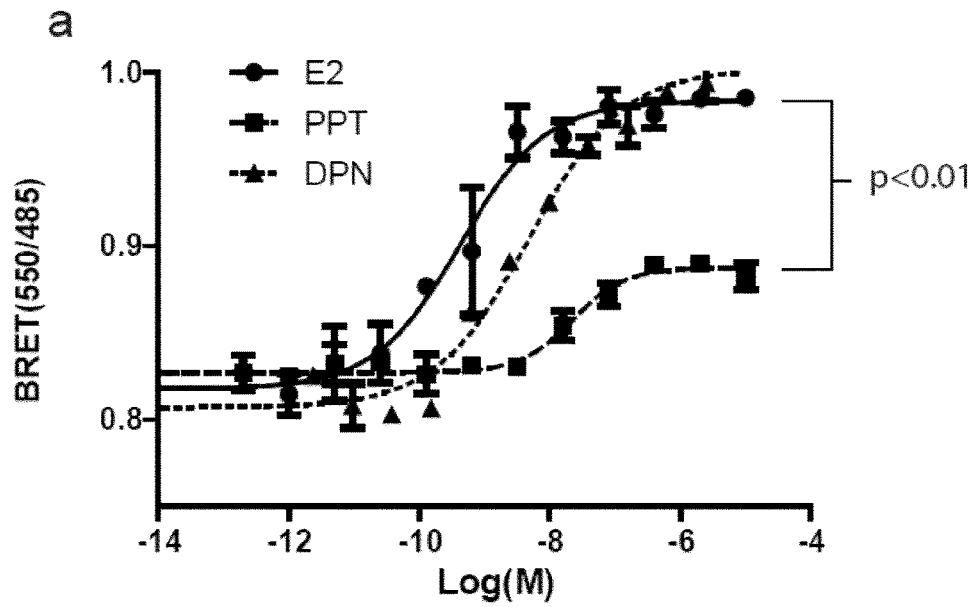
FIG. 11—Comparison of CoApep (FIG. 11A) or SRC1-RID (FIG. 11B) recruitment by ERα-ERβ heterodimers in the presence of E2, PPT or DPN. Experiment was carried out as in FIG. 10 in the trimeric condition. BRET ratios are displayed for ERβ-ERα heterodimer recruitment of CoApep-Venus (FIG. 11A) or SRC1-RID-Venus (FIG. 11B) in the presence of varying concentrations of each ligand. While PPT reaches only 50% of the BRETmax observed with E2 or PPT for CoApep recruitment, it is not significantly weaker for SRC1-RID recruitment. P-value was obtained through Student's t-test.
Figure 11B:
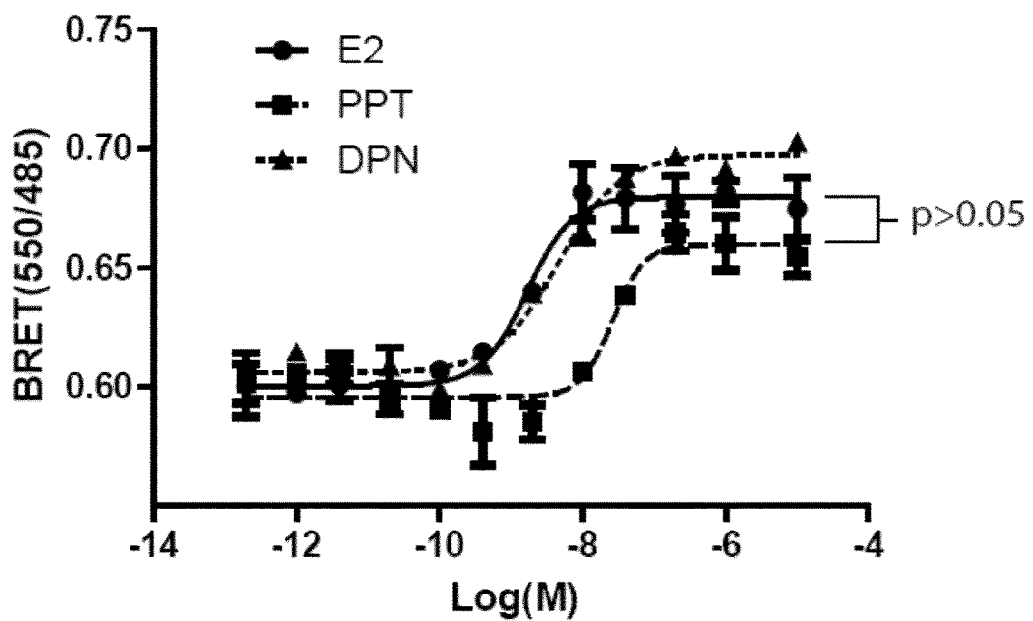
Figure 12A:
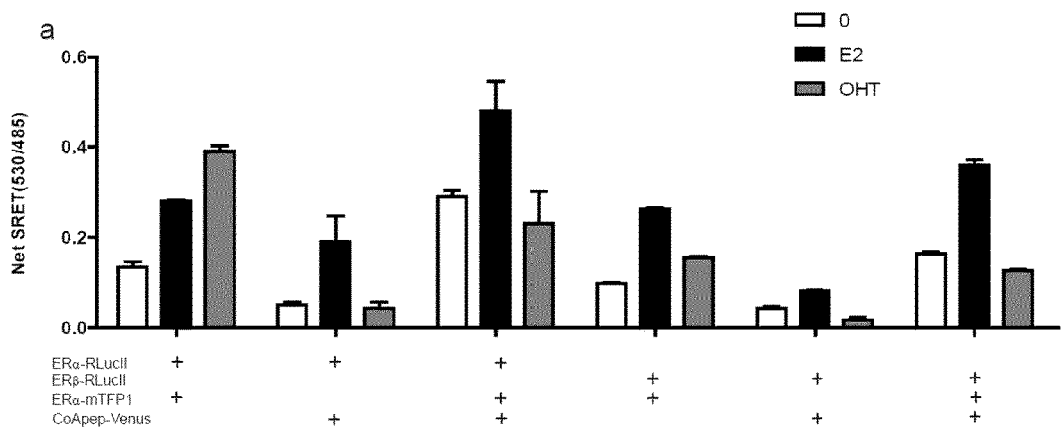
FIG. 12—Combined transfer between components of the ERα-ERα-CoApep trimer (FIG. 12A) SRET measurements performed as described in (1) for ERα-ERα or ERα-ERβ recruitment of the coactivator motif. Note the detection of direct transfer from the Donor to the Acceptor as well as from Donor to Intermediate, invalidating use of SRET for these complexes (FIG. 12B) Net trimer signals were calculated from measurements in FIG. 12A and represent the delta BRET (550/485) for BRETFect assays and similarly the delta BRET (530/400) for SRET assays. Calculation of the DeltaBRET using the SRET measurements leads to much smaller signals than with the BREFect set-up. Displayed graphs were prepared from one representative biological replicate with 4 technical replicates; error bars represent the standard deviation.
Figure 12B:
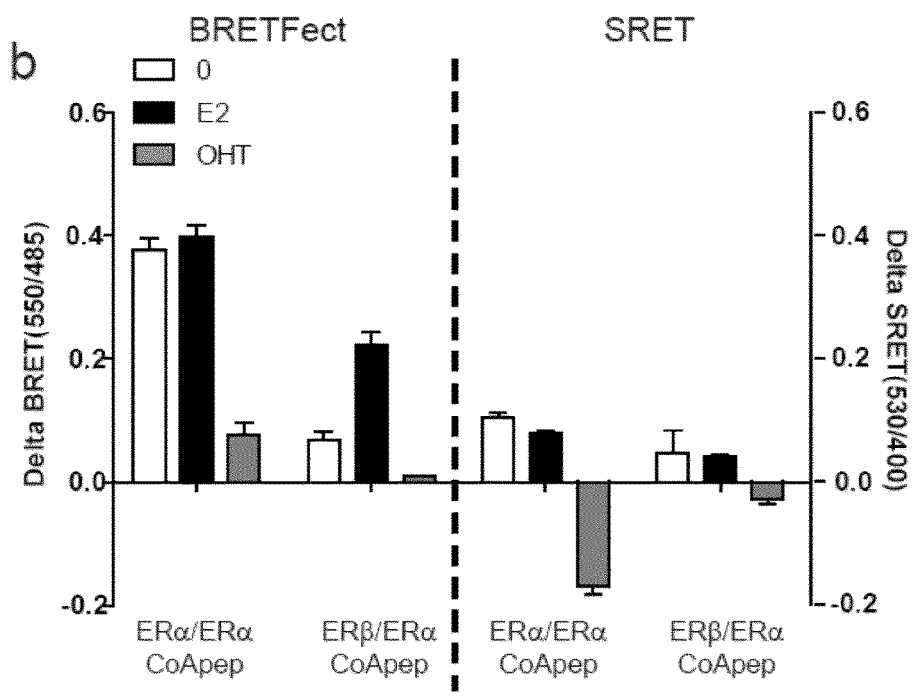

Example 6: Monitoring Activation of ER Homo- and Hetero-Dimers by Receptor-Selective Ligands Using BRETFect assays for recruitment of CoApep-Venus by different combinations of ERα and ERβ fused to RLucII or mTFP1 (see above), it was tested whether the ERα-specific agonist propylpyrazole triol (PPT) or the ERβ-selective agonist diarylpropionitrile (DPN) (29-31) can lead to heterodimer activation. PPT activated ERα, but not ERβ homodimers (FIGS. 10A and C). Further, the addition of ERα-mTFP1 to ERβ-RLucII led to a PPT-stimulated coactivator recruitment (FIG. 10C), indicating activation of the ERα-ERβ heterodimer. Interestingly, PPT had less potency for coactivator recruitment by the ERα-ERβ heterodimer than by the ERα homodimer ($EC_{50}$ 28 vs 0.5 nM, Table IV), suggesting differential allosteric effects between homo- and heterodimeric partners. On the other hand, DPN induced recruitment of the CoApep preferentially ERβ over ERα homodimers (FIGS. 10B and D) with a 20-fold difference in $EC_{50}$s, and activated ERα-ERβ heterodimers (FIG. 10D) with an intermediate $EC_{50}$ value (Table IV). Assays performed with the SRC1 receptor-interacting-domain (RD), which contains multiple CoApep-like interacting motifs, confirmed that PPT and DPN promoted recruitment of the entire RID to the heterodimer with lower potency compared to homodimers (FIG. 10E-F, Table V). Further, titration curves indicate that while the recruitment capacity for CoApep was reduced by half in the heterodimer with PPT, which binds only ERα, compared to E2 or DPN, which bind both heterodimeric partners, this was not observed for the RD, consistent with the reported stoichiometry of two coactivator peptides but only one RID per dimer (FIG. 11) (32).

TABLE IV

Allosteric effects of heterodimeric partners for recruitment of the coactivator motif peptide revealed by BRETfect titration curves with receptor-selective ligands. EC50s are taken from displayed curves of FIG. 10. Note that titration curves using inverted tagging of LucII and mTFP1 for the heterodimers yielded similar results. Data are the average of three biological replicates.

| Ligands | EC50 (nM) (95% confidence interval) | | |
|---|---|---|---|
| | ERα-ERα | ERα-ERβ | ERβ-ERβ |
| E2 | 0.341 (0.255 to 0.481) | 0.419 (0.214 to 0.822) | 0.469 (0.222 to 0.831) |
| PPT | 0.547 (0.421 to 2.22) | 28.4 (10.3 to 38.6) | n/a |
| DPN | 20.1 (15.2 to 40.4) | 5.11 (2.76 to 11.8) | 1.02 (0.196 to 2.12) |

TABLE V

Allosteric effects of heterodimeric partners for recruitment of SRC1-RID revealed by BRETfect titration curves with receptor-selective ligands. EC50s are taken from displayed curves of FIG. 10. Note that titration curves using inverted tagging of LucII and mTFP1 for the heterodimers yielded similar results. Data are the average of three biological replicates.

| Ligands | EC50 (nM) (95% confidence interval) | | |
|---|---|---|---|
| | ERα-ERα | ERα-ERβ | ERβ-ERβ |
| E2 | 0.404 (0.268 to 0.784) | 0.503 (0.109 to 2.65) | 0.218 (0.166 to 0.286) |
| PPT | 0.968 (0.729 to 1.18) | 25.1 (7.43 to 84.7) | n/a |
| DPN | 69.7 (35.1 to 447) | 17.6 (4.12 to 22.3) | 0.757 (0.318 to 1.80) |

Example 7: BRETfect Vs. SRET

Figure 7:
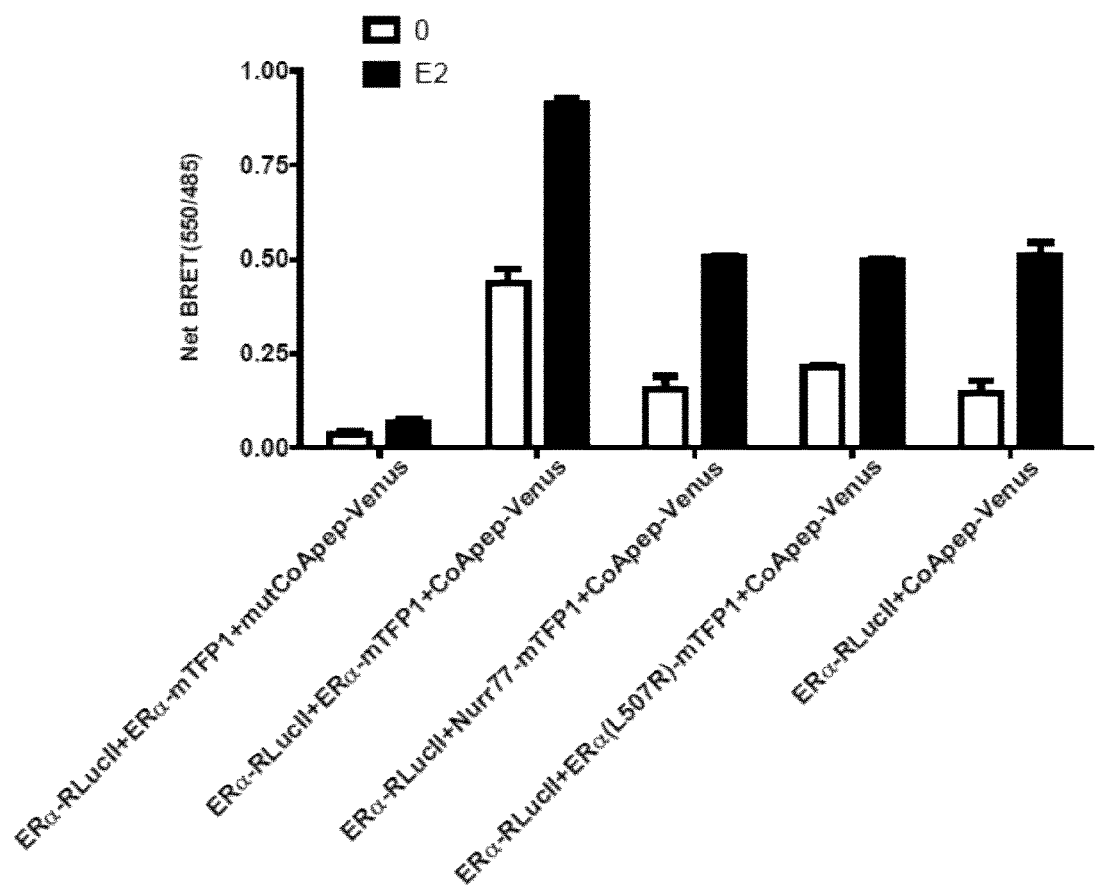
FIG. 7—Specific interactors are required to achieve BRETFect. Experiment was carried out as in FIG. 5A but with control versions of the Intermediate, where ERα was substituted for either the non-interacting partners Nur77-mTFP1 or the dimerization mutant ERα (L507R), and of the Acceptor, in which CoApep was replaced by a mutant that cannot interact with ERα due to mutation of the LXXLL motif to AXXAA.
Figure 14A:
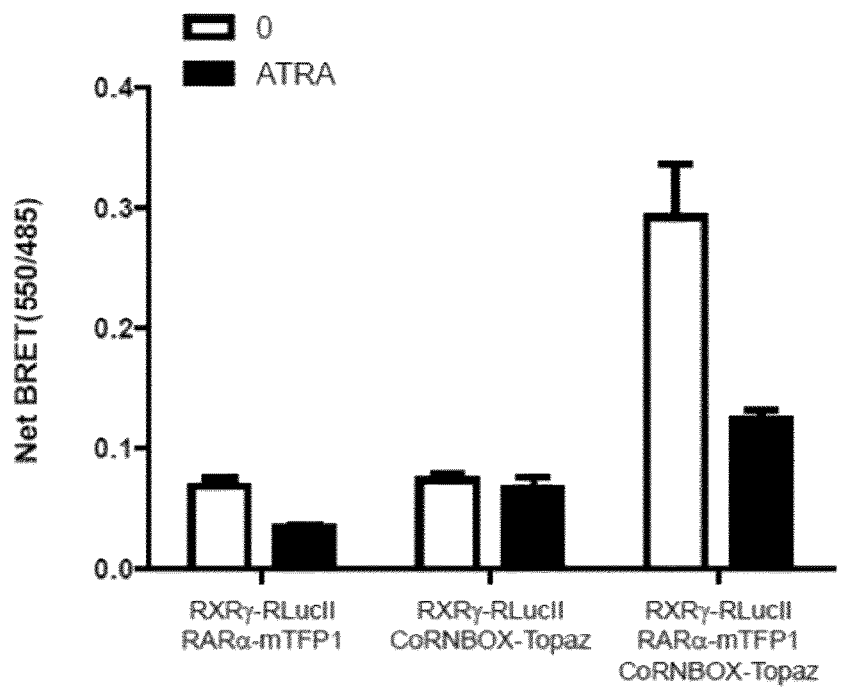
FIG. 14 shows BRETFect can be used to monitor the activity of other NRs such as in this case RXRγ and RARα forming a ternary complex with the corepressor motif peptide CoRNRBox. Panel A shows that in absence of treatment, the RXRγ-RARα-CoRNBox complex is formed but upon treatment with all-trans retinoic acid (ATRA 1 µM), the CoRNBox peptide is released from RARα and the ternary complex is disassembled as indicated by the drop in the net BRET. BRETFect signals (delta BRET) are shown in panel B. HEK293 cells were transfected with expression vectors encoding RXRγ-RLucII (D) and RARα-mTFP1 (I) or CoRNBox-Topaz (A) or both. Cells were treated for 40 min with vehicle DMSO (0) or all-trans retinoic acid (ATRA) before coelenterazine H addition and BRET measurement.
Figure 14B:
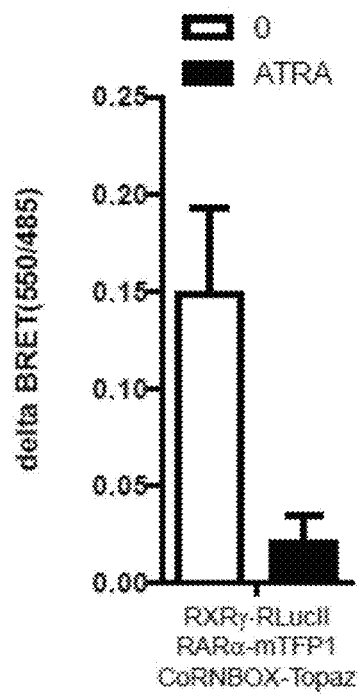
Figure 15A:
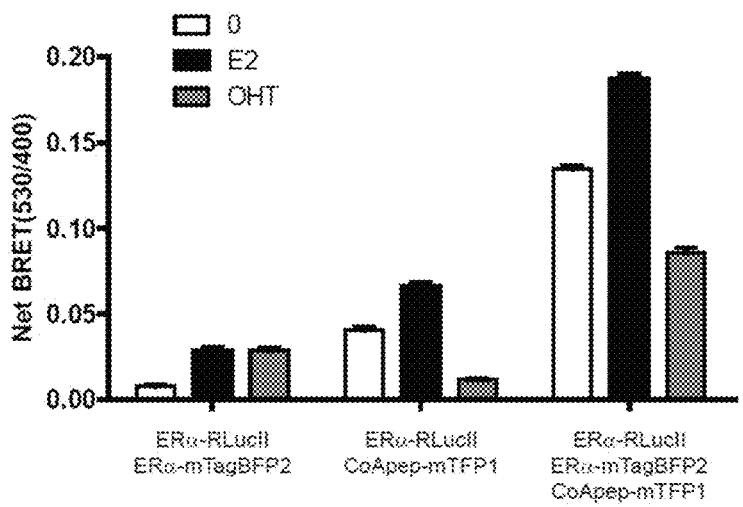
FIG. 15A shows the net BRET signal and FIG. 15B the deltaBRET signal (530/400 nm). This new embodiment also creates the BRETFect effect by amplifying mTFP1 emission when mTagBFP2 is part of the ternary complex.
Figure 15B:
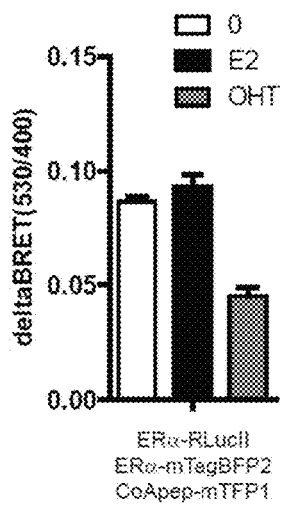
FIG. 15 shows another embodiment of a suitable combination of D, I and A in accordance with the present invention: In this embodiment, *Renilla* Luciferase (RLucII-coel400) is the Luciferase (D), mtagBFP2 (PDB) is the I and mTFP1 is the A (with measures at 400 and 530 nm). Protein tags fused to D, I and A are distributed as in FIG. 4. Experiment was carried out as in FIG. 6A-D.
Figure 16A:
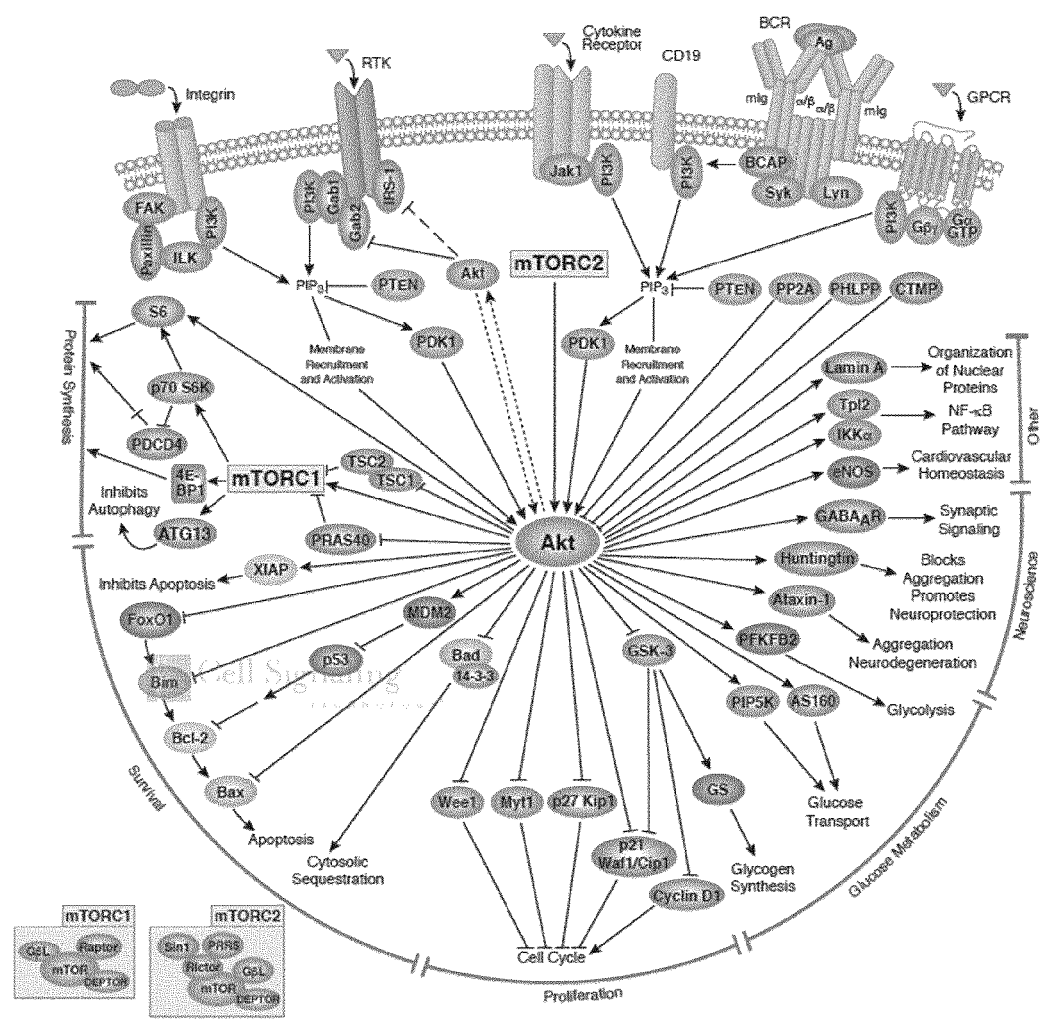
FIG. 16A shows a schematic representation of the PI/kinase/Akt signaling pathway (adapted from Cell Signaling Technology®).
Figure 16B:
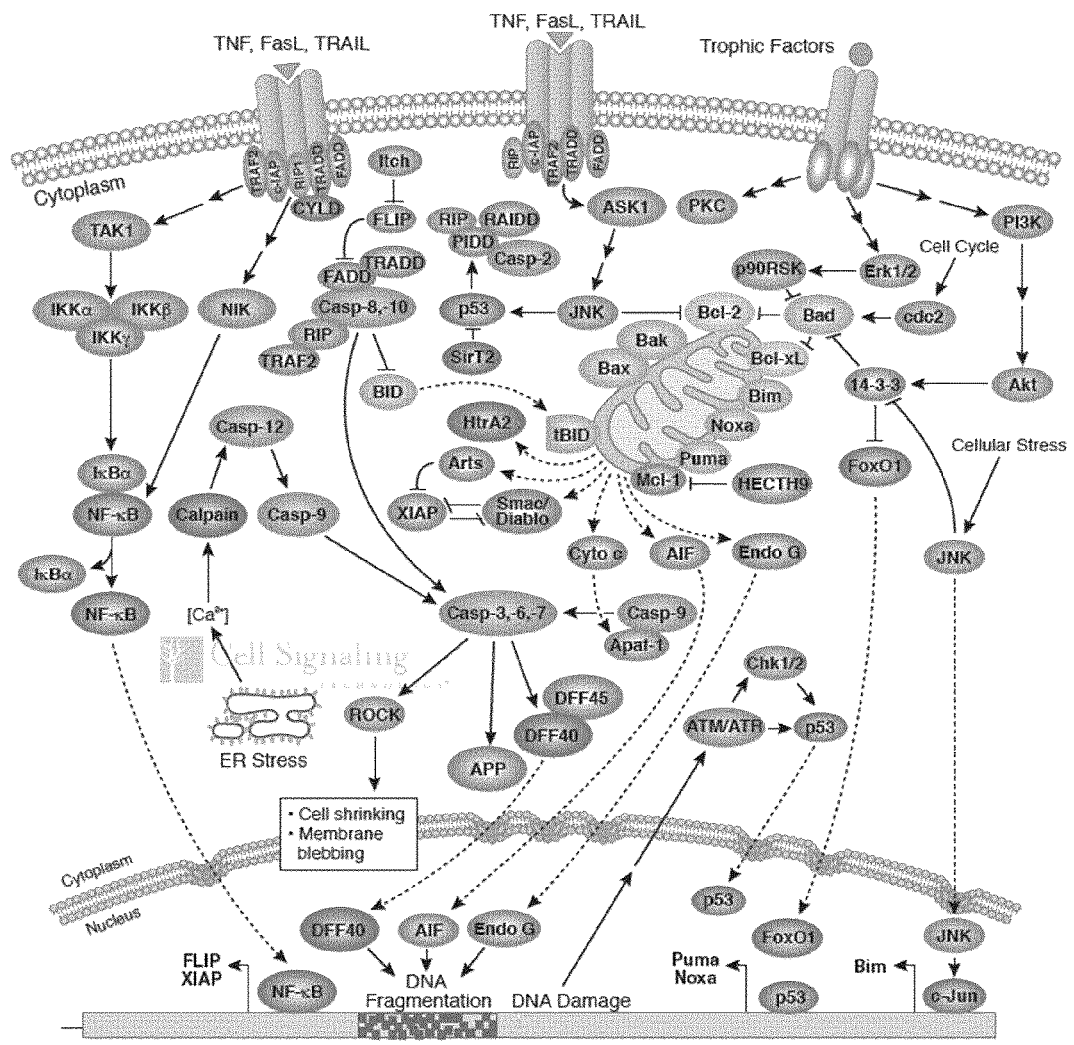
FIG. 16B shows a schematic representation of pathways involved in apoptosis regulation (adapted from Cell Signaling Technology®).
Figure 16C:
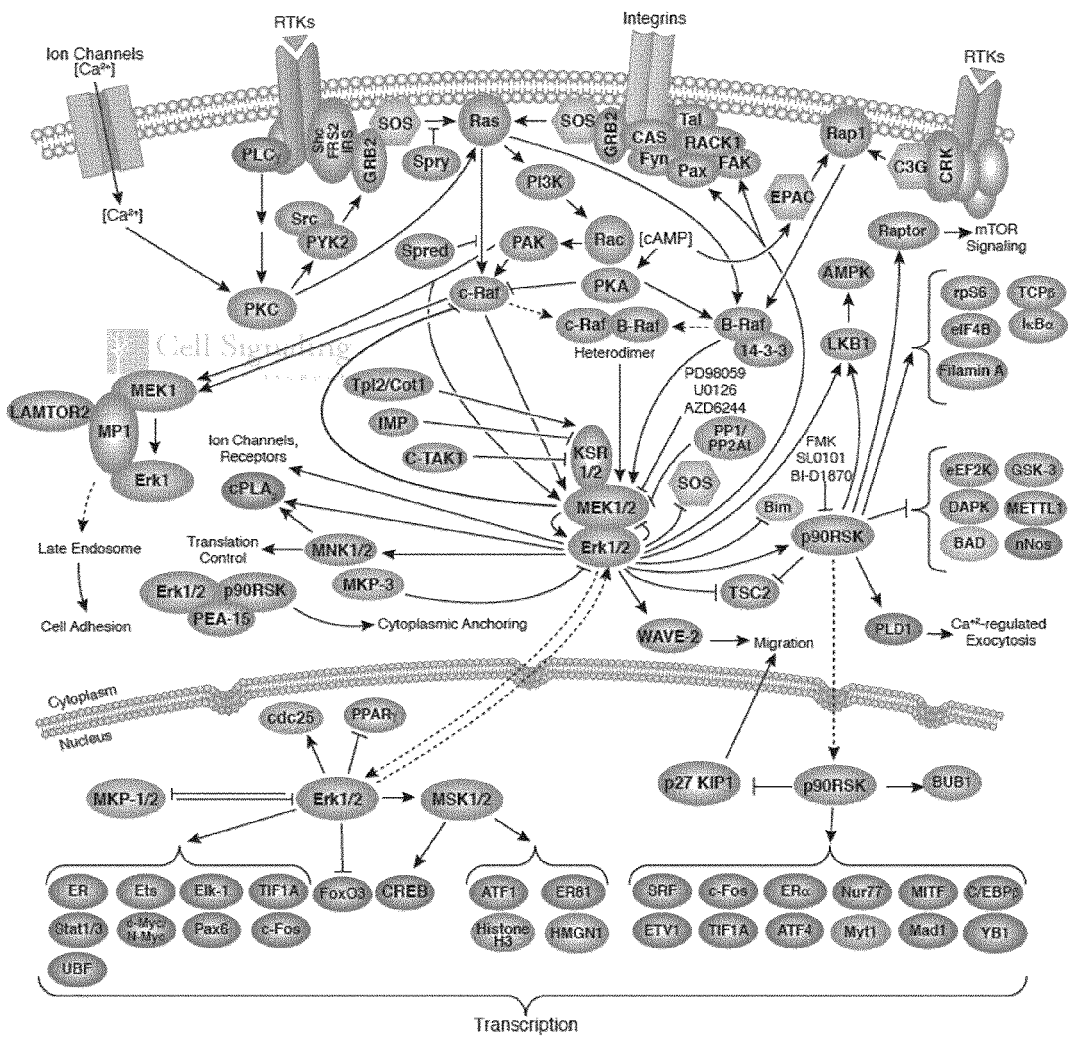
FIG. 16C shows a schematic representation of the MAPK/Erk pathway involved in cell growth and differentiation (adapted from Cell Signaling Technology®).
Figure 16D:
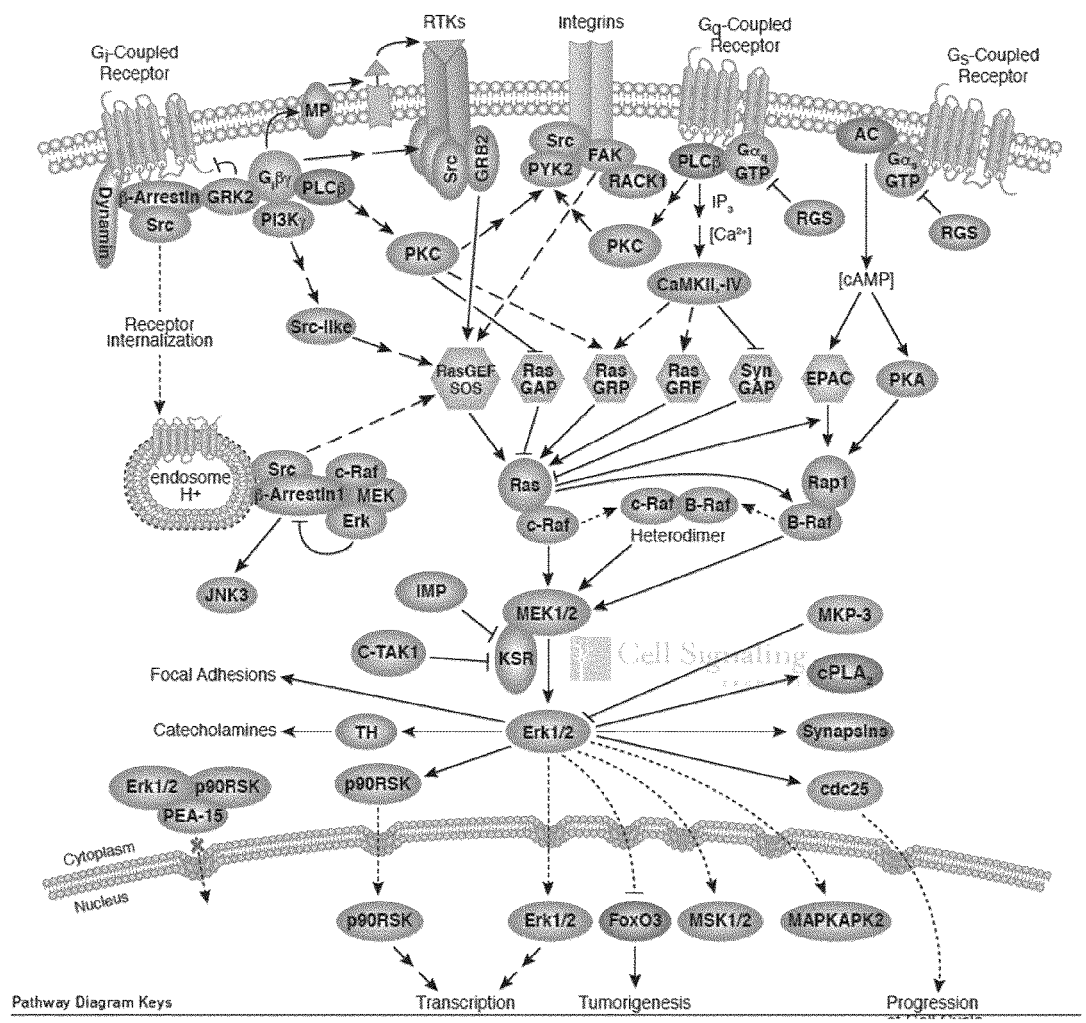
FIG. 16D shows a schematic representation of the G Protein-coupled receptors signaling to MAPK/Erk pathway (adapted from Cell Signaling Technology®).
Figure 16E:
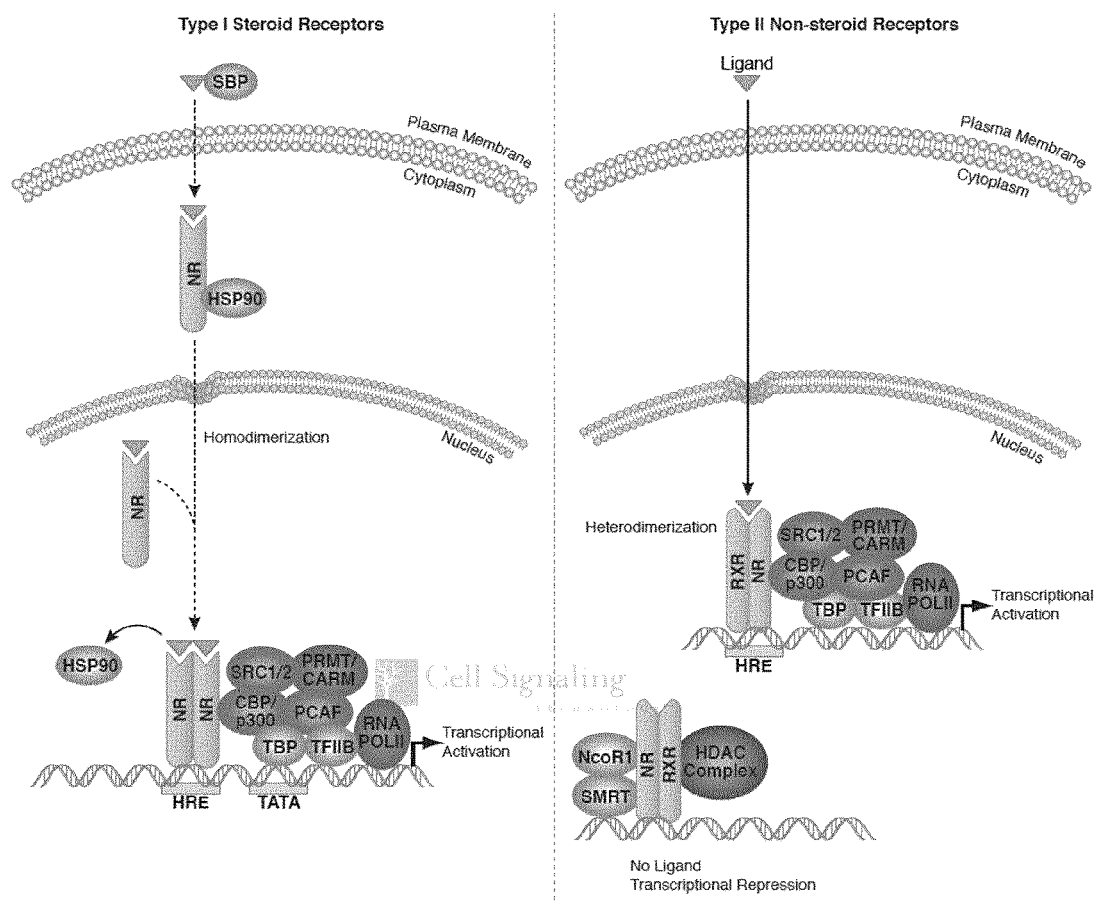
FIG. 16E shows a schematic representation of the nuclear receptor signaling pathway (adapted from Cell Signaling Technology®).
Figure 16F:
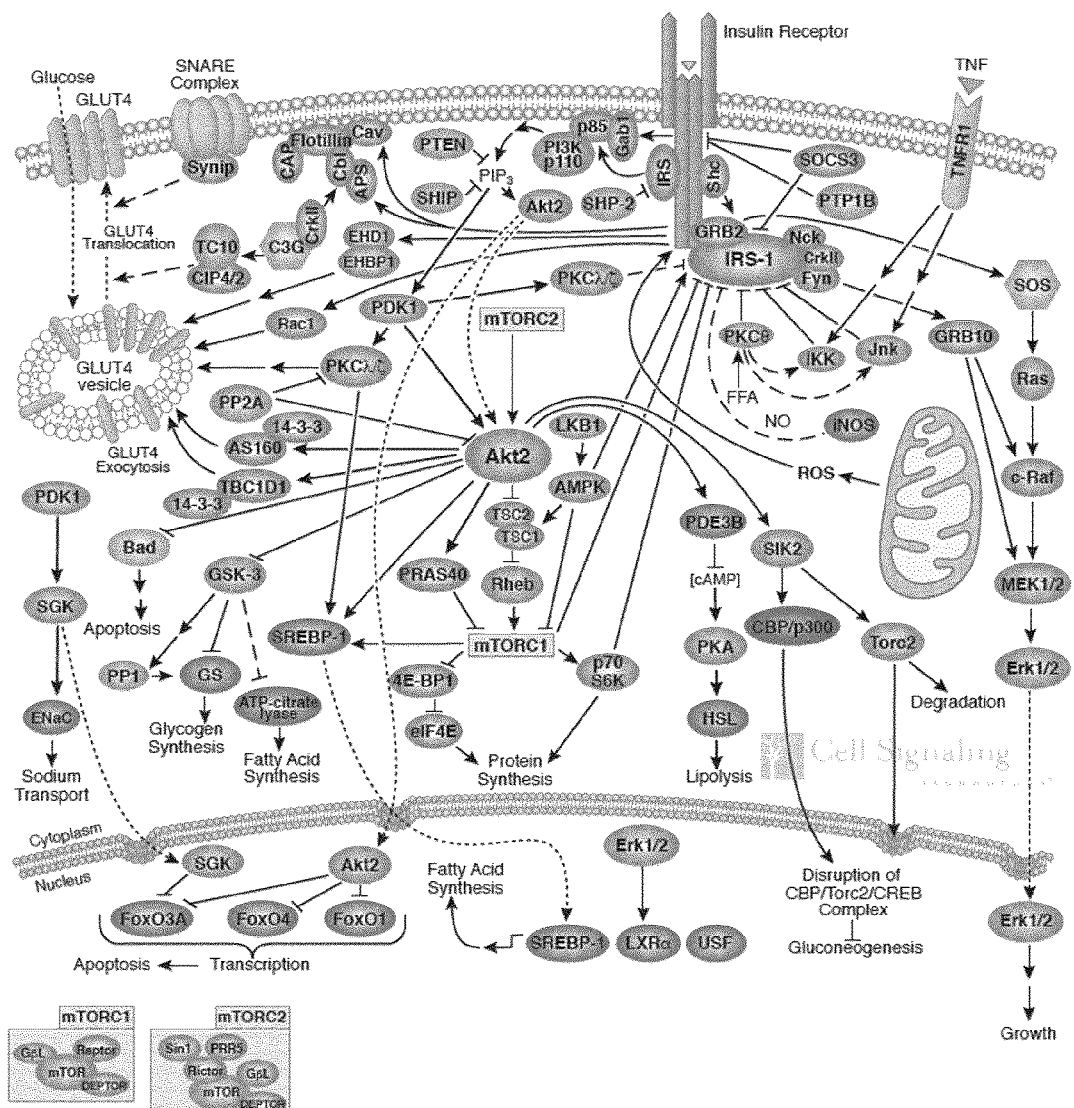
FIG. 16F shows a schematic representation of the insulin receptor signaling pathway (adapted from Cell Signaling Technology®).
Figure 16G:
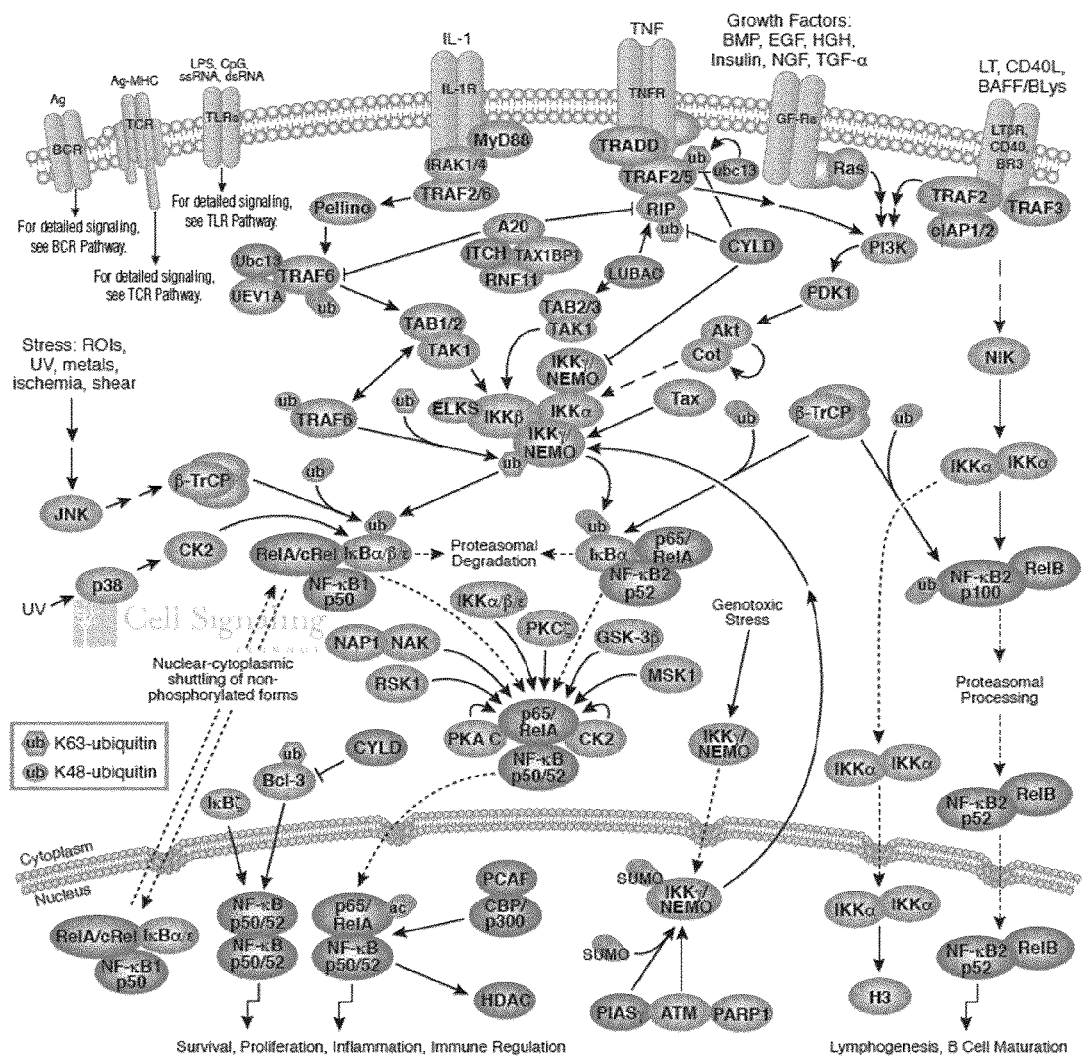
FIG. 16G shows a schematic representation of the NF-κB signaling pathway (adapted from Cell Signaling Technology®).
Figure 16H:
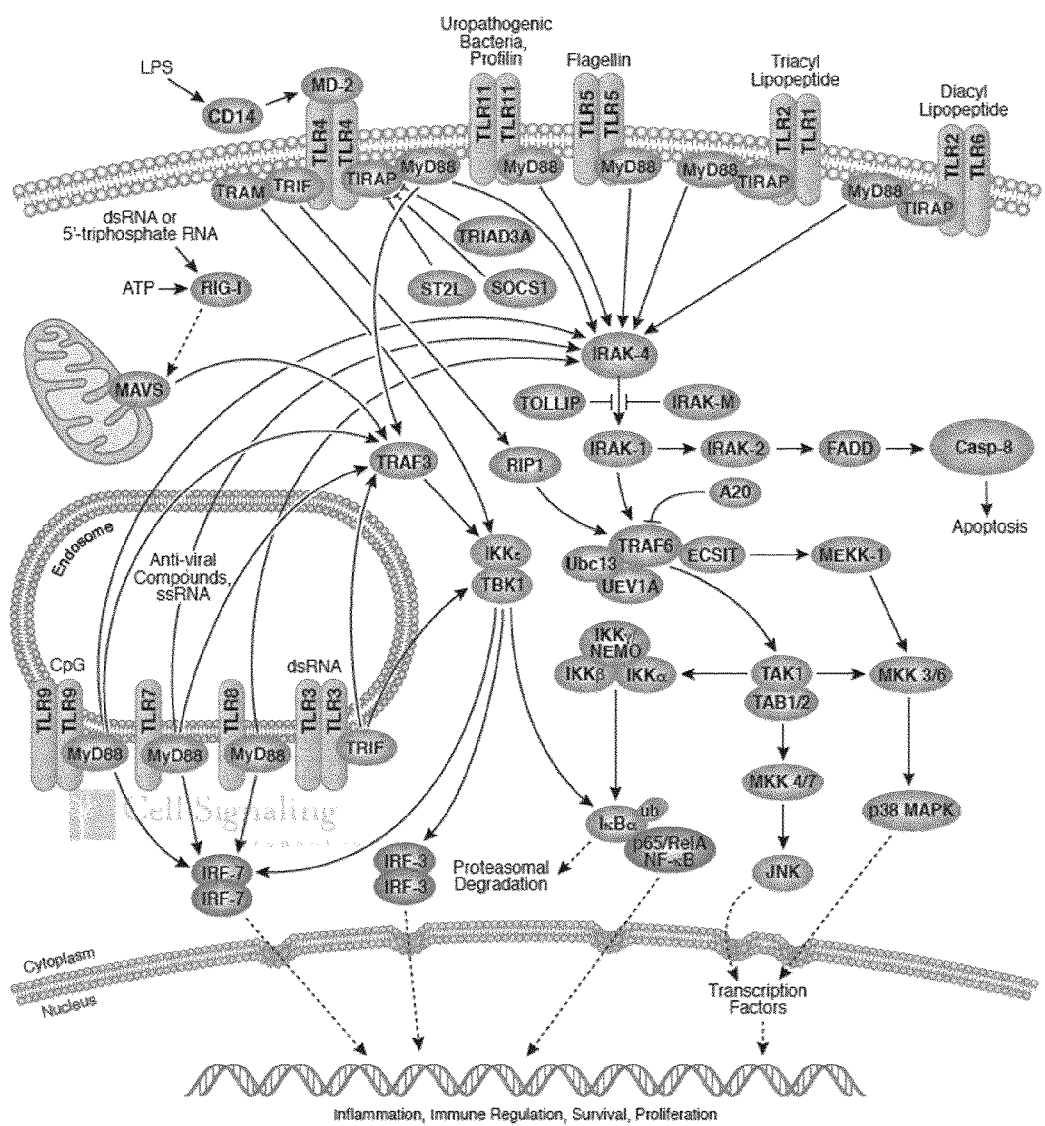
FIG. 16H shows a schematic representation of the Toll-like receptor (TLR) signaling pathway (adapted from Cell Signaling Technology®).
Figure 16I:
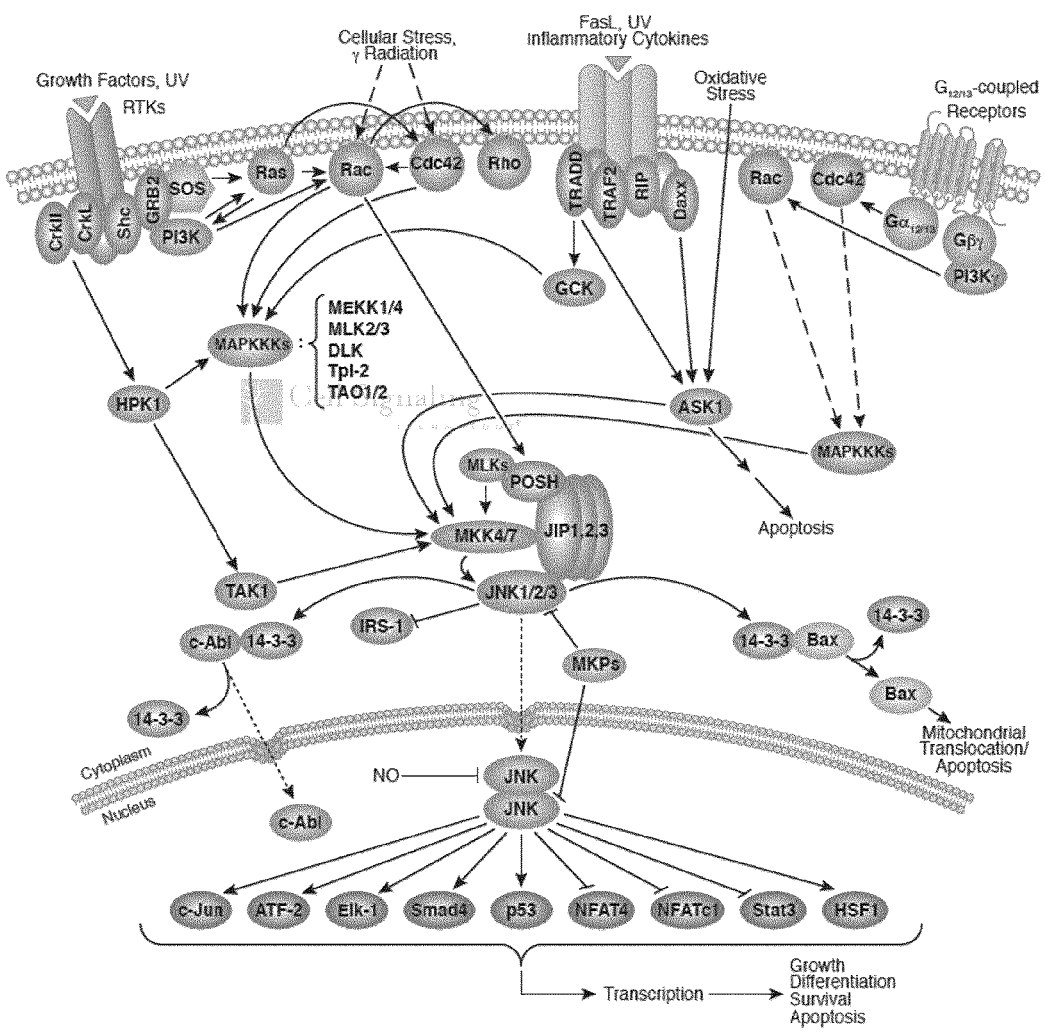
FIG. 16I shows a schematic representation of the SAPK/JNK signaling pathway (adapted from Cell Signaling Technology®).
Figure 16J:
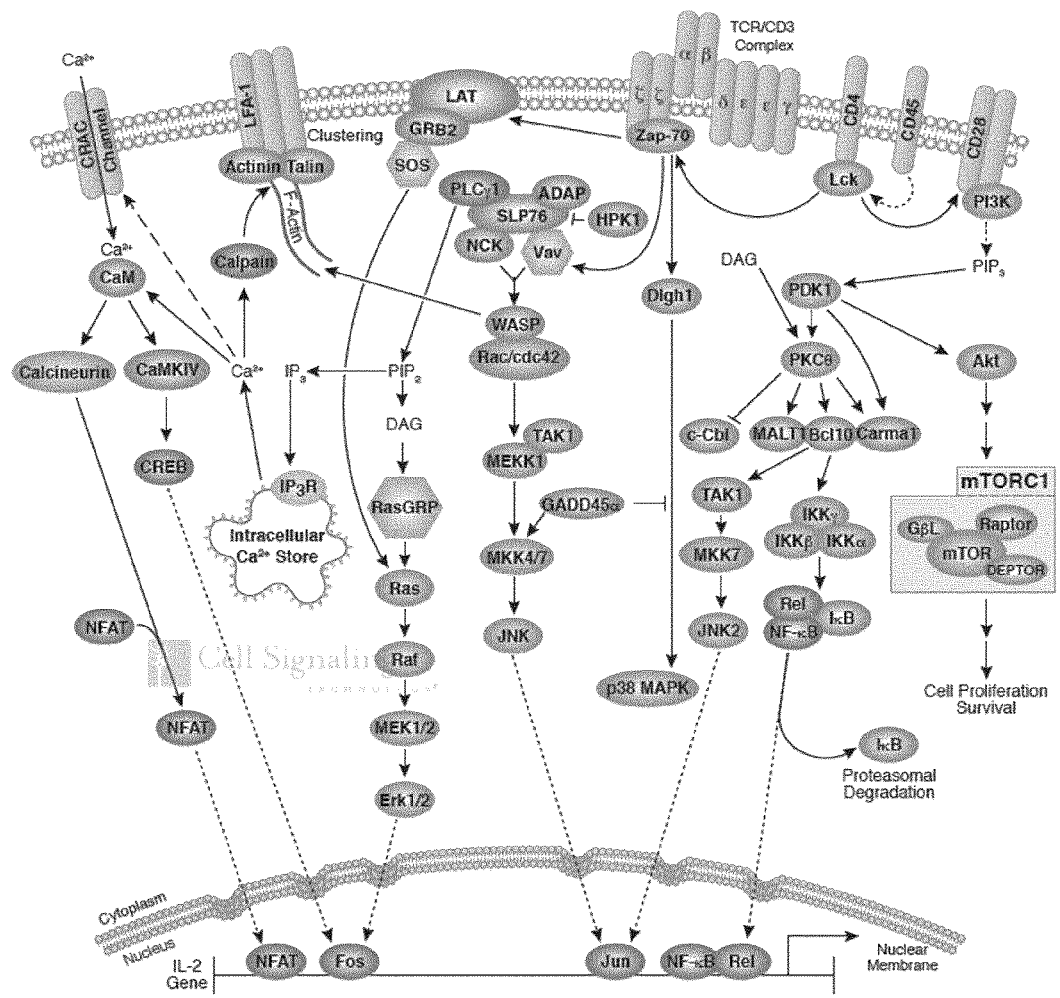
FIG. 16J shows a schematic representation of the T cell receptor (TCR) signaling pathway (adapted from Cell Signaling Technology®).

Serial resonance energy transfer (SRET) assays have been previously developed to address the detection of trimetric complexes. Similar to BRETfect, this approach involves a luciferase as donor and fluorescent proteins as Intermediate (uvGFP) and Acceptor (eYFP), but this approach posits an absence of direct transfer from D to A (see FIG. 1B). However, when a SRET protocol was used with the fusion proteins, some transfer from the Donor to the Acceptor was observed (FIG. 14). However, in BRETfect, the Intermediate (herein TFP) is chosen to optimize its capacity to relay emissions from the lower to the upper wavelengths in RLucII emission spectrum, while minimizing emission of the Intermediate in the Acceptor channel. The resulting effect of the presence of Intermediate partner in a trimeric complex is increased energy absorption by the Acceptor and, as a consequence, a net increase in Acceptor/Donor BRET signal compared to dimeric conditions. Use of non-interacting controls and of interacting proteins unfused to the Intermediate fluorophore (TFP) demonstrated the specificity of this potentiating effect for the presence of an Intermediate partner that interacts with the Donor (FIG. 7).

Example 8: BRETfect is Compatible with High-Throughput Screening

As screening methods are becoming readily available and encompass increasing numbers of natural and synthetic molecules, the possibility of targeting a specific trimeric complex, such as a nuclear receptor heterodimer in complex with a coactivator, in real-time in live cells should prove a tremendous asset. Discovery of dimer-selective nuclear receptor ligands is an important pharmacological opportunity (33-36) that necessitates development of robust assays for the activity of specific homo- and heterodimers. As shown in FIG. 13, the ERα-ERβ heterodimer activity assay was robust (Z-factor of 0.528), supporting the applicability of the method to high-throughput screening.

Example 9: Formation of a Ternary Complex Between RXRγ, RARα, and a Corepressor

The present inventors were also able to detect the formation of a ternary complex between RXRγ, RARα, and a corepressor (CoR) by using the BRETfect assay as described above. Results are presented in FIG. 16. Furthermore, FIG. 17 shows another embodiment of a suitable combination of D, I and A in accordance with the present invention: In this embodiment, *Renilla* Luciferase (RLucII-coel400) is the Luciferase (D), mtagBFP2 (PDB) is the I and mTFP1 is the A (with measures at 400 and 530 nm). Protein tags were distributed as in FIG. 4, the RXRγ-RARα, heterodimer replacing the ERα homodimer and the CoR replacing the CoA peptide. Experiment was carried out as in FIG. 5. This new embodiment also generates the BRETfect effect by amplifying mTFP1 emission when mTagBFP2 is part of the ternary complex.

Thus, inventors have demonstrated herein that BRETfect is a powerful tool to monitor formation of high order (e.g., ternary) complexes.

The scope of the claims should not be limited by the preferred embodiments set forth in the examples, but should be given the broadest interpretation consistent with the description as a whole.

REFERENCES

1. Carriba, P., Navarro, G., Ciruela, F., Ferre, S., Casado, V., Agnati, L., Cortes, A., Mallol, J., Fuxe, K., Canela, E. I. et al. (2008) Detection of heteromerization of more than two proteins by sequential BRET-FRET. Nat Methods, 5, 727-733.

2. Zhang, J. H., Chung, T. D. and Oldenburg, K. R. (1999) A Simple Statistical Parameter for Use in Evaluation and Validation of High Throughput Screening Assays. J Biomol Screen, 4, 67-73.

3. Rebois, R. V., Robitaille, M., Petrin, D., Zylbergold, P., Trieu, P. and Hebert, T. E. (2008) Combining protein complementation assays with resonance energy transfer to detect multipartner protein complexes in living cells. Methods, 45, 214-218.

4. Martel, C., Dugre-Brisson, S., Boulay, K., Breton, B., Lapointe, G., Armando, S., Trepanier, V., Duchaine, T., Bouvier, M. and Desgroseillers, L. (2010) Multimerization of Staufen1 in live cells. RNA, 16, 585-597.

5. Luker, G. D. and Luker, K. E. (2011) Luciferase protein complementation assays for bioluminescence imaging of cells and mice. Methods Mol Biol., 680, 29-43. Molecular Imaging, Chapter 22.

6. Mangelsdorf, D. J. and Evans, R. M. (1995) The RXR heterodimers and orphan receptors. Cell, 83, 841-850.

7. Maira, M., Martens, C., Philips, A. and Drouin, J. (1999) Heterodimerization between members of the Nur subfamily of orphan nuclear receptors as a novel mechanism for gene activation. Mol Cell Biol, 19, 7549-7557.

8. Robinson-Rechavi, M., Escriva Garcia, H. and Laudet, V. (2003) The nuclear receptor superfamily. J Cell Sci, 116, 585-586.

9. Kim, S. H., Tamrazi, A., Carlson, K. E. and Katzenellenbogen, J. A. (2005) A proteomic microarray approach for exploring ligand-initiated nuclear hormone receptor pharmacology, receptor selectivity, and heterodimer functionality. Mol Cell Proteomics, 4, 267-277.

10. Cotnoir-White, D., Laperriere, D. and Mader, S. (2011) Evolution of the repertoire of nuclear receptor binding sites in genomes. Mol Cell Endocrinol, 334, 76-82.

11. Saenz del Burgo, L. and Milligan, G. (2010) Heterodimerisation of G protein-coupled receptors: implications for drug design and ligand screening. Expert Opin Drug Discov, 5, 461-474.

12. Foord, S. M., Bonner, T. I., Neubig, R. R., Rosser, E. M., Pin, J. P., Davenport, A. P., Spedding, M. and Harmar, A. J. (2005) International Union of Pharmacology. XLVI. G protein-coupled receptor list. Pharmacol Rev, 57, 279-288.

13. Harmar, A. J., Hills, R. A., Rosser, E. M., Jones, M., Buneman, O. P., Dunbar, D. R., Greenhill, S. D., Hale, V. A., Sharman, J. L., Bonner, T. I. et al. (2009) IUPHAR-DB: the IUPHAR database of G protein-coupled receptors and ion channels. Nucleic Acids Res, 37, D680-685.

14. Sharman, J. L., Benson, H. E., Pawson, A. J., Lukito, V., Mpamhanga, C. P., Bombail, V., Davenport, A. P., Peters, J. A., Spedding, M. and Harmar, A. J. (2013) IUPHAR-DB: updated database content and new features. Nucleic Acids Res, 41, D1083-1088.

15. Kocan, M., See, H. B., Seeber, R. M., Eidne, K. A. and Pfleger, K. D. (2008) Demonstration of improvements to the bioluminescence resonance energy transfer (BRET) technology for the monitoring of G protein-coupled receptors in live cells. J Biomol Screen, 13, 888-898.

16. Webb, P., NGuyen, P., Shinsako, J., Anderson, C., Feng, W., Nguyen, M. P., Chen, D., Huang, S.-M., Subramanian, S., McKinerney, E. et al. (1998) Estrogen receptor activation function 1 works by binding p160 coactivator proteins. Mol. Endocrinol., 12, 1605-1618.

17. Tremblay, G. B., Tremblay, A., Labrie, F. and Giguere, V. (1999) Dominant activity of activation function 1 (AF-1) and differential stoichiometric requirements for AF-1 and -2 in the estrogen receptor alpha-beta heterodimeric complex. Mol Cell Biol, 19, 1919-1927.

18. Benecke, A., Chambon, P. and Gronemeyer, H. (2000) Synergy between estrogen receptor alpha activation functions AF1 and AF2 mediated by transcription intermediary factor TIF2. EMBO Rep, 1, 151-157.

19. Metivier, R., Penot, G., Flouriot, G. and Pakdel, F. (2001) Synergism between ERalpha transactivation function 1 (AF-1) and AF-2 mediated by steroid receptor coactivator protein-1: requirement for the AF-1 alpha-helical core and for a direct interaction between the N- and C-terminal domains. Mol Endocrinol, 15, 1953-1970.

20. Hilmi, K., Hussein, N., Mendoza-Sanchez, R., El-Ezzy, M., Ismail, H., Durette, C., Bail, M., Rozendaal, M. J., Bouvier, M., Thibault, P. et al. (2012) Role of SUMOylation in full antiestrogenicity. Mol Cell Biol, 32, 3823-3837.

21. Pfleger, K. D. and Eidne, K. A. (2006) Illuminating insights into protein-protein interactions using bioluminescence resonance energy transfer (BRET). Nat Methods, 3, 165-174.

22. Truong, K. and Ikura, M. (2001) The use of FRET imaging microscopy to detect protein-protein interactions and protein conformational changes in vivo. Curr Opin Struct Biol, 11, 573-578.

23. Haustein, E., Jahnz, M. and Schwille, P. (2003) Triple FRET: a tool for studying long-range molecular interactions. Chemphyschem, 4, 745-748.

24. Sun, Y., Wallrabe, H., Booker, C. F., Day, R. N. and Periasamy, A. (2010) Three-color spectral FRET microscopy localizes three interacting proteins in living cells. Biophys J, 99, 1274-1283.

25. Nilsson, S., Makela, S., Treuter, E., Tujague, M., Thomsen, J., Andersson, G., Enmark, E., Pettersson, K., Warner, M. and Gustafsson, J. A. (2001) Mechanisms of estrogen action. Physiol Rev, 81, 1535-1565.

26. Tamrazi, A., Carlson, K. E., Daniels, J. R., Hurth, K. M. and Katzenellenbogen, J. A. (2002) Estrogen receptor dimerization: ligand binding regulates dimer affinity and dimer dissociation rate. Mol Endocrinol, 16, 2706-2719.

27. Shiau, A. K., Barstad, D., Loria, P. M., Cheng, L., Kushner, P. J., Agard, D. A. and Greene, G. L. (1998) The structural basis of estrogen receptor/coactivator recognition and the antagonism of this interaction by tamoxifen. Cell, 95, 927-937.

28. Lupien, M., Jeyakumar, M., Hebert, E., Hilmi, K., Cotnoir-White, D., Loch, C., Auger, A., Dayan, G., Pinard, G. A., Wurtz, J. M. et al. (2007) Raloxifene and ICI182,780 increase estrogen receptor-alpha association with a nuclear compartment via overlapping sets of hydrophobic amino acids in activation function 2 helix 12. Mol Endocrinol, 21, 797-816.

29. Harrington, W. R., Sheng, S., Barnett, D. H., Petz, L. N., Katzenellenbogen, J. A. and Katzenellenbogen, B. S. (2003) Activities of estrogen receptor alpha- and beta-selective ligands at diverse estrogen responsive gene sites mediating transactivation or transrepression. Mol Cell Endocrinol, 206, 13-22.

30. Powell, E. and Xu, W. (2008) Intermolecular interactions identify ligand-selective activity of estrogen receptor alpha/beta dimers. Proc Natl Acad Sci USA, 105, 19012-19017.

31. Paulmurugan, R., Tamrazi, A., Massoud, T. F., Katzenellenbogen, J. A. and Gambhir, S. S. (2011) In vitro and in vivo molecular imaging of estrogen receptor alpha and beta homo- and heterodimerization: exploration of new modes of receptor regulation. Mol Endocrinol, 25, 2029-2040.
32. Osz, J., Brelivet, Y., Peluso-lltis, C., Cura, V., Eiler, S., Ruff, M., Bourguet, W., Rochel, N. and Moras, D. (2012) Structural basis for a molecular allosteric control mechanism of cofactor binding to nuclear receptors. Proc Natl Acad Sci USA, 109, E588-594.
33. Monroe, D. G., Secreto, F. J., Subramaniam, M., Getz, B. J., Khosla, S. and Spelsberg, T. C. (2005) Estrogen receptor alpha and beta heterodimers exert unique effects on estrogen- and tamoxifen-dependent gene expression in human U2OS osteosarcoma cells. Mol Endocrinol, 19, 1555-1568.
34. Leibowitz, M. D., Ardecky, R. J., Boehm, M. F., Broderick, C. L., Carfagna, M. A., Crombie, D. L., D'Arrigo, J., Etgen, G. J., Faul, M. M., Grese, T. A. et al. (2006) Biological characterization of a heterodimer-selective retinoid X receptor modulator: potential benefits for the treatment of type 2 diabetes. Endocrinology, 147, 1044-1053.
35. Powell, E., Shanle, E., Brinkman, A., Li, J., Keles, S., Wisinski, K. B., Huang, W. and Xu, W. (2012) Identification of estrogen receptor dimer selective ligands reveals growth-inhibitory effects on cells that co-express ERalpha and ERbeta. PLoS One, 7, e30993.
36. Vaz, B. and de Lera, A. R. (2012) Advances in drug design with RXR modulators. Expert Opin Drug Discov, 7, 1003-1016.

The invention claimed is:

1. A biosensor comprising:
   (A)
   (i) a first protein tagged with a Donor (D) protein, wherein D is a bioluminescent protein (Biol) having an emission spectrum (Biol-Em);
   (ii) a second protein tagged with an Intermediate (I) protein, wherein I is a first Fluorescent protein (FP1) having an excitation spectrum (FP1-Ex) and emission spectrum (FP1-Em);
   (iii) a third protein tagged with an Acceptor (A) protein, wherein A is a second fluorescent protein (FP2) having an excitation spectrum (FP2-Ex) and an emission spectrum (FP2-Em); and
   (iv) a bioluminescent protein substrate;
   wherein said substrate, Biol, FP1 and FP2 are selected such that:
   a) the FP1-Ex overlaps with the Biol-Em and overlaps minimally with the FP2-Ex;
   b) the FP1-Em overlaps with the FP2-Ex;
   c) the FP2-Ex overlaps with the Biol-Em; and
   d) the FP2-Em has a longer wavelength than the FP1-Em; or
   (B)
   (i) a first protein tagged with a first portion of a Donor protein (D1), wherein D1 is a first bioluminescent protein portion (BiolP1),
   (ii) a second protein tagged with a second portion of a Donor protein (D2), wherein D2 is a second bioluminescent protein portion (BiolP2), wherein interaction between said first and second proteins brings said BiolP1 and BiolP2 in close enough proximity to form a functional bioluminescent protein (Biol) having an emission spectrum Em;
   (iii) a third protein tagged with an Intermediate (I) protein, wherein I is a first Fluorescent protein (FP1) having an excitation spectrum (FP1-Ex) and emission spectrum (FP1-Em);
   (iv) a fourth protein tagged with an Acceptor (A) protein, wherein A is a second fluorescent protein (FP2) having an excitation spectrum (FP2-Ex) and an emission spectrum (FP2-Em); and
   (v) a bioluminescent protein substrate;
   wherein said substrate, Biol, FP1 and FP2 are selected such that:
   a) the FP1-Ex overlaps with the Biol-Em and overlaps minimally with the FP2-Ex;
   b) the FP1-Em overlaps with the FP2-Ex;
   c) The FP2-Ex overlaps with the Biol-Em; and
   d) The FP2-Em has a longer wavelength than the FP1-Em.

2. The biosensor of claim 1, wherein the bioluminescent protein is a luciferase.

3. The biosensor of claim 1, wherein FP1 is mTFP1 or mTagBFP2 fluorescent protein.

4. The biosensor of claim 1, wherein FP2 is Venus, Topaz or mTFP1 fluorescent protein.

5. The biosensor of claim 1, further comprising a cell expressing the proteins defined in items (i), (ii) and (iii) of part (A), or the proteins defined in items (i), (ii), (iii) and (iv) of part (B).

6. A method for the detection of a ternary or quaternary protein complex, the method comprising:
   (1)
   A) providing:
      (i) a first protein tagged with a Donor (D) protein, wherein D is a bioluminescent protein (Biol) having an emission spectrum (Biol-Em);
      (ii) a second protein tagged with an Intermediate (I) protein, wherein I is a first Fluorescent protein (FP1) having an excitation spectrum (FP1-Ex) and emission spectrum (FP1-Em);
      (iii) a third protein tagged with an Acceptor (A) protein, wherein A is a second fluorescent protein (FP2) having an excitation spectrum (FP2-Ex) and an emission spectrum (FP2-Em); and
      (iv) a bioluminescent protein substrate;
   wherein said substrate, Biol, FP1 and FP2 are selected such that:
      a) the FP1-Ex overlaps with the Biol-Em and overlaps minimally with the FP2-Ex;
      b) the FP1-Em overlaps with the FP2-Ex;
      c) the FP2-Ex overlaps with the Biol-Em; and
      d) the FP2-Em has a longer wavelength than the FP1-Em;
   and
   B) contacting the D protein with said bioluminescent protein substrate; and
   C) detecting Bioluminescence Resonance Energy Transfer Forster enhanced by simultaneous transfer (BRETFect) signal;
   wherein the detection of a BRETFect signal is indicative that a complex is formed; or
   (2)
   A) providing:
      (i) a first protein tagged with a first portion of a Donor protein (D1), wherein D1 is a first bioluminescent protein portion (BiolP1);
      (ii) a second protein tagged with a second portion of a Donor protein (D2), wherein D2 is a second bioluminescent protein portion (BiolP2), wherein interaction between said first and second proteins brings said BiolP1 and BiolP2 in close enough proximity to form a functional bioluminescent protein (Biol) having an emission spectrum Em
      (iii) a third protein tagged with an Intermediate (I) protein, wherein I is a first Fluorescent protein (FP1) having an excitation spectrum (FP1-Ex) and emission spectrum (FP1-Em);
      (iv) a fourth protein tagged with an Acceptor (A) protein, wherein A is a second fluorescent protein (FP2) having an excitation spectrum (FP2-Ex) and an emission spectrum (FP2-Em); and
      (v) a bioluminescent protein substrate;

wherein said substrate, Biol, FP1 and FP2 are selected such that:
  a) the FP1-Ex overlaps with the Biol-Em and overlaps minimally with the FP2-Ex;
  b) the FP1-Em overlaps with the FP2-Ex;
  c) The FP2-Ex overlaps with the Biol-Em; and
  d) The FP2-Em has a longer wavelength than the FP1-Em;
and
  B) contacting the Biol protein with said bioluminescent protein substrate; and
  C) detecting Bioluminescence Resonance Energy Transfer Forster enhanced by simultaneous transfer (BRETFect) signal;
wherein the detection of a BRETFect signal is indicative that a quaternary complex is formed.

7. The method of claim 6, wherein the detecting step in C) comprises detecting the D or Biol protein emission at about 485 nm and the A protein emission at between about 530 and 550 nm.

8. A method for determining whether an agent modulates the formation of a ternary or quaternary protein complex comprising performing the method of claim 6 in the presence and in the absence of said agent, wherein an increase in BRETFect signal in the presence of the agent relative to the absence thereof is indicative that the agent promotes the formation of the ternary or quaternary complex, and wherein a reduction in BRETFect signal in the presence of the agent relative to in the absence thereof is indicative that the agent inhibits the formation of the ternary or quaternary complex.

9. A kit comprising:
(A)
  a bioluminescent protein substrate; and
  one or more vectors for expressing:
    (i) a first protein tagged with a Donor (D) protein, wherein D is a bioluminescent protein (Biol) having an emission spectrum (Biol-Em);
    (ii) a second protein tagged with an Intermediate (I) protein, wherein I is a first Fluorescent protein (FP1) having an excitation spectrum (FP1-Ex) and emission spectrum (FP1-Em);
    (iii) a third protein tagged with an Acceptor (A) protein, wherein A is a second fluorescent protein (FP2) having an excitation spectrum (FP2-Ex) and an emission spectrum (FP2-Em);
  wherein said substrate, Biol, FP1 and FP2 are selected such that:
    a) the FP1-Ex overlaps with the Biol-Em and does not significantly overlaps with the FP2-Ex;
    b) the FP1-Em overlaps with FP2-Ex;
    c) the FP2-Ex overlaps with the Biol-Em; and
    d) the FP2-Em has a longer wavelength than the FP1-Em; or
(B)
  a bioluminescent protein substrate; and
  one or more vectors for expressing:
    (i) a first protein tagged with a first portion of a Donor protein (D1), wherein D1 is a first bioluminescent protein portion (BiolP1);
    (ii) a second protein tagged with a second portion of a Donor protein (D2), wherein D2 is a second bioluminescent protein portion (BiolP2);
    (iii) a third protein tagged with an Intermediate (I) protein, wherein I is a first Fluorescent protein (FP1) having an excitation spectrum (FP1-Ex) and emission spectrum (FP1-Em);
    (iv) a fourth protein tagged with an Acceptor (A) protein, wherein A is a second fluorescent protein (FP2) having an excitation spectrum (FP2-Ex) and an emission spectrum (FP2-Em);
  wherein said BiolP1 and BiolP2 can form a functional bioluminescent protein (Biol) having an emission spectrum Em if brought in close enough proximity, and wherein said substrate, Biol, FP1 and FP2 are selected such that:
    a) the FP1-Ex overlaps with the Biol-Em and does not significantly overlaps with the FP2-Ex;
    b) the FP1-Em overlaps with FP2-Ex;
    c) the FP2-Ex overlaps with the Biol-Em; and
    d) the FP2-Em has a longer wavelength than the FP1-Em.

* * * * *